United States Patent
Wu et al.

(10) Patent No.: US 12,371,466 B2
(45) Date of Patent: *Jul. 29, 2025

(54) CHIMERIC ANTIGEN RECEPTOR AND METHODS OF USE THEREOF

(71) Applicant: The Regents of the University of California, Oakland, CA (US)

(72) Inventors: Chia-Yung Wu, San Francisco, CA (US); James Onuffer, Alameda, CA (US); Wendell A. Lim, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1118 days.

This patent is subject to a terminal disclaimer.

(21) Appl. No.: 17/115,565

(22) Filed: Dec. 8, 2020

(65) Prior Publication Data

US 2021/0196757 A1 Jul. 1, 2021

Related U.S. Application Data

(60) Continuation of application No. 15/835,329, filed on Dec. 7, 2017, now Pat. No. 10,888,581, which is a continuation of application No. 15/801,133, filed on Nov. 1, 2017, now Pat. No. 10,105,391, which is a division of application No. 15/419,729, filed on Jan. 30, 2017, now Pat. No. 9,821,012, which is a continuation of application No. 15/064,938, filed on Mar. 9, 2016, now Pat. No. 9,587,020, which is a continuation of application No. 14/766,105, filed as application No. PCT/US2014/016527 on Feb. 14, 2014, now abandoned.

(60) Provisional application No. 61/765,585, filed on Feb. 15, 2013.

(51) Int. Cl.
| | |
|---|---|
| *A61K 35/17* | (2025.01) |
| *A61K 40/11* | (2025.01) |
| *A61K 40/31* | (2025.01) |
| *A61K 40/42* | (2025.01) |
| *A61K 47/68* | (2017.01) |
| *C07K 14/705* | (2006.01) |
| *C07K 14/725* | (2006.01) |
| *C07K 16/18* | (2006.01) |
| *C07K 16/28* | (2006.01) |
| *C12N 5/0783* | (2010.01) |
| *C12N 9/14* | (2006.01) |
| *C12N 9/90* | (2006.01) |
| *A61K 39/00* | (2006.01) |

(52) U.S. Cl.
CPC ............ *C07K 14/705* (2013.01); *A61K 35/17* (2013.01); *A61K 40/11* (2025.01); *A61K 40/31* (2025.01); *A61K 40/4211* (2025.01); *A61K 40/4255* (2025.01); *A61K 47/6891* (2017.08); *C07K 14/7051* (2013.01); *C07K 14/70521* (2013.01); *C07K 14/70575* (2013.01); *C07K 14/70578* (2013.01); *C07K 16/18* (2013.01); *C07K 16/2803* (2013.01); *C07K 16/2866* (2013.01); *C12N 5/0636* (2013.01); *C12N 9/14* (2013.01); *C12N 9/90* (2013.01); *C12Y 502/01008* (2013.01); *A61K 2039/505* (2013.01); *A61K 2239/23* (2023.05); *A61K 2239/24* (2023.05); *A61K 2239/31* (2023.05); *A61K 2239/38* (2023.05); *C07K 2317/622* (2013.01); *C07K 2319/00* (2013.01); *C07K 2319/03* (2013.01); *C07K 2319/20* (2013.01); *C07K 2319/33* (2013.01); *C07K 2319/74* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,359,046 A | 10/1994 | Capon et al. | |
| 5,712,149 A | 1/1998 | Roberts | |
| 5,830,462 A | 11/1998 | Crabtree et al. | |
| 5,834,266 A | 11/1998 | Crabtree et al. | |
| 5,869,337 A | 2/1999 | Crabtree et al. | |
| 5,871,753 A | 2/1999 | Crabtree et al. | |
| 5,906,936 A | 5/1999 | Eshhar et al. | |
| 5,912,172 A | 6/1999 | Eshhar et al. | |
| 6,133,456 A | 10/2000 | Holt et al. | |
| 6,150,527 A | 11/2000 | Holt et al. | |
| 6,165,787 A | 12/2000 | Crabtree et al. | |

(Continued)

FOREIGN PATENT DOCUMENTS

| | | |
|---|---|---|
| EP | 481673 | 4/1992 |
| FR | 2968013 | 6/2012 |

(Continued)

OTHER PUBLICATIONS

Kawahara et al. Engineering cytokine receptors to control cellular functions (Biochem Eng J. Feb. 15, 2010;48(3):283-294).*

(Continued)

*Primary Examiner* — Michael D Burkhart
(74) *Attorney, Agent, or Firm* — James S. Keddie; Bozicevic, Field & Francis LLP

(57) ABSTRACT

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided.

13 Claims, 64 Drawing Sheets
Specification includes a Sequence Listing.

(56) References Cited

U.S. PATENT DOCUMENTS

| | | |
|---|---|---|
| 6,410,319 B1 | 6/2002 | Raubitschek et al. |
| 6,649,595 B2 | 11/2003 | Clackson et al. |
| 7,404,950 B2 | 7/2008 | Spencer et al. |
| 7,446,179 B2 | 11/2008 | Jensen et al. |
| 7,446,190 B2 | 11/2008 | Sadelain et al. |
| 7,741,465 B1 | 6/2010 | Eshhar et al. |
| 8,106,191 B2 | 1/2012 | Holt et al. |
| 8,399,645 B2 | 3/2013 | Campana et al. |
| 8,492,122 B2 | 7/2013 | Ostermeier |
| 8,771,671 B2 | 7/2014 | Spencer et al. |
| 8,911,993 B2 | 12/2014 | June et al. |
| 8,999,949 B2 | 4/2015 | Spencer et al. |
| 9,587,020 B2 | 3/2017 | Wu et al. |
| 9,745,368 B2 | 8/2017 | Milone et al. |
| 9,821,012 B2 | 11/2017 | Wu et al. |
| 10,105,391 B2 | 10/2018 | Wu et al. |
| 10,287,354 B2 | 5/2019 | Brogdon et al. |
| 10,632,152 B2 | 4/2020 | Wu et al. |
| 2003/0077249 A1 | 4/2003 | Bebbington et al. |
| 2004/0038886 A1 | 2/2004 | Finney et al. |
| 2005/0113564 A1 | 5/2005 | Campana et al. |
| 2008/0057515 A1 | 3/2008 | Paszty et al. |
| 2011/0286980 A1 | 11/2011 | Brenner |
| 2012/0029063 A1 | 2/2012 | Zhang et al. |
| 2012/0108455 A1 | 5/2012 | Kodandapani et al. |
| 2012/0277286 A1 | 11/2012 | Youle et al. |
| 2013/0040836 A1 | 2/2013 | Himmler et al. |
| 2013/0095097 A1 | 4/2013 | Blankenship et al. |
| 2013/0195800 A1 | 8/2013 | Roeth et al. |
| 2014/0050708 A1 | 2/2014 | Powell et al. |
| 2014/0099309 A1 | 4/2014 | Powell et al. |
| 2014/0134142 A1 | 5/2014 | Smith et al. |
| 2014/0286987 A1 | 9/2014 | Spencer et al. |
| 2014/0308746 A1 | 10/2014 | Rossi et al. |
| 2015/0368342 A1 | 12/2015 | Wu et al. |
| 2017/0292118 A1 | 10/2017 | Duchateau et al. |
| 2017/0306303 A1 | 10/2017 | Taunton et al. |
| 2017/0340672 A1 | 11/2017 | Wu et al. |
| 2018/0085401 A1 | 3/2018 | Wu et al. |

FOREIGN PATENT DOCUMENTS

| | | |
|---|---|---|
| WO | WO 2001/032866 | 5/2001 |
| WO | WO 2002/070559 | 9/2002 |
| WO | WO 2011/119773 A1 | 9/2011 |
| WO | WO 2012/079000 | 6/2012 |
| WO | WO 2012/099973 A2 | 7/2012 |
| WO | WO 2014/039523 A1 | 3/2014 |
| WO | WO 2014/127261 | 8/2014 |
| WO | WO 2015/057852 | 4/2015 |
| WO | WO 2015/090229 | 6/2015 |
| WO | WO 2015/123527 A1 | 8/2015 |
| WO | WO 2015/142661 | 9/2015 |
| WO | WO 2015/150771 | 10/2015 |
| WO | WO 2016/055551 | 4/2016 |
| WO | WO 2017/087723 | 5/2017 |
| WO | WO 2017/120546 | 7/2017 |

OTHER PUBLICATIONS

Single-domain antibody—Wikipedia, pp. 1-11; down loaded Aug. 22, 2024.*

Di Stasi et al., "T lymphocytes coexpressing CCR4 and a chimeric antigen receptor targeting CD30 have improved homing and anti-tumor activity in a Hodgkin tumor model", Blood, 2009; 113 (25): 6392-6402.

Co-pending U.S. Appl. No. 15/801,133, filed Nov. 1, 2017.

Abate-Daga, et a.; "CAR models: next-generation CAR modifications for enhanced T-cell function"; Molecular Therapy-Oncolytics; vol. 3, 7 pages (2016).

Baitsch, et al.; "Extended Co-Expression of Inhibitory Receptors by Human CD8 T-Cells Depending on Differentiation, Antigen-Specificity and Anatomical Localization"; PLoS One; vol. 7, No. 2, 10 pages (Feb. 2012).

Barnea, et al.; "The genetic design of signaling cascades to record receptor activation"; PNAS; vol. 105, No. 1, pp. 64-69 (Jan. 8, 2008).

Chaudhry et al., "Energetics of glutamate receptor ligand binding domain dimer assembly are modulated by allosteric ions", PNAS, 2009, 106(30): 12329-12334.

Chen et al., "Overexpression of a glutamate receptor (GluR2) ligand binding domain in *Escherichia coli*: Application of a novel protein folding screen", Proc. Natl. Acad. Sci., 1997, 94: 13431-13436.

Co-pending U.S. Appl. No. 15/835,329, filed Dec. 7, 2017.

Camacho-Soto, et al.; "Ligand-Gated Split-Kinases"; Journal of the American Chemical Society; vol. 136, pp. 3995-4002 (2014).

Camacho-Soto, et al.; "Small Molecule Gated Split-Tyrosine Phosphatases and Orthogonal Split-Tyrosine Kinases"; Journal of the American Chemical Society; vol. 136, No. 49, 9 pages (2014).

Cartellieri, et al.; "Chimeric Antigen Receptor-Engineered T Cells for Immunotherapy of Cancer"; J. Biomed. Biotechnol.; vol. 2010, 13 pages (2010).

Chelur, et al.; "Targeted cell killing by reconstituted caspases"; PNAS; vol. 105, No. 2, pp. 2283-2288 (Feb. 13, 2007).

Curran, et al.; "Chimeric Antigen Receptors for T cell Immunotherapy: Current Understanding and Future Direction"; J. Gene. Med.; vol. 14, No. 6, pp. 405-445 (Jun. 2012).

Dasgupta, et al.; "Nuclear Receptor Coactivators: Master Regulators of Human Health and Disease"; Annu. Rev. Med.; vol. 65, pp. 279-292 (2014).

Davila, et al.; "How do CARs work?: Early insights from recent clinical studies targeting CD19"; Oncoimmunology; vol. 1, No. 9, pp. 1577-1583 (Dec. 1, 2012).

Derose, et al.; "Manipulating signaling at will: chemically-inducible dimerization (CID) techniques resolve problems in cell biology"; Pflugers Arch; vol. 465, No. 3, pp. 409-417 (Jan. 9, 2013).

Di Stasi, et al.; "Inducible apoptosis as a safety switch for adoptive cell therapy"; N Engl J Med; vol. 365, No. 18, pp. 1673-1683 (Nov. 3, 2011).

Dotti, et al.; "Design and development of therapies using chimeric antigen receptor-expressing T cells"; Immunological Reviews; vol. 257, pp. 107-126 (2014).

Duttagupta, et al.; "Costimulation Signals for Memory CD8+T Cells During Viral Infections"; Crit. Rev. Immunol.; vol. 29, No. 6, pp. 469-486 (2009).

Fegan, et al.; "Chemically controlled protein assembly: techniques and applications"; Chem Rev; vol. 110, No., 6, pp. 3315-3336 (Jun. 9, 2010).

Fridy, et al.; "A robust pipeline for rapid production of versatile nanobody repertoires"; Nat. Methods; vol. 11, No. 12, pp. 1253-1260 (Dec. 2014).

Fridy, et al.; "A robust pipeline for rapid production of versatile nanobody repertoires"; Nat. Methods; vol. 11, No. 12, pp. 1253-1260 (Dec. 2014)—Supplemental Materials.

Garfall, et al.; "Immunotherapy with Chimeric Antigen Receptors for Multiple Myeloma"; Discovery Medicine; vol. 17, No. 91, pp. 37-46 (Jan. 2014).

Gizinski, et al.; "Costimulation and T cells as therapeutic targets"; Best Pract. Res. Clin. Rheumatol.; vol. 24, No. 4, pp. 463-477 (Aug. 2010).

Gooz; "ADAM-17: The Enzyme That Does It All"; Crit. Rev. Biochem. Mol. Biol.; vol. 45, No. 2, pp. 146-169, 146-169 (Apr. 2010).

Gordon, et al.; "Effects of S1 cleavage on the structure, surface export, and signaling activity of human Notch1 and Notch2"; PLoS One; vol. 4, No. 8, 12 pages (Aug. 2009).

Graef, et al.; "Proximity and orientation underlie signaling by the non-receptor tyrosine kinase ZAP70"; EMBO J; vol. 16, No. 18, pp. 5618-5628 (Sep. 15, 1997).

Gurevich, et al.; "Corepressors of agonist-bound nuclear receptors"; Toxicology and Applied Pharmacology; vol. 223, pp. 288-298 (2007).

Heldin, et al.; "Dimerization of Cell Surface Receptors in Signal Transduction"; Cell; vol. 80, pp. 213-223 (Jan. 27, 1995).

(56) References Cited

OTHER PUBLICATIONS

Hultman, et al.; "The Ligand-Dependent Interaction of Mineralocorticoid Receptor with Coactivator and Corepressor Peptides Suggests Multiple Activation Mechanisms"; Molecular Endocrinology; vol. 19, No. 6, pp. 1460-1473 (Jun. 2005).
Isakov; "Immunoreceptor tyrosine-based activation motif (ITAM), a unique module linking antigen and Fc receptors to their signaling cascades"; J. Leukoc . Biol.; vol. 61, No. 1, pp. 6-16 (Jan. 1997).
James, et al.; "Biophysical mechanism of T-cell receptor triggering in a reconstituted system"; Nature; vol. 487, pp. 64-69 (Jul. 5, 2012).
Juillerat, et al.; "Design of chimeric antigen receptors with integrated controllable transient functions"; Scientific Reports; doi: 10.1038/srep18950; 7 pages (Jan. 11, 2016).
Kalos, et al.; "T Cells with Chimeric Antigen Receptors Have Potent Antitumor Effects and Can Establish Memory in Patients with Advanced Leukemia"; Sci Transl Med.; vol. 3, No. 95, 12 pages (Aug. 10, 2011).
Kawahara, et al.; "Engineering cytokine receptors to control cellular functions"; Biochemical Engineering Journal; vol. 48, pp. 283-294 (2010).
Kimchi-Sarfaty, et al.; "A 'Silent' Polymorphism in the MDR1 Gene Changes Substrate Specificity"; Science; vol. 315, pp. 525-528 (Jan. 26, 2007).
Klemm et al., "Dimerization as a Regulatory Mechanism in Signal Transduction", Annu. Rev. Immunol., 1998, 16: 569-592.
Kloss, et al.; "Combinatorial antigen recognition with balanced signaling promotes selective tumor eradication by engineered T cells"; Nat Biotechnol; vol. 31, pp. 71-75 (Dec. 16, 2012).
Kopan, et al.; "The Canonical Notch Signaling Pathway: Unfolding the Activation Mechanism"; Cell; vol. 137, pp. 216-233 (Apr. 17, 2009).
Lanitis et al., "Redirected Antitumor Activity of Primary Human Lymphocytes Transduced With a Fully Human Anti-mesothelin Chimeric Receptor", Molecular Therapy, Mar. 2012, 20(3): 633-643.
Lecourtois, et al.; "Indirect evidence for Delta-dependent intracellular processing of notch in Drosophila embryos"; Curr. Biol.; vol. 8, No. 13, pp. 771-774 (Jun. 1998).
Lemmon et al., "Cell signaling by receptor-tyrosine kinases", Cell, 2010, 141(7): 1117-1134.
Li et al., "Receptor tyrosine kinase transmembrane domains", Cell Adhesion & Migration, 2010, 4:2, 249-254.
Liu, et al.; "Construction of a fluorescein-responsive chimeric receptor with strict ligand dependency"; Biotechnol Bioeng. Dec. 1, 2008;101(5):975-84. doi: 10.1002/bit.21961.
Maus, et al.; "Antibody-modified T cells: CARs take the front seat for hematologic malignancies"; Blood; vol. 123, No. 17, pp. 2625-2635 (Apr. 24, 2014).
Matsuda, et al.; "Synthetic Signal Propagation Through Direct Cell-Cell Interaction"; Sci. Signal; vol. 5, No. 220, 9 pages (Apr. 17, 2012).
Maus et al., "Antibody-modified T cells: CARs take the front seat for hematologic malignancies", Blood, Apr. 24, 2014, 123(17): 2625-2635.
Mumm, et al.; "A ligand-induced extracellular cleavage regulates gamma-secretase-like proteolytic activation of Notch1"; Mol. Cell; vol. 5, No. 2, pp. 197-206 (Feb. 2000).
Nagy, et al.; "Mechanism of the nuclear receptor molecular switch"; Trends in Biochemical Sciences; vol. 29, No. 6, pp. 317-324 (Jun. 2004).
Ngo, et al.; "Computational Complexity, Protein Structure Prediction, and the Levinthal Paradox"; The Protein Folding Problem and Tertiary Structure Prediction; pp. 433 and 492-495 (1994).
Odorizzi, et al.; "Inhibitory Receptors on Lymphocytes: Insights from Infections"; J. Immunol.; vol. 188, No. 7, pp. 2957-2965 (Apr. 1, 2012).
Ogawa, et al.; "Construction of Unnatural Heterodimeric Receptors Based on IL-2 and IL-6 Receptor Subunits"; Biotechnol. Prog.; vol. 29, No. 6, pp. 1512-1518 (2013).
Olefsky, et al.; "Minireview Prologue: Nuclear Receptor Minireview Series"; J. Biol. Chem.; vol. 276, pp. 36863- 36864 (2001).
Ott et al., "Integral membrane protein biosynthesis: why topology is hard to predict", Journal of Cell Science, 2002, 115: 2003-2009.
Porter, et al.; "Chimeric antigen receptor-modified T cells in chronic lymphoid leukemia"; Engl J Med; vol. 365, No. 8, pp. 725-733 (Aug. 25, 2011).
Raulet; "Roles of the NKG2D Immunoreceptor and Its Ligands"; Nature Reviews Immunology; vol. 3, pp. 781-790 (Oct. 2003).
Robyr, et al.; "Nuclear Hormone Receptor Coregulators in Action: Diversity for Shared Tasks"; Molecular Endocrinology; vol. 14, No. 3, pp. 329-347 (2000).
Rosenberg; "Raising the bar: the curative potential of human cancer immunotherapy"; Science Translational Medicine; vol. 4, Issue 127, pp. 127ps8 (Mar. 23, 2012).
Sadelain, et al.; "The Basic Principles of Chimeric Antigen Receptor Design"; Cancer Discovery; vol. 3, No. 4, pp. 388-398 (Apr. 2013).
Sadelain, et al.; "The promise and potential pitfalls of chimeric antigen receptors"; Current Opinion in Immunology; vol. 21, No. 2, pp. 215-223 (Apr. 1, 2009).
Sanchez-Irizarry, et al.; "Notch Subunit Heterodimerization and Prevention of Ligand-Independent Proteolytic Activation Depend, Respectively, on a Novel Domain and the LNR Repeats"; Molecular and Cellular Biology; vol. 24, No. 21, 9265-9273 (Nov. 2004).
Schreiber; "Chemical Genetics Resulting from a Passion for Synthetic Organic Chemistry"; Bioorganic & Medicinal Chemistry; vol. 6, pp. 1127-1152 (1998).
Song, et al.; "In vivo persistence, tumor localization and anti-tumor activity of CAR engineered T cells is enhanced by costimulatory signaling through CD137 (4-1BB)"; Cancer Res.; vol. 71, No. 13, pp. 4617-4627 (Jul. 1, 2011).
Spencer et al., "Controlling Signal Transduction with Synthetic Ligands", Science, Nov. 12, 1993, 262: 1019-1024.
Springael et al., "Dimerization of chemokine receptors and its functional consequences", Cytokine & Growth Factor Reviews, 2005, 16: 611-623.
Stashi, et al.; "Steroid Receptor Coactivators: Servants and Masters for Control of Systems Metabolism"; Trends Endocrinol. Metab.; vol. 25, No. 7, pp. 337-347 (Jul. 2014).
Stroud et al., "Mechanistic Diversity of Cytokine Receptor Signaling Across Cell Membranes", Science's STKE., 2004: re7.
Struhl, et al.; "Nuclear access and action of notch in vivo"; Cell; vol. 93, No. 4, pp. 649-660 (May 15, 1998).
Stuhlmann-Laeisz, et al.; "Forced dimerization of gp130 leads to constitutive STAT3 activation, cytokine-independent growth, and blockade of differentiation of embryonic stem cells"; Mol Biol Cell. Jul. 2006; 17(7):2986-95. Epub Apr. 19, 2006.
Tal, et al.; "An NCR1-based chimeric receptor endows T-cells with multiple anti-tumor specificities"; Oncotarget; vol. 5, No. 21, pp. 10949-10958 (Apr. 24, 2014).
Tetel; "Nuclear receptor coactivators: Essential players in steroid hormone action in brain and behavior"; J. Neuroendocrinol; vol. 21, No. 4, pp. 229-237 (Mar. 2009).
Tone, et al.; "Cell Fate Conversion by Conditionally Switching the Signal-Transducing Domain of Signalobodies"; Biotechnology and Bioengineering; vol. 110, No. 12, pp. 3219-3226 (Dec. 2013).
Voet, et al.; Biochemistry; pp. 126-128 (1990).
Vooijs, et al.; "Mapping the consequence of Notch1 proteolysis in vivo with NIP-CRE"; Development; vol. 132, No. 3, pp. 535-544 (Feb. 2007).
Wang et al., "Structural Biology of Shared Cytokine Receptors", Annu Rev Immunol., 2009, 27: 29-60.
Weissman, et al.; "Molecular cloning and chromosomal localization of the human T-cell receptor zeta chain: distinction from the molecular CD3 complex"; PNAS; vol. 85, No. 24, pp. 9709-9713 (Dec. 1988).
Wu, et al.; "Remote control of therapeutic T cells through a small molecule-gated chimeric receptor"; Sciencexpress; sciencemag.org/content/early/recent; doi: 10.1126/science.aab4077; 15 pages (Sep. 24, 2015).

(56) References Cited

OTHER PUBLICATIONS

Yang et al., "Activation of Growth Hormone Receptors by Growth Hormone and Growth Hormone Antagonist Dimers: Insights into Receptor Triggering", Molecular Endocrinology, 2008, 22(4): 978-988.

Zhang et al., "LAT: The ZAP-70 Tyrosine Kinase Substrate that Links T Cell Receptor to Cellular Activation", Cell, Jan. 9, 1998, 92: 83-92.

Zhao, et al.; "Multiple injections of electroporated autologous T cells expressing a chimeric antigen receptor mediate regression of human disseminated tumor"; Cancer Res.; vol. 70, No. 22, pp. 9053-9061 (Nov. 15, 2010).

Bayle et al., "Rapamycin Analogs with Differential Binding Specificity Permit Orthogonal Control of Protein Activity", Chemistry & Biology, 2006, 13: 99-107.

Borras et al., "Generic Approach for the Generation of Stable Humanized Single-chain Fv Fragments from Rabbit Monoclonal Antibodies", The Journal of Biological Chemistry, 2010, 285(12): 9054-9066.

Chowdhury et al., "Isolation of a high-affinity stable single-chain Fv specific for mesothelin from DNA-immunized mice by phage display and construction of a recombinant immunotoxin with antitumor activity", Proc. Natl. Acad. Sci., 1998, 95: 669-674.

Ex Parte Luara S. Grosmaire et al., Decision on Appeal issued for U.S. Appl. No. 11/493,132, mailing date: Oct. 12, 2018.

Ho et al., "A novel high affinity human monoclonal antibody to mesothelin", Int J Cancer., 2011, 128(9): 2020-2030.

Kang et al., "Targeted Coating With Antigenic Peptide Renders Tumor Cells Susceptible to CD8+ T Cell-mediated Killing", Molecular Therapy, 2013, 21(3): 542-553.

Ma et al., "Recognition of Mesothelin by the Therapeutic Antibody MORAb-009", The Journal of Biological Chemistry, 2012, 287(40): 33123-33131.

Wei et al., "Target selection for CAR-T therapy", Journal of Hematology & Oncology, 2019, 12:62, 9 pages.

\* cited by examiner

Figures 1A and 1B. Construct #122, encoding a polypeptide comprising "anti-CD19 scFv – CD8 alpha hinge and transmembrane domain – FKBP"

Figure 1A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)
Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 1B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTAGGAAGCGGGTCCGGTAGCGGATCT (SEQ ID NO:9)
SLGSGSGSGS (SEQ ID NO:10)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGWEEGVAQMSVG
QRAKLTISPDYAYGATGHPGIIPPHATLVFDVELLKLE (SEQ ID NO:12)

Figures 2A and 2B. Construct #123, encoding a polypeptide comprising "FRB — CD3 zeta intracellular chain — mCherry"

Figure 2A

FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)

SRGSGSGSGS (SEQ ID NO:20)

Figure 2B
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGG
MDELYK (SEQ ID NO:22)

Figures 3A and 3B. Construct #125, encoding a conventional CAR comprising "anti-CD19 scFv – CD8 alpha hinge and transmembrane domain – 4-1BB & CD3 zeta intracellular chains"

Figure 3A

Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 3B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLLLSLVITLYC
(SEQ ID NO:8)

Linker:
TCCCTA
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:26)

Figure 4
Construct #126, encoding the fusion protein "FRB - mCherry"

FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 5A and 5B. Construct #168, encoding a polypeptide comprising "DAP10 extracellular domain - CD8 alpha transmembrane domain FRB CD3 zeta intracellular chain mCherry"

Figure 5A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:

Figure 5B
Human CD3 zeta intracellular chain:
AGAGTGAAGTTCAGCAGGAGCGCAGACGCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:

TCGCGAGGAAGCGGGTCCGGTAGCGGATCT (SEQ ID NO:19)

SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 6A-6C. Construct #169, encoding a polypeptide comprising "DAP10 extracellular domain - CD8 alpha transmembrane domain - FRB - 4-1BB & CD3 zeta intracellular chains - mCherry"

Figure 6A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Figure 6B
Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:

TCGCGAGGAAGCGGGTCCGGTAGCGGATCT (SEQ ID NO:19)

SRGSGSGSGS (SEQ ID NO:20)

Figure 6C
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 7A and 7B. Construct #170, encoding a polypeptide comprising "DAP10 extracellular domain - CD8 alpha transmembrane domain - FRB - mCherry"

Figure 7A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Figure 7B
Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 8A and 8B. Construct #197, encoding a polypeptide comprising "anti-CD19 scFv – CD8 alpha hinge and transmembrane domain – 4-1BB intracellular chain – FKBP"

Figure 8A

Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPSRFSGSGSGTD
YSLTISNLEQEDIATYFCQQGNTLPYTFGGGTKLEITGGGSGGGGSGGGGSEVKLQESGPGLVAPSQSL
SVTCTVSGVSLPDYGVSWIRQPPRKGLEWLGVIWGSETTYYNSALKSRLTIIKDNSKSQVFLKMNSLQTD
DTAIYYCAKHYYYGGSYAMDYWGQGTSVTVSS (SEQ ID NO:6)

Figure 8B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLLLSLVITLYC
(SEQ ID NO:8)

Linker:
TCCCTA
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)
KRGRKKLLYIFKQPFMRPVQTTQEEDGCSCRFPEEEEGGCEL (SEQ ID NO:24)

Linker:
TCGCGAGGAAGCGGGTCCGGTAGCGGATCT SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGWEEGVAQMSVG
QRAKLTISPDYAYGATGHPGIIPPHATLVFDVELLKLE (SEQ ID NO:12)

Figures 9A-C. Construct #206, encoding a polypeptide comprising "DAP10 extracellular domain - CD8 alpha transmembrane domain - 4-1BB intracellular chain - FRB - CD3 zeta intracellular chain - mCherry"

Figure 9A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
Tctctg
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)
KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

Figure 9B
FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYNELQKDKMAEA
YSEIGMKGERRRGKGHDGLYQGLSTATKDTYDALHMQALPPR (SEQ ID NO:18)

Linker:
TCGCGAGGAAGCGGGTCCGGTAGCGGATCT SEQ ID NO:19)
SRGSGSGSGS (SEQ ID NO:20)

Figure 9C
mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figures 10A and 10B. Construct #207, encoding a polypeptide comprising "DAP10 extracellular domain – CD8 alpha transmembrane domain – 4-1BB intracellular chain – FRB – mCherry"

Figure 10A

Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)
MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)
IYIWAPLAGTCGVLLLSLVITLYC (SEQ ID NO:30)

Linker:
Tctctg
SerLeu

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID NO:23)
KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

Figure 10B

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLMEAQEWCRKYMK
SGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figures 11A-C. Construct #199, encoding the fusion protein "FRB – Zap70 – mCherry"

Figure 11A
FRB:
ATGATCCTCTGGCATGAGATGTGGCATGAAGGCCTGGAAGAGGCATCTCGTTTGTACTTTGGGGAAAGGA
ACGTGAAAGGCATGTTTGAGGTGCTGGAGCCCTTGCATGCTATGATGGAACGGGGCCCCCAGACTCTGAA
GGAAACATCCTTTAATCAGGCCTATGGTCGAGATTTAATGGAGGCCCAAGAGTGGTGCAGGAAGTACATG
AAATCAGGGAATGTCAAGGACCTCCTCCAAGCCTGGGACCTCTATTATCATGTGTTCCGACGAATCTCAA
AG (SEQ ID NO:13)

MILWHEMWHEGLEEASRLYFGERNVKGMFEVLEPLHAMMERGPQTLKETSFNQAYGRDLMEAQEWCRKYM
KSGNVKDLLQAWDLYYHVFRRISK (SEQ ID NO:14)

Linker:
GGAAGCGGGTCCGGTAGCGGATCTTCCCTA (SEQ ID NO:15)
GSGSGSGSSL (SEQ ID NO:16)

Figure 11B
Human Zap70:

ATGCCAGACCCCGCGGCGCATCTGCCCTTCTTCTACGGCAGCATCTCGCGTGCCGAGGCCGAGGAGCACC
TGAAGCTGGCGGGCATGGCGGACGGGCTCTTCCTGCTGCGCCAGTGCCTGCGCTCGCTGGGCGGCTATGT
GCTGTCGCTCGTGCACGATGTGCGCTTCCACCACTTTCCCATCGAGCGCCAGCTCAACGGCACCTACGCC
ATTGCCGGCGGCAAAGCGCACTGTGGACCGGCAGAGCTCTGCGAGTTCTACTCGCGCGACCCCGACGGGC
TGCCCTGCAACCTGCGCAAGCCGTGCAACCGGCCGTCGGGCCTCGAGCCGCAGCCGGGGGTCTTCGACTG
CCTGCGAGACGCCATGGTGCGTGACTACGTGCGCCAGACGTGGAAGCTGGAGGGCGAGGCCCTGGAGCAG
GCCATCATCAGCCAGGCCCCGCAAGTGGAGAAGCTCATTGCTACGACGGCCCACGAGCGGATGCCCTGGT
ACCACAGCAGCCTGACGCGTGAGGAGGCCGAGCGCAAACTTTACTCTGGGGCGCAGACCGACGGCAAGTT
CCTGCTGAGGCCGCGGAAGGAGCAGGGCACATACGCCCTGTCCCTCATCTATGGGAAGACGGTGTACCAC
TACCTCATCAGCCAAGACAAGGCGGGCAAGTACTGCATTCCCGAGGGCACCAAGTTTGACACGCTCTGGC
AGCTGGTGGAGTATCTGAAGCTGAAGGCGGACGGGCTCATCTACTGCCTGAAGGAGGCCTGCCCCAACAG
CAGTGCCAGCAACGCCTCAGGGCTGCTGCTCCCACACTCCCAGCCCACCCATCCACGTTGACTCATCCT
CAGAGACGAATCGACACCCTCAACTCAGATGGATACACCCCTGAGCCAGCACGCATAACGTCCCCAGACA
AACCGCGGCCGATGCCCATGGACACGAGCGTGTATGAGAGCCCCTACAGCGACCCAGAGGAGCTCAAGGA
CAAGAAGCTCTTCCTGAAGCGCGATAACCTCCTCATAGCTGACATTGAACTTGGCTGCGGCAACTTTGGC
TCAGTGCGCCAGGGCGTGTACCGCATGCGCAAGAAGCAGATCGACGTGGCCATCAAGGTGCTGAAGCAGG
GCACGGAGAAGGCAGACACGGAAGAGATGATGCGCGAGGCGCAGATCATGCACCAGCTGGACAACCCCTA
CATCGTGCGGCTCATTGGCGTCTGCCAGGCCGAGGCCCTCATGCTGGTCATGGAGATGGCTGGGGGCGGG
CCGCTGCACAAGTTCCTGGTCGGCAAGAGGGAGGAGATCCCTGTGAGCAATGTGGCCGAGCTGCTGCACC
AGGTGTCCATGGGGATGAAGTACCTGGAGGAGAAGAACTTTGTGCACCGTGACCTGGCGGCCCGCAACGT
CCTGCTGGTTAACCGGCACTACGCCAAGATCAGCGACTTTGGCCTCTCCAAAGCACTGGGTGCCGACGAC
AGCTACTACACTGCCCGCTCAGCAGGGAAGTGGCCGCTCAAGTGGTACGCACCCGAATGCATCAACTTCC
GCAAGTTCTCCAGCCGCAGCGATGTCTGGAGCTATGGGGTCACCATGTGGGAGGCCTTGTCCTACGGCCA
GAAGCCCTACAAGAAGATGAAAGGGCCGGAGGTCATGGCCTTCATCGAGCAGGGCAAGCGGATGGAGTGC
CCACCAGAGTGTCCACCCGAACTGTACGCACTCATGAGTGACTGCTGGATCTACAAGTGGGAGGATCGCC
CCGACTTCCTGACCGTGGAGCAGCGCATGCGAGCCTGTTACTACAGCCTGGCCAGCAAGGTGGAAGGGCC
CCCAGGCAGCACACAGAAGGCTGAGGCTGCCTGTGCC (SEQ ID NO:35)

MPDPAAHLPFFYGSISRAEAEEHLKLAGMADGLFLLRQCLRSLGGYVLSLVHDVRFHHFPIERQLNGTYA
IAGGKAHCGPAELCEFYSRDPDGLPCNLRKPCNRPSGLEPQPGVFDCLRDAMVRDYVRQTWKLEGEALEQ
AIISQAPQVEKLIATTAHERMPWYHSSLTREEAERKLYSGAQTDGKFLLRPRKEQGTYALSLIYGKTVYH
YLISQDKAGKYCIPEGTKFDTLWQLVEYLKLKADGLIYCLKEACPNSSASNASGAAAPTLPAHPSTLTHP
QRRIDTLNSDGYTPEPARITSPDKPRPMPMDTSVYESPYSDPEELKDKKLFLKRDNLLIADIELGCGNFG
SVRQGVYRMRKKQIDVAIKVLKQGTEKADTEEMMREAQIMHQLDNPYIVRLIGVCQAEALMLVMEMAGGG
PLHKFLVGKREEIPVSNVAELLHQVSMGMKYLEEKNFVHRDLAARNVLLVNRHYAKISDFGLSKALGADD
SYYTARSAGKWPLKWYAPECINFRKFSSRSDVWSYGVTMWEALSYGQKPYKKMKGPEVMAFIEQGKRMEC
PPECPPELYALMSDCWIYKWEDRPDFLTVEQRMRACYYSLASKVEGPPGSTQKAEAACA (SEQ ID
NO:36)

Figure 11C
Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLPFAWDILSPQF
MYGSKAYVKHPADIPDYLKLSFPEGFKWERVMNFEDGGVVTVTQDSSLQDGEFIYKVKLRGTNFPSDGPV
MQKKTMGWEASSERMYPEDGALKGEIKQRLKLKDGGHYDAEVKTTYKAKKPVQLPGAYNVNIKLDITSHN
EDYTIVEQYERAEGRHSTGGMDELYK (SEQ ID NO:22)

Figure 18A

| | | | | |
|---|---|---|---|---|
| FKBP—FRB* <br> ITAM | FKBP—FRB* | FKBP—FRB* <br> ITAM | FKBP—FRB* <br> 4-1BB <br> ITAM | FKBP—FRB* |
| 122 + 123 | 122 + 126 | 122 + 168 | 122 + 169 | 122 + 170 |
| Induces modest NFAT-dependent transcription. | "No signaling" control for "122 + 123" | Stronger NFAT-dependent reporter gene induction than "122 + 123"; low IL-2 production. | Low IL-2 production. | "No signaling" control for "122 + 168/169/206" |

Figure 18B

| | | | |
|---|---|---|---|
| 122 + 206 | 197 + 168 | 197 + 206 | 197 + 207 |
| Strong reporter gene induction through NFAT; modest IL-2 production. | Strong reporter gene induction through NFAT; modest IL-2 production. | Strong cytokine production and cytotoxicity; robust On switch function. | "No ITAM" control for "197 + 168/206" |

357 + 206

270 + 206

336 + 337

365 + 367

399 + 400

366

398

Figures 22A and 22B. Construct #270, encoding a polypeptide comprising "anti-mesothelin SS1 scFv – CD8 alpha hinge and transmembrane domain – 4-1BB intracellular chain – FKBP"

Figure 22A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin SS1 scFv:
GGATCCCAGGTACAACTGCAGCAGTCTGGGCCTGAGCTGGAGAAGCCTGGCGCTTCAGTGAAGATATCCT
GCAAGGCTTCTGGTTACTCATTCACTGGCTACACCATGAACTGGGTGAAGCAGAGCCATGGAAAGAGCCT
TGAGTGGATTGGACTTATTACTCCTTACAATGGTGCTTCTAGCTACAACCAGAAGTTCAGGGGCAAGGCC
ACATTAACTGTAGACAAGTCATCCAGCACAGCCTACATGGACCTCCTCAGTCTGACATCTGAAGACTCTG
CAGTCTATTTCTGTGCAAGGGGGGGTTACGACGGGAGGGGTTTTGACTACTGGGGCCAAGGGACCACGGT
CACCGTCTCCTCAGGTGGAGGCGGTTCAGGCGGCGGTGGCTCTAGCGGTGGcGGATCGGACATCGAGCTC
ACTCAGTCTCCAGCAATCATGTCTGCATCTCCAGGGGAGAAGGTCACCATGACCTGCAGTGCCAGCTCAA
GTGTAAGTTACATGCACTGGTACCAGCAGAAGTCAGGCACCTCCCCCAAAAGATGGATTTATGACACATC
CAAACTGGCTTCTGGAGTCCCAGGTCGCTTCAGTGGCAGTGGGTCTGGAAACTCTTACTCTCTCACAATC
AGCAGCGTGGAGGCTGAAGATGATGCAACTTATTACTGCCAGCAGTGGAGTAAGCACCCTCTCACGTACG
GTGCTGGGACAAAGTTGGAAATCAAAGCTAGC (SEQ ID NO:133)

GSQVQLQQSGPELEKPGASVKISCKASGYSFTGYTMNWVKQSHGKSLEWIGLITPYNGAS
SYNQKFRGKATLTVDKSSSTAYMDLLSLTSEDSAVYFCARGGYDGRGFDYWGQGTTVTVS
SGGGGSGGGGSSGGGSDIELTQSPAIMSASPGEKVTMTCSASSSVSYMHWYQQKSGTSPK
RWIYDTSKLASGVPGRFSGSGSGNSYSLTISSVEAEDDATYYCQQWSKHPLTYGAGTKLE
IKAS (SEQ ID NO:134)

Figure 22B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 23A and 23B. Construct #300, encoding a polypeptide comprising "anti-mesothelin m912 scFv    CD8 alpha hinge and transmembrane domain    4-1BB intracellular chain    FKBP"

Figure 23A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti- mesothelin m912 scFv:
GGATCCCAGGTGCAGCTGCAGGAATCTGGCCCTGGCCTCGTGAAGCCCAGCGAGACACTGAGCCTGACCT
GTACCGTGTCTGGCGGCTCTGTGTCCAGCGGCAGCTACTACTGGTCCTGGATCAGACAGCCCCCTGGCAA
GGGCCTGGAATGGATCGGCTACATCTACTACAGCGGCTCCACCAACTACAACCCCAGCCTGAAGTCCAGA
GTGACCATCAGCGTGGACACCAGCAAGAACCAGTTCTCCCTGAAGCTGAGCAGCGTGACAGCCGCCGATA
CCGCCGTGTACTACTGTGCCAGAGAGGGCAAGAACGGCGCCTTCGACATCTGGGGCCAGGGCACAATGGT
CACCGTGTCATCTGGTGGAGGAGGATCTGGGGGAGGCGGAAGCGGAGGCGGCGGATCTGATATTCAGATG
ACCCAGAGCCCCAGCAGCCTGAGCGCCTCTGTGGGCGACAGAGTGACAATTACCTGCCGGGCCAGCCAGA
GCATCAGCAGCTACCTGAACTGGTATCAGCAGAAGCCCGGCAAGGCCCCCAAACTGCTGATCTACGCCGC
CAGCTCTCTGCAGTCTGGCGTGCCCAGCAGATTTTCCGGCTCTGGCAGCGGCACCGACTTCACCCTGACC
ATCTCTAGCCTGCAGCCCGAGGACTTCGCCACCTACTACTGCCAGCAGAGCTACAGCACCCCCCTGACCT
TTGGCGGAGGCACCAAGGTGGAAATCAAG (SEQ ID NO:135)

GSQVQLQESGPGLVKPSETLSLTCTVSGGSVSSGSYYWSWIRQPPGKGLEWIGYIYYSGS
TNYNPSLKSRVTISVDTSKNQFSLKLSSVTAADTAVYYCAREGKNGAFDIWGQGTMVTVS
SGGGGSGGGGSGGGGSDIQMTQSPSSLSASVGDRVTITCRASQSISSYLNWYQQKPGKAP
KLLIYAASSLQSGVPSRFSGSGSGTDFTLTISSLQPEDFATYYCQQSYSTPLTFGGGTKV
EIK (SEQ ID NO:136)

Figure 23B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 24A and 24B. Construct #336, encoding a polypeptide comprising "anti-CD19 scFv   CD8 alpha hinge and transmembrane domain   4-1BB intracellular chain   GID1A"

Figure 24A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Figure 24B
Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

GID1A:
ATGGCTGCGAGCGATGAAGTTAATCTTATTGAGAGCAGAACAGTGGTTCCTCTCAATACATGGGTTTTAA
TATCCAACTTCAAAGTAGCCTACAATATCCTTCGTCGCCCTGATGGAACCTTTAACCGACACTTAGCTGA
GTATCTAGACCGTAAAGTCACTGCAAACGCCAATCCGGTTGATGGGGTTTTCTCGTTCGATGTCTTGATT
GATCGCAGGATCAATCTTCTAAGCAGAGTCTATAGACCAGCTTATGCAGATCAAGAGCAACCTCCTAGTA
TTTTAGATCTCGAGAAGCCTGTTGATGGCGACATTGTCCCTGTTATATTGTTCTTCCATGGAGGTAGCTT
TGCTCATTCTTCTGCAAACAGTGCCATCTACGATACTCTTTGTCGCAGGCTTGTTGGTTTGTGCAAGTGT
GTTGTTGTCTCTGTGAATTATCGGCGTGCACCAGAGAATCCATACCCTTGTGCTTATGATGATGGTTGGA
TTGCTCTTAATTGGGTTAACTCGAGATCTTGGCTTAAATCCAAGAAAGACTCAAAGGTCCATATTTTCTT
GGCTGGTGATAGCTCTGGAGGTAACATCGCGCATAATGTGGCTTTAAGAGCGGGTGAATCGGGAATCGAT
GTTTTGGGGAACATTCTGCTGAATCCTATGTTTGGTGGGAATGAGAGAACGGAGTCTGAGAAAAGTTTGG
ATGGGAAATACTTTGTGACGGTTAGAGACCGCGATTGGTACTGGAAAGCGTTTTTACCCGAGGGAGAAGA
TAGAGAGCATCCAGCGTGTAATCCGTTTAGCCCGAGAGGGAAAAGCTTAGAAGGAGTGAGTTTCCCCAAG
AGTCTTGTGGTTGTCGCGGGTTTGGATTTGATTAGAGATTGGCAGTTGGCATACGCGGAAGGGCTCAAGA
AAGCGGGTCAAGAGGTTAAGCTTATGCATTTAGAGAAAGCAACTGTTGGGTTTTACCTCTTGCCTAATAA
CAATCATTTCCATAATGTTATGGATGAGATTTCGGCGTTTGTAAACGCGGAATGTATGCGTGAC (SEQ
ID NO:137)

MAASDEVNLIESRTVVPLNTWVLISNFKVAYNILRRPDGTFNRHLAEYLDRKVTANANPV
DGVFSFDVLIDRRINLLSRVYRPAYADQEQPPSILDLEKPVDGDIVPVILFFHGGSFAHS
SANSAIYDTLCRRLVGLCKCVVVSVNYRRAPENPYPCAYDDGWIALNWVNSRSWLKSKKD
SKVHIFLAGDSSGGNIAHNVALRAGESGIDVLGNILLNPMFGGNERTESEKSLDGKYFVT
VRDRDWYWKAFLPEGEDREHPACNPFSPRGKSLEGVSFPKSLVVVAGLDLIRDWQLAYAE
GLKKAGQEVKLMHLEKATVGFYLLPNNNHFHNVMDEISAFVNAECMRD (SEQ ID NO:138)

Figure 25A and 25B. Construct #337, encoding a polypeptide comprising "DAP10 extracellular domain – CD8 alpha transmembrane domain  4-1BB intracellular chain  GAI  CD3 zeta intracellular chain  mCherry"

Figure 25A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)

IYIWAPLAGTCGVLLLSLVITLYC (SEQ ID NO:30)

Linker:
Tctctg
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID NO:23)

KRGRKKLLYIFKQPFMRPVQTTQEEDGCSCRFPEEEEGGCEL (SEQ ID NO:24)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

GAI N terminus:
ATGAAGAGAGATCATCATCATCATCATCATCAAGATAAGAAGACTATGATGATGAATGAAGAAGACGACG
GTAACGGCATGGATGAGCTTCTAGCTGTTCTTGGTTACAAGGTTAGGTCATCCGAAATGGCTGATGTTGC
TCAGAAACTCGAGCAGCTTGAAGTTATGATGTCTAATGTTCAAGAAGACGATCTTTCTCAACTCGCTACT
GAGACTGTTCACTATAATCCGGCGGAGCTTTACACGTGGCTTGATTCTATGCTCACCGACCTTAAT
(SEQ ID NO:139)

MKRDHHHHHHQDKKTMMMNEEDDGNGMDELLAVLGYKVRSSEMADVAQKLEQLEVMMSNV
QEDDLSQLATETVHYNPAELYTWLDSMLTDLN (SEQ ID NO:140)

Figure 25B
Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 26A and 26B. Construct #357, encoding a polypeptide comprising "anti-mesothelin HN1 scFv    CD8 alpha hinge and transmembrane domain 4-1BB intracellular chain    FKBP"

Figure 26A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin HN1 scFv:
GGATCCCAGGTGCAGCTGGTGCAGTCTGGCGCCGAAGTGAAAAGACCAGGCGCCAGCGTGCAGGTCTCCT
GTAGAGCCAGCGGCTACAGCATCAACACCTACTACATGCAGTGGGTGCGCCAGGCCCCAGGCGCTGGACT
GGAATGGATGGGCGTGATCAACCCCAGCGGCGTGACAAGCTACGCCCAGAAATTCCAGGGCAGAGTGACC
CTGACCAACGACACCAGCACCAACACAGTGTACATGCAGCTGAACAGCCTGACCAGCGCCGACACCGCCG
TGTACTACTGTGCCAGATGGGCCCTGTGGGGCGACTTCGGCATGGATGTGTGGGGCAAGGGCACCCTCGT
GACCGTGTCTAGCGGAGGCGGAGGATCTGGCGGAGGGGGATCTGGAGGCGGCGGAAGCGACATCCAGATG
ACCCAGAGCCCTAGCACCCTGAGCGCCAGCATCGGCGATAGAGTGACCATCACCTGTCGGGCCAGCGAGG
GCATCTATCACTGGCTGGCCTGGTATCAGCAGAAGCCCGGCAAGGCCCCCAAGCTGCTGATCTACAAGGC
CAGCTCTCTGGCCTCTGGCGCCCCTAGCAGATTTTCTGGCAGCGGCTCCGGCACCGACTTCACCCTGACA
ATCAGCAGCCTGCAGCCCGACGACTTCGCCACCTACTATTGCCAGCAGTACAGCAACTACCCCCTGACCT
TCGGCGGAGGCACCAAGCTGGAAATCAAG (SEQ ID NO:141)

GSQVQLVQSGAEVKRPGASVQVSCRASGYSINTYYMQWVRQAPGAGLEWMGVINPSGVTS
YAQKFQGRVTLTNDTSTNTVYMQLNSLTSADTAVYYCARWALWGDFGMDVWGKGTLVTVS
SGGGGSGGGGSGGGGSDIQMTQSPSTLSASIGDRVTITCRASEGIYHWLAWYQQKPGKAP
KLLIYKASSLASGAPSRFSGSGSGTDFTLTISSLQPDDFATYYCQQYSNYPLTFGGGTKL
EIK (SEQ ID NO:142)

Figure 26B
Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 27A and 27B. Construct #365, encoding a polypeptide comprising "anti-CD19 scFv – CD8 alpha hinge – CD28 transmembrane domain and intracellular chain – FKBP"

Figure 27A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Figure 27B
Human CD8 alpha extracellular spacer/hinge:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGAT (SEQ
ID NO:143)

TTTPAPRPPTPAPTIASQPLSLRPEACRPAAGGAVHTRGLDFACD (SEQ ID NO:56)

Human CD28 transmembrane domain and intracellular signaling chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 28A and 28B. Construct #366, encoding a polypeptide comprising a conventional CAR "anti-CD19 scFv – CD8 alpha hinge – CD28 transmembrane domain and intracellular chain – CD3 zeta intracellular chain"

Figure 28A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Figure 28B
Human CD8 alpha extracellular spacer/hinge:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGAT (SEQ
ID NO:143)

TTTPAPRPPTPAPTIASQPLSLRPEACRPAAGGAVHTRGLDFACD (SEQ ID NO:56)

Human CD28 transmembrane domain and intracellular chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
TCGCGAGGAAGCGGGTCCGGTAGCGGATCT (SEQ ID NO:19)
SRGSGSGSGS (SEQ ID NO:20)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

Figure 29A and 29B. Construct #367, encoding a polypeptide comprising "DAP10 extracellular domain  CD28 transmembrane domain and intracellular chain  FRB  CD3 zeta intracellular chain  mCherry"

Figure 29A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD28 transmembrane domain and intracellular signaling chain:
TTTTGGGTGCTGGTGGTGGTTGGTGGAGTCCTGGCTTGCTATAGCTTGCTAGTAACAGTGGCCTTTATTA
TTTTCTGGGTGAGGAGTAAGAGGAGCAGGCTCCTGCACAGTGACTACATGAACATGACTCCCCGCCGCCC
CGGGCCCACCCGCAAGCATTACCAGCCCTATGCCCCACCACGCGACTTCGCAGCCTATCGCTCC (SEQ
ID NO:144)

FWVLVVVGGVLACYSLLVTVAFIIFWVRSKRSRLLHSDYMNMTPRRPGPTRKHYQPYAPP
RDFAAYRS (SEQ ID NO:121)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

ILWHEMWHEGLEEASRLYFGERNVKGMFEVLEPLHAMMERGPQTLKETSFNQAYGRDLME
AQEWCRKYMKSGNVKDLLQAWDLYYHVFRRISK (SEQ ID NO:34)

Linker:
GGAAGCGGGTCCGGTAGCGGATCTTCCCTA (SEQ ID NO:15)
GSGSGSGSSL (SEQ ID NO:16)

Figure 29B
Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 30A and 30B. Construct #398, encoding a polypeptide comprising a conventional CAR "anti-CD19 scFv  CD8 alpha hinge and transmembrane domain  OX40 & CD3 zeta intracellular chains"

Figure 30A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Linker:
TCCCTA
SL

Figure 30B
Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
TCGCGAGGAAGCGGGTCCGGTAGCGGATCT (SEQ ID NO:19)
SRGSGSGSGS (SEQ ID NO:20)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

Figure 31A and 31B. Construct #399, encoding a polypeptide comprising "anti-CD19 scFv    CD8 alpha hinge and transmembrane domain    OX40 intracellular chain    FKBP"

Figure 31A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Myc epitope tag:
GAGCAGAAGCTGATCAGCGAGGAGGACCTG (SEQ ID NO:3)
EQKLISEEDL (SEQ ID NO:4)

Anti-human CD19 scFv:
GACATCCAGATGACACAGACTACATCCTCCCTGTCTGCCTCTCTGGGAGACAGAGTCACCATCAGTTGCA
GGGCAAGTCAGGACATTAGTAAATATTTAAATTGGTATCAGCAGAAACCAGATGGAACTGTTAAACTCCT
GATCTACCATACATCAAGATTACACTCAGGAGTCCCATCAAGGTTCAGTGGCAGTGGGTCTGGAACAGAT
TATTCTCTCACCATTAGCAACCTGGAGCAAGAAGATATTGCCACTTACTTTTGCCAACAGGGTAATACGC
TTCCGTACACGTTCGGAGGGGGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGGTGGCGCCCTCACAGAGCCTG
TCCGTCACATGCACTGTCTCAGGGGTCTCATTACCCGACTATGGTGTAAGCTGGATTCGCCAGCCTCCAC
GAAAGGGTCTGGAGTGGCTGGGAGTAATATGGGGTAGTGAAACCACATACTATAATTCAGCTCTCAAATC
CAGACTGACCATCATCAAGGACAACTCCAAGAGCCAAGTTTTCTTAAAAATGAACAGTCTGCAAACTGAT
GACACAGCCATTTACTACTGTGCCAAACATTATTACTACGGTGGTAGCTATGCTATGGACTACTGGGGCC
AAGGAACCTCAGTCACCGTCTCCTCA (SEQ ID NO:5)

DIQMTQTTSSLSASLGDRVTISCRASQDISKYLNWYQQKPDGTVKLLIYHTSRLHSGVPS
RFSGSGSGTDYSLTISNLEQEDIATYFCQQGNTLPYTFGGGTKLEITGGGSGGGGSGGG
GSEVKLQESGPGLVAPSQSLSVTCTVSGVSLPDYGVSWIRQPPRKGLEWLGVIWGSETTY
YNSALKSRLTIIKDNSKSQVFLKMNSLQTDDTAIYYCAKHYYYGGSYAMDYWGQGTSVTV
SS (SEQ ID NO:6)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Figure 31B
Linker:
TCCCTA
SL

Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
TCGCGAGGAAGCGGGTCCGGTAGCGGATCT (SEQ ID NO:19)
SRGSGSGSGS (SEQ ID NO:20)

FKBP:
ATGGGAGTcCAGGTGGAAACCATCTCCCCAGGAGACGGGCGCACCTTCCCCAAGCGCGGCCAGACCTGCG
TGGTGCACTACACCGGGATGCTTGAAGATGGAAAGAAATTTGATTCCTCCCGGGACAGAAACAAGCCCTT
TAAGTTTATGCTAGGCAAGCAGGAGGTGATCCGAGGCTGGGAAGAAGGGGTTGCCCAGATGAGTGTGGGT
CAGAGAGCCAAACTGACTATATCTCCAGATTATGCCTATGGTGCCACTGGGCACCCAGGCATCATCCCAC
CACATGCCACTCTCGTCTTCGATGTGGAGCTTCTAAAACTGGAA (SEQ ID NO:11)

MGVQVETISPGDGRTFPKRGQTCVVHYTGMLEDGKKFDSSRDRNKPFKFMLGKQEVIRGW
EEGVAQMSVGQRAKLTISPDYAYGATGHPGIIPPHATLVFDVELLKLE (SEQ ID NO:12)

Figure 32A and 32B. Construct #400, encoding a polypeptide comprising "DAP10 extracellular domain – CD8 alpha transmembrane domain   OX40 intracellular chain    FRB    CD3 zeta intracellular chain    mCherry"

Figure 32A
Human DAP10 signal sequence and extracellular domain:
Atgatccatctgggtcacatcctcttcctgcttttgctcccagtggctgcagctcagacgactccaggag
agagatcatcactccctgccttttaccctggcacttcaggctcttgttccggatgtgggtccctctctct
gccg (SEQ ID NO:27)

MIHLGHILFLLLLPVAAAQTTPGERSSLPAFYPGTSGSCSGCGSLSLP (SEQ ID NO:28)

Human CD8alpha transmembrane domain:
ATCTACATCTGGGCGCCCTTGGCCGGGACTTGTGGGGTCCTTCTCCTGTCACTGGTTATCACCCTTTACT
GC (SEQ ID NO:29)

IYIWAPLAGTCGVLLLSLVITLYC (SEQ ID NO:30)

Linker:
Tctctg
SL

Human OX40 intracellular chain:
CGGAGGGACCAGAGGCTGCCCCCCGATGCCCACAAGCCCCCTGGGGGAGGCAGTTTCCGGACCCCCATCC
AAGAGGAGCAGGCCGACGCCCACTCCACCCTGGCCAAGATC (SEQ ID NO:145)

RRDQRLPPDAHKPPGGGSFRTPIQEEQADAHSTLAKI (SEQ ID NO:65)

Linker:
GGtTCCGGcAGCGGaTCTGGtAGcGGAAGCGGGTCCGGTAGCGGATCT (SEQ ID NO:31)
GSGSGSGSGSGSGSGS (SEQ ID NO:32)

FRB:
ATCCTCTGGCATGAGATGTGGCATGAAGGCCTGGAAGAGGCATCTCGTTTGTACTTTGGGGAAAGGAACG
TGAAAGGCATGTTTGAGGTGCTGGAGCCCTTGCATGCTATGATGGAACGGGGCCCCCAGACTCTGAAGGA
AACATCCTTTAATCAGGCCTATGGTCGAGATTTAATGGAGGCCCAAGAGTGGTGCAGGAAGTACATGAAA
TCAGGGAATGTCAAGGACCTCCTCCAAGCCTGGGACCTCTATTATCATGTGTTCCGACGAATCTCAAAG
(SEQ ID NO:33)

Figure 32B
Linker:
GGAAGCGGGTCCGGTAGCGGATCTTCCCTA (SEQ ID NO:15)
GSGSGSGSSL (SEQ ID NO:16)

Human CD3 zeta intracellular chain:
AGAGTGAAGTTCAGCAGGAGCGCAGACGCCCCCGCGTACCAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCCCCTCGC (SEQ ID
NO:17)

RVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:18)

Linker:
TCGCGAGGAAGCGGGTCCGGTAGCGGATCT (SEQ ID NO:19)
SRGSGSGSGS (SEQ ID NO:20)

mCherry:
ATGGTGAGCAAGGGCGAGGAGGATAACATGGCCATCATCAAGGAGTTCATGCGCTTCAAGGTGCACATGG
AGGGCTCCGTGAACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGTCCCCTCAGTTC
ATGTACGGCTCCAAGGCCTACGTGAAGCACCCCGCCGACATCCCCGACTACTTGAAGCTGTCCTTCCCCG
AGGGCTTCAAGTGGGAGCGCGTGATGAACTTCGAGGACGGCGGCGTGGTGACCGTGACCCAGGACTCCTC
CCTGCAGGACGGCGAGTTCATCTACAAGGTGAAGCTGCGCGGCACCAACTTCCCCTCCGACGGCCCCGTA
ATGCAGAAGAAGACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAGACCACCTACAA
GGCCAAGAAGCCCGTGCAGCTGCCCGGCGCCTACAACGTCAACATCAAGTTGGACATCACCTCCCACAAC
GAGGACTACACCATCGTGGAACAGTACGAACGCGCCGAGGGCCGCCACTCCACCGGCGGCATGGACGAGC
TGTACAAG (SEQ ID NO:21)

MVSKGEEDNMAIIKEFMRFKVHMEGSVNGHEFEIEGEGEGRPYEGTQTAKLKVTKGGPLP
FAWDILSPQFMYGSKAYVKHPADIPDYLKLSFPEGFKWERVMNFEDGGVVTVTQDSSLQD
GEFIYKVKLRGTNFPSDGPVMQKKTMGWEASSERMYPEDGALKGEIKQRLKLKDGGHYDA
EVKTTYKAKKPVQLPGAYNVNIKLDITSHNEDYTIVEQYERAEGRHSTGGMDELYK (SEQ ID
NO:22)

Figure 33A and 33B. Construct #358, encoding a polypeptide comprising a conventional CAR "anti-mesothelin HN1 scFv   CD8 alpha hinge and transmembrane domain   4-1BB & CD3 zeta intracellular chains"

Figure 33A
Signal peptide:
ATGGCCTTACCAGTGACCGCCTTGCTCCTGCCGCTGGCCTTGCTGCTCCACGCCGCCAGGCCG (SEQ ID NO:1)
MALPVTALLLPLALLLHAARP (SEQ ID NO:2)

Flag epitope tag:
GATTACAAGGATGACGATGACAAG (SEQ ID NO:132)
DYKDDDDK (SEQ ID NO:123)

Anti-human mesothelin HN1 scFv:
GGATCCCAGGTGCAGCTGGTGCAGTCTGGCGCCGAAGTGAAAAGACCAGGCGCCAGCGTGCAGGTCTCCT
GTAGAGCCAGCGGCTACAGCATCAACACCTACTACATGCAGTGGGTGCGCCAGGCCCCAGGCGCTGGACT
GGAATGGATGGGCGTGATCAACCCCAGCGGCGTGACAAGCTACGCCCAGAAATTCCAGGGCAGAGTGACC
CTGACCAACGACACCAGCACCAACACAGTGTACATGCAGCTGAACAGCCTGACCAGCGCCGACACCGCCG
TGTACTACTGTGCCAGATGGGCCCTGTGGGGCGACTTCGGCATGGATGTGTGGGGCAAGGGCACCCTCGT
GACCGTGTCTAGCGGAGGCGGAGGATCTGGCGGAGGGGGATCTGGAGGCGGCGGAAGCGACATCCAGATG
ACCCAGAGCCCTAGCACCCTGAGCGCCAGCATCGGCGATAGAGTGACCATCACCTGTCGGGCCAGCGAGG
GCATCTATCACTGGCTGGCCTGGTATCAGCAGAAGCCCGGCAAGGCCCCCAAGCTGCTGATCTACAAGGC
CAGCTCTCTGGCCTCTGGCGCCCCTAGCAGATTTTCTGGCAGCGGCTCCGGCACCGACTTCACCCTGACA
ATCAGCAGCCTGCAGCCCGACGACTTCGCCACCTACTATTGCCAGCAGTACAGCAACTACCCCCTGACCT
TCGGCGGAGGCACCAAGCTGGAAATCAAG (SEQ ID NO:141)

GSQVQLVQSGAEVKRPGASVQVSCRASGYSINTYYMQWVRQAPGAGLEWMGVINPSGVTS
YAQKFQGRVTLTNDTSTNTVYMQLNSLTSADTAVYYCARWALWGDFGMDVWGKGTLVTVS
SGGGGSGGGGSGGGGSDIQMTQSPSTLSASIGDRVTITCRASEGIYHWLAWYQQKPGKAP
KLLIYKASSLASGAPSRFSGSGSGTDFTLTISSLQPDDFATYYCQQYSNYPLTFGGGTKL
EIK (SEQ ID NO:142)

Human CD8 alpha extracellular spacer/hinge and transmembrane domain:
ACCACGACGCCAGCGCCGCGACCACCAACACCGGCGCCCACCATCGCGTCGCAGCCCCTGTCCCTGCGCC
CAGAGGCGTGCCGGCCAGCGGCGGGGGGCGCAGTGCACACGAGGGGGCTGGACTTCGCCTGTGATATCTA
CATCTGGGCGCCCTTGGCCGGGACTTGTGGGGTCCTTCTCCTGTCACTGGTTATCACCCTTTACTGC
(SEQ ID NO:7)

TTTPAPRPPTPAPTIASQPLSLRPEACRPAAGGAVHTRGLDFACDIYIWAPLAGTCGVLL
LSLVITLYC (SEQ ID NO:8)

Figure 33B
Linker:
TCCCTA
SL

Human 4-1BB intracellular chain:
AAACGGGGCAGAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG (SEQ ID
NO:23)

KRGRKKLLYIFKQPFMRPVQTTQEEDGCSCRFPEEEEGGCEL (SEQ ID NO:24)

Human CD3 zeta intracellular chain:
AGAGTGAAGTTCAGCAGGAGCGCAGACGCCCCCGCGTACAAGCAGGGCCAGAACCAGCTCTATAACGAGC
TCAATCTAGGACGAAGAGAGGAGTACGATGTTTTGGACAAGAGACGTGGCCGGGACCCTGAGATGGGGGG
AAAGCCGAGAAGGAAGAACCCTCAGGAAGGCCTGTACAATGAACTGCAGAAAGATAAGATGGCGGAGGCC
TACAGTGAGATTGGGATGAAAGGCGAGCGCCGGAGGGGCAAGGGGCACGATGGCCTTTACCAGGGTCTCA
GTACAGCCACCAAGGACACCTACGACGCCCTTCACATGCAGGCCCTGCCtCCTCGC (SEQ ID
NO:25)

RVKFSRSADAPAYKQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR (SEQ ID NO:26)

SEQUENCE LISTING

```
<160> NUMBER OF SEQ ID NOS: 145

<210> SEQ ID NO 1
<211> LENGTH: 63
<212> TYPE: DNA
<213> ORGANISM: Artificial Sequence
<220> FEATURE:
<223> OTHER INFORMATION: synthetic polynucleotide

<400> SEQUENCE: 1
atggccttac cagtgaccgc cttgctcctg ccgctggcct tgctgctcca cgccgccagg    60
ccg                                                                 63

<210> SEQ ID NO 2
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 2

Met Ala Leu Pro Val Thr Ala Leu Leu Leu Pro Leu Ala Leu Leu Leu
1               5                   10                  15

His Ala Ala Arg Pro
            20

<210> SEQ ID NO 3
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 3
gagcagaagc tgatcagcga ggaggacctg                                    30

<210> SEQ ID NO 4
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 4

Glu Gln Lys Leu Ile Ser Glu Glu Asp Leu
1               5                   10

<210> SEQ ID NO 5
<211> LENGTH: 726
<212> TYPE: DNA
<213> ORGANISM: Artificial Sequence
<220> FEATURE:
<223> OTHER INFORMATION: synthetic polynucleotide

<400> SEQUENCE: 5
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat acactcagg  agtcccatca   180 aggttcagtg gcagtgggtc tggaacagat tattctctca ccattagcaa cctggagcaa   240
gaagatattg ccacttactt ttgccaacag ggtaatacgc ttccgtacac gttcggaggg   300
```

```
gggaccaagc tggagatcac aggtggcggt ggctcgggcg gtggtgggtc gggtggcggc    360
ggatctgagg tgaaactgca ggagtcagga cctggcctgg tggcgccctc acagagcctg    420
tccgtcacat gcactgtctc agggtctca ttacccgact atggtgtaag ctggattcgc    480
cagcctccac gaaagggtct ggagtggctg ggagtaatat ggggtagtga aaccacatac    540
tataattcag ctctcaaatc cagactgacc atcatcaagg acaactccaa gagccaagtt    600
ttcttaaaaa tgaacagtct gcaaactgat gacacagcca tttactactg tgccaaacat    660
tattactacg gtggtagcta tgctatggac tactggggcc aaggaacctc agtcaccgtc    720
tcctca                                                               726
```

```
<210> SEQ ID NO 6
<211> LENGTH: 242
<212> TYPE: PRT
<213> ORGANISM: Artificial Sequence
<220> FEATURE:
<223> OTHER INFORMATION: synthetic polypeptide

<400> SEQUENCE: 6

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 7
<211> LENGTH: 207
<212> TYPE: DNA
<213> ORGANISM: Artificial Sequence
```

<220> FEATURE:
<223> OTHER INFORMATION: synthetic polynucleotide

<400> SEQUENCE: 7
accacgacgc cagcgccgcg accaccaaca ccggcgccca ccatcgcgtc gcagcccctg    60
tccctgcgcc cagaggcgtg ccggccagcg gcgggggggcg cagtgcacac gaggggggctg    120 gacttcgcct gtgatatcta catctgggcg cccttggccg ggacttgtgg ggtccttctc    180
ctgtcactgg ttatcaccct ttactgc    207

<210> SEQ ID NO 8
<211> LENGTH: 69
<212> TYPE: PRT
<213> ORGANISM: Artificial Sequence
<220> FEATURE:
<223> OTHER INFORMATION: synthetic polypeptide

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 9
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 9
tccctaggaa gcgggtccgg tagcggatct    30

<210> SEQ ID NO 10
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 10

Ser Leu Gly Ser Gly Ser Gly Ser Gly Ser
1               5                   10

<210> SEQ ID NO 11
<211> LENGTH: 324
<212> TYPE: DNA
<213> ORGANISM: Artificial Sequence
<220> FEATURE:
<223> OTHER INFORMATION: synthetic polynucleotide

<400> SEQUENCE: 11
atgggagtcc aggtggaaac catctcccca ggagacgggc gcaccttccc caagcgcggc    60
cagacctgcg tggtgcacta caccgggatg cttgaagatg gaaagaaatt tgattcctcc    120
cgggacagaa acaagccctt taagtttatg ctaggcaagc aggaggtgat ccgaggctgg    180

```
gaagaagggg ttgcccagat gagtgtgggt cagagagcca aactgactat atctccagat    240
tatgcctatg gtgccactgg gcacccaggc atcatcccac cacatgccac tctcgtcttc    300
gatgtggagc ttctaaaact ggaa                                          324
```

<210> SEQ ID NO 12
<211> LENGTH: 108
<212> TYPE: PRT
<213> ORGANISM: Artificial Sequence
<220> FEATURE:
<223> OTHER INFORMATION: synthetic polypeptide

<400> SEQUENCE: 12

```
Met Gly Val Gln Val Glu Thr Ile Ser Pro Gly Asp Gly Arg Thr Phe
1               5                   10                  15
Pro Lys Arg Gly Gln Thr Cys Val Val His Tyr Thr Gly Met Leu Glu
            20                  25                  30
Asp Gly Lys Lys Phe Asp Ser Ser Arg Asp Arg Asn Lys Pro Phe Lys
        35                  40                  45
Phe Met Leu Gly Lys Gln Glu Val Ile Arg Gly Trp Glu Glu Gly Val
    50                  55                  60
Ala Gln Met Ser Val Gly Gln Arg Ala Lys Leu Thr Ile Ser Pro Asp
65                  70                  75                  80
Tyr Ala Tyr Gly Ala Thr Gly His Pro Gly Ile Ile Pro Pro His Ala
                85                  90                  95
Thr Leu Val Phe Asp Val Glu Leu Leu Lys Leu Glu
            100                 105
```

<210> SEQ ID NO 13
<211> LENGTH: 282
<212> TYPE: DNA
<213> ORGANISM: Artificial Sequence
<220> FEATURE:
<223> OTHER INFORMATION: synthetic polynucleotide

<400> SEQUENCE: 13

```
atgatcctct ggcatgagat gtggcatgaa ggcctggaag aggcatctcg tttgtacttt     60
ggggaaagga acgtgaaagg catgtttgag gtgctggagc ccttgcatgc tatgatggaa    120
cggggccccc agactctgaa ggaaacatcc tttaatcagg cctatggtcg agatttaatg    180
gaggcccaag agtggtgcag gaagtacatg aaatcaggga atgtcaagga cctcctccaa    240
gcctgggacc tctattatca tgtgttccga cgaatctcaa ag                       282
```

<210> SEQ ID NO 14
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 14

```
Met Ile Leu Trp His Glu Met Trp His Glu Gly Leu Glu Glu Ala Ser
1               5                   10                  15
Arg Leu Tyr Phe Gly Glu Arg Asn Val Lys Gly Met Phe Glu Val Leu
            20                  25                  30
Glu Pro Leu His Ala Met Met Glu Arg Gly Pro Gln Thr Leu Lys Glu
        35                  40                  45
Thr Ser Phe Asn Gln Ala Tyr Gly Arg Asp Leu Met Glu Ala Gln Glu
    50                  55                  60
```

Trp Cys Arg Lys Tyr Met Lys Ser Gly Asn Val Lys Asp Leu Leu Gln
65                  70                  75                  80

Ala Trp Asp Leu Tyr Tyr His Val Phe Arg Arg Ile Ser Lys
                85                  90

<210> SEQ ID NO 15
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 15
ggaagcgggt ccggtagcgg atcttcccta                                       30

<210> SEQ ID NO 16
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 16

Gly Ser Gly Ser Gly Ser Gly Ser Ser Leu
1               5                   10

<210> SEQ ID NO 17
<211> LENGTH: 336
<212> TYPE: DNA
<213> ORGANISM: Artificial Sequence
<220> FEATURE:
<223> OTHER INFORMATION: synthetic polynucleotide

<400> SEQUENCE: 17
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                                336

<210> SEQ ID NO 18
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 18

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala

```
                    85                  90                  95

Thr Lys Asp Thr Tyr Asp Ala Leu His Met Gln Ala Leu Pro Pro Arg
            100                 105                 110
```

<210> SEQ ID NO 19
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 19

```
tcgcgaggaa gcgggtccgg tagcggatct                                    30
```

<210> SEQ ID NO 20
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 20

```
Ser Arg Gly Ser Gly Ser Gly Ser Gly Ser
1               5                   10
```

<210> SEQ ID NO 21
<211> LENGTH: 708
<212> TYPE: DNA
<213> ORGANISM: Artificial Sequence
<220> FEATURE:
<223> OTHER INFORMATION: synthetic polynucleotide

<400> SEQUENCE: 21

```
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc cctcagttc atgtacggct ccaaggccta cgtgaagcac      240
cccgccgaca tccccgacta cttgaagctg tccttcccg agggcttcaa gtgggagcgc      300
gtgatgaact cgaggacgg cggcgtggtg accgtgaccc aggactcctc cctgcaggac      360
ggcgagttca tctacaaggt gaagctgcgc ggcaccaact tccctctcga cggccccgta     420
atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg gccgccactc caccggcggc atggacgagc tgtacaag               708
```

<210> SEQ ID NO 22
<211> LENGTH: 236
<212> TYPE: PRT
<213> ORGANISM: Artificial Sequence
<220> FEATURE:
<223> OTHER INFORMATION: synthetic polypeptide

<400> SEQUENCE: 22

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30
```

Glu Ile Glu Gly Glu Gly Glu Gly Arg Pro Tyr Glu Gly Thr Gln Thr
         35                  40                  45

Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
   130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 23
<211> LENGTH: 126
<212> TYPE: DNA
<213> ORGANISM: Artificial Sequence
<220> FEATURE:
<223> OTHER INFORMATION: synthetic polynucleotide

<400> SEQUENCE: 23 aaacgggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 24
<211> LENGTH: 42
<212> TYPE: PRT
<213> ORGANISM: Artificial Sequence
<220> FEATURE:
<223> OTHER INFORMATION: synthetic polypeptide

<400> SEQUENCE: 24

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 25
<211> LENGTH: 336
<212> TYPE: DNA

<213> ORGANISM: Artificial Sequence
<220> FEATURE:
<223> OTHER INFORMATION: synthetic polynucleotide

<400> SEQUENCE: 25

```
agagtgaagt tcagcaggag cgcagacgcc cccgcgtaca agcagggcca gaaccagctc      60
tataacgagc tcaatctagg acgaagagag gagtacgatg tttttggacaa gagacgtggc    120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgcct cctcgc                              336
```

<210> SEQ ID NO 26
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 26

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 27
<211> LENGTH: 144
<212> TYPE: DNA
<213> ORGANISM: Artificial Sequence
<220> FEATURE:
<223> OTHER INFORMATION: synthetic polynucleotide

<400> SEQUENCE: 27

```
atgatccatc tgggtcacat cctcttcctg cttttgctcc cagtggctgc agctcagacg       60
actccaggag agagatcatc actccctgcc ttttaccctg gcacttcagg ctcttgttcc      120
ggatgtgggt ccctctctct gccg                                             144
```

<210> SEQ ID NO 28
<211> LENGTH: 48
<212> TYPE: PRT
<213> ORGANISM: Artificial Sequence
<220> FEATURE:
<223> OTHER INFORMATION: synthetic polypeptide

<400> SEQUENCE: 28

```
Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
```

```
                    20                  25                  30

Pro Gly Thr Ser Gly Ser Cys Ser Gly Cys Gly Ser Leu Ser Leu Pro
        35                  40                  45

<210> SEQ ID NO 29
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 29
atctacatct gggcgccctt ggccgggact tgtggggtcc ttctcctgtc actggttatc    60
accctttact gc                                                       72

<210> SEQ ID NO 30
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 30

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 31
<211> LENGTH: 48
<212> TYPE: DNA
<213> ORGANISM: Artificial Sequence
<220> FEATURE:
<223> OTHER INFORMATION: synthetic polynucleotide

<400> SEQUENCE: 31
ggttccggca gcggatctgg tagcggaagc gggtccggta gcggatct                48

<210> SEQ ID NO 32
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 32

Gly Ser Gly Ser Gly Ser Gly Ser Gly Ser Gly Ser Gly Ser Gly Ser
1               5                   10                  15

<210> SEQ ID NO 33
<211> LENGTH: 279
<212> TYPE: DNA
<213> ORGANISM: Artificial Sequence
<220> FEATURE:
<223> OTHER INFORMATION: synthetic polynucleotide

<400> SEQUENCE: 33
atcctctggc atgagatgtg catgaaggc ctggaagagg catctcgttt gtactttggg     60
gaaaggaacg tgaaaggcat gtttgaggtg ctggagccct gcatgctat gatggaacgg   120 ggcccccaga ctctgaagga acatcccttt aatcaggcct atggtcgaga tttaatggag   180
gcccaagagt ggtgcaggaa gtacatgaaa tcagggaatg tcaaggacct cctccaagcc   240
tgggacctct attatcatgt gttccgacga atctcaaag                         279
```

<210> SEQ ID NO 34
<211> LENGTH: 93
<212> TYPE: PRT
<213> ORGANISM: Artificial Sequence
<220> FEATURE:
<223> OTHER INFORMATION: synthetic polypeptide

<400> SEQUENCE: 34

```
Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser Lys
                85                  90
```

<210> SEQ ID NO 35
<211> LENGTH: 1857
<212> TYPE: DNA
<213> ORGANISM: Artificial Sequence
<220> FEATURE:
<223> OTHER INFORMATION: synthetic polynucleotide

<400> SEQUENCE: 35

| | | |
|---|---|---|
| atgccagacc ccgcggcgca tctgcccttc ttctacggca gcatctcgcg tgccgaggcc | 60 |
| gaggagcacc tgaagctggc gggcatggcg acgggctct tcctgctgcg ccagtgcctg | 120 |
| cgctcgctgg gcggctatgt gctgtcgctc gtgcacgatg tgcgcttcca ccactttccc | 180 |
| atcgagcgcc agctcaacgg cacctacgcc attgccggcg gcaaagcgca ctgtggaccg | 240 |
| gcagagctct gcgagttcta ctcgcgcgac cccgacgggc tgccctgcaa cctgcgcaag | 300 |
| ccgtgcaacc ggccgtcggg cctcgagccg cagccggggg tcttcgactg cctgcgagac | 360 |
| gccatggtgc gtgactacgt gcgccagacg tggaagctgg agggcgaggc cctggagcag | 420 |
| gccatcatca gccaggcccc gcaagtggag aagctcattg ctacgacggc ccacgagcgg | 480 |
| atgcccctggt accacagcag cctgacgcgt gaggaggccg agcgcaaact ttactctggg | 540 |
| gcgcagaccg acggcaagtt cctgctgagg ccgcggaagg agcagggcac atacgccctg | 600 |
| tccctcatct atgggaagac ggtgtaccac tacctcatca gccaagacaa ggcgggcaag | 660 |
| tactgcattc ccgagggcac caagtttgac acgctctggc agctggtgga gtatctgaag | 720 |
| ctgaaggcgg acgggctcat ctactgcctg aaggaggcct gccccaacag cagtgccagc | 780 |
| aacgcctcag ggctgctgc tcccacactc ccagcccacc catccacgtt gactcatcct | 840 |
| cagagacgaa tcgacacccct caactcagat ggatacaccc ctgagccagc acgcataacg | 900 |
| tccccagaca aaccgcggcc gatgcccatg gacacgagcg tgtatgagag ccctacagc | 960 |
| gacccagagg agctcaagga caagaagctc ttcctgaagc gcgataaccct cctcatagct | 1020 |
| gacattgaac ttggctgcgg caactttggc tcagtgcgcc agggcgtgta ccgcatgcgc | 1080 |
| aagaagcaga tcgacgtggc catcaaggtg ctgaagcagg gcacggagaa ggcagacacg | 1140 |
| gaagagatga tgcgcgaggc gcagatcatg caccagctgg acaaccccta catcgtgcgg | 1200 |

```
ctcattggcg tctgccaggc cgaggccctc atgctggtca tggagatggc tgggggcggg    1260
ccgctgcaca agttcctggt cggcaagagg gaggagatcc ctgtgagcaa tgtggccgag    1320
ctgctgcacc aggtgtccat ggggatgaag tacctggagg agaagaactt tgtgcaccgt    1380
gacctggcgg cccgcaacgt cctgctggtt aaccggcact acgccaagat cagcgacttt    1440
ggcctctcca agcactgggt gccgacgac agctactaca ctgcccgctc agcagggaag    1500
tggccgctca gtggtacgc acccgaatgc atcaacttcc gcaagttctc cagccgcagc    1560
gatgtctgga gctatggggt caccatgtgg gaggccttgt cctacggcca gaagccctac    1620
aagaagatga agggccggaa ggtcatggcc ttcatcgagc agggcaagcg gatggagtgc    1680
ccaccagagt gtccacccga actgtacgca ctcatgagtg actgctggat ctacaagtgg    1740
gaggatcgcc ccgacttcct gaccgtggag cagcgcatgc gagcctgtta ctacagcctg    1800
gccagcaagg tggaagggcc cccaggcagc acacagaagg ctgaggctgc ctgtgcc      1857
```

<210> SEQ ID NO 36
<211> LENGTH: 619
<212> TYPE: PRT
<213> ORGANISM: Artificial Sequence
<220> FEATURE:
<223> OTHER INFORMATION: synthetic polypeptide

<400> SEQUENCE: 36

```
Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255
```

```
Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 37
<211> LENGTH: 5
<212> TYPE: PRT
<213> ORGANISM: Artificial Sequence
<220> FEATURE:
<223> OTHER INFORMATION: synthetic polypeptide
<220> FEATURE:
<221> NAME/KEY: REPEAT
```

-continued

```
<222> LOCATION: (1)..(5)
<223> OTHER INFORMATION: the amino acids in this region can be repeated
      n times, where n is an integer of at least one

<400> SEQUENCE: 37

Gly Ser Gly Gly Ser
1               5

<210> SEQ ID NO 38
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: REPEAT
<222> LOCATION: (1)..(4)
<223> OTHER INFORMATION: the amino acids in this region can be repeated
      n times, where n is an integer of at least one

<400> SEQUENCE: 38

Gly Gly Gly Ser
1

<210> SEQ ID NO 39
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 39

Gly Gly Ser Gly
1

<210> SEQ ID NO 40
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 40

Gly Gly Ser Gly Gly
1               5

<210> SEQ ID NO 41
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 41

Gly Ser Gly Ser Gly
1               5

<210> SEQ ID NO 42
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 42

Gly Ser Gly Gly Gly
1               5
```

```
<210> SEQ ID NO 43
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 43

Gly Gly Gly Ser Gly
1               5

<210> SEQ ID NO 44
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 44

Gly Ser Ser Ser Gly
1               5

<210> SEQ ID NO 45
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 45

Asp Lys Thr His Thr
1               5

<210> SEQ ID NO 46
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 46

Cys Pro Pro Cys
1

<210> SEQ ID NO 47
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 47

Cys Pro Glu Pro Lys Ser Cys Asp Thr Pro Pro Pro Cys Pro Arg
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 48

Glu Leu Lys Thr Pro Leu Gly Asp Thr Thr His Thr
1               5                   10
```

```
<210> SEQ ID NO 49
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 49

Lys Ser Cys Asp Lys Thr His Thr Cys Pro
1               5                   10

<210> SEQ ID NO 50
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 50

Lys Cys Cys Val Asp Cys Pro
1               5

<210> SEQ ID NO 51
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 51

Lys Tyr Gly Pro Pro Cys Pro
1               5

<210> SEQ ID NO 52
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 52

Glu Pro Lys Ser Cys Asp Lys Thr His Thr Cys Pro Pro Cys Pro
1               5                   10                  15

<210> SEQ ID NO 53
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 53

Glu Arg Lys Cys Cys Val Glu Cys Pro Pro Cys Pro
1               5                   10

<210> SEQ ID NO 54
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 54

Glu Leu Lys Thr Pro Leu Gly Asp Thr Thr His Thr Cys Pro Arg Cys
1               5                   10                  15
Pro
```

<210> SEQ ID NO 55
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 55

Ser Pro Asn Met Val Pro His Ala His His Ala Gln
1               5                   10

<210> SEQ ID NO 56
<211> LENGTH: 45
<212> TYPE: PRT
<213> ORGANISM: Artificial Sequence
<220> FEATURE:
<223> OTHER INFORMATION: synthetic polypeptide

<400> SEQUENCE: 56

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 57
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 57

Leu Gly Leu Leu Val Ala Gly Val Leu Val Leu Leu Val Ser Leu Gly
1               5                   10                  15

Val Ala Ile His Leu Cys Cys
            20

<210> SEQ ID NO 58
<211> LENGTH: 25
<212> TYPE: PRT
<213> ORGANISM: Artificial Sequence
<220> FEATURE:
<223> OTHER INFORMATION: synthetic polypeptide

<400> SEQUENCE: 58

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 59
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 59

Leu Cys Tyr Leu Leu Asp Gly Ile Leu Phe Ile Tyr Gly Val Ile Leu
1               5                   10                  15

Thr Ala Leu Phe Leu Arg Val
            20

```
<210> SEQ ID NO 60
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 60

Trp Val Leu Val Val Val Gly Gly Val Leu Ala Cys Tyr Ser Leu Leu
1               5                   10                  15

Val Thr Val Ala Phe Ile Ile Phe Trp Val
            20                  25

<210> SEQ ID NO 61
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 61

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 62
<211> LENGTH: 24
<212> TYPE: PRT
<213> ORGANISM: Artificial Sequence
<220> FEATURE:
<223> OTHER INFORMATION: synthetic polypeptide

<400> SEQUENCE: 62

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 63
<211> LENGTH: 44
<212> TYPE: PRT
<213> ORGANISM: Artificial Sequence
<220> FEATURE:
<223> OTHER INFORMATION: synthetic polypeptide

<400> SEQUENCE: 63

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40

<210> SEQ ID NO 64
<211> LENGTH: 35
<212> TYPE: PRT
<213> ORGANISM: Artificial Sequence
<220> FEATURE:
<223> OTHER INFORMATION: synthetic polypeptide

<400> SEQUENCE: 64

Thr Lys Lys Lys Tyr Ser Ser Ser Val His Asp Pro Asn Gly Glu Tyr
```

```
1               5                   10                  15
Met Phe Met Arg Ala Val Asn Thr Ala Lys Lys Ser Arg Leu Thr Asp
                20                  25                  30
Val Thr Leu
        35
```

<210> SEQ ID NO 65
<211> LENGTH: 37
<212> TYPE: PRT
<213> ORGANISM: Artificial Sequence
<220> FEATURE:
<223> OTHER INFORMATION: synthetic polypeptide

<400> SEQUENCE: 65

```
Arg Arg Asp Gln Arg Leu Pro Pro Asp Ala His Lys Pro Gly Gly
1               5                   10                  15

Gly Ser Phe Arg Thr Pro Ile Gln Glu Gln Ala Asp Ala His Ser
                20                  25                  30

Thr Leu Ala Lys Ile
        35
```

<210> SEQ ID NO 66
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 66

```
Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
                20                  25                  30

Thr Glu Ala Ser Thr Arg Gln Asn Ser Gln Val Leu Leu Ser Glu Thr
            35                  40                  45

Gly Ile Tyr Asp Asn Asp Pro Asp Leu Cys Phe Arg Met Gln Glu Gly
        50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
                100                 105                 110

Arg Ser
```

<210> SEQ ID NO 67
<211> LENGTH: 49
<212> TYPE: PRT
<213> ORGANISM: Artificial Sequence
<220> FEATURE:
<223> OTHER INFORMATION: synthetic polypeptide

<400> SEQUENCE: 67

```
His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
                20                  25                  30

Thr Ile Pro Ile Gln Glu Asp Tyr Arg Lys Pro Glu Pro Ala Cys Ser
            35                  40                  45
```

Pro

<210> SEQ ID NO 68
<211> LENGTH: 187
<212> TYPE: PRT
<213> ORGANISM: Artificial Sequence
<220> FEATURE:
<223> OTHER INFORMATION: synthetic polypeptide

<400> SEQUENCE: 68

Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
    50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
    130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Gly Lys
                165                 170                 175

Glu Asp Pro Leu Pro Thr Ala Ala Ser Gly Lys
            180                 185

<210> SEQ ID NO 69
<211> LENGTH: 54
<212> TYPE: PRT
<213> ORGANISM: Artificial Sequence
<220> FEATURE:
<223> OTHER INFORMATION: synthetic polypeptide

<400> SEQUENCE: 69

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50

<210> SEQ ID NO 70
<211> LENGTH: 60
<212> TYPE: PRT
<213> ORGANISM: Artificial Sequence
<220> FEATURE:
<223> OTHER INFORMATION: synthetic polypeptide

<400> SEQUENCE: 70

```
Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
                20                  25                  30

Glu Ala Leu Gln Ala Pro Pro Asp Val Thr Thr Val Ala Val Glu Glu
                35                  40                  45

Thr Ile Pro Ser Phe Thr Gly Arg Ser Pro Asn His
                50                  55                  60
```

<210> SEQ ID NO 71
<211> LENGTH: 292
<212> TYPE: PRT
<213> ORGANISM: Artificial Sequence
<220> FEATURE:
<223> OTHER INFORMATION: synthetic polypeptide

<400> SEQUENCE: 71

```
Leu Glu Glu Ser Val Ala Leu Arg Ile Ile Thr Glu Gly Ala Ser Ile
1               5                   10                  15

Leu Arg Gln Glu Lys Asn Leu Leu Asp Ile Asp Ala Pro Val Thr Val
                20                  25                  30

Cys Gly Asp Ile His Gly Gln Phe Phe Asp Leu Met Lys Leu Phe Glu
                35                  40                  45

Val Gly Gly Ser Pro Ala Asn Thr Arg Tyr Leu Phe Leu Gly Asp Tyr
                50                  55                  60

Val Asp Arg Gly Tyr Phe Ser Ile Glu Cys Val Leu Tyr Leu Trp Ala
65                  70                  75                  80

Leu Lys Ile Leu Tyr Pro Lys Thr Leu Phe Leu Leu Arg Gly Asn His
                85                  90                  95

Glu Cys Arg His Leu Thr Glu Tyr Phe Thr Phe Lys Gln Glu Cys Lys
                100                 105                 110

Ile Lys Tyr Ser Glu Arg Val Tyr Asp Ala Cys Met Asp Ala Phe Asp
                115                 120                 125

Cys Leu Pro Leu Ala Ala Leu Met Asn Gln Gln Phe Leu Cys Val His
                130                 135                 140

Gly Gly Leu Ser Pro Glu Ile Asn Thr Leu Asp Asp Ile Arg Lys Leu
145                 150                 155                 160

Asp Arg Phe Lys Glu Pro Pro Ala Tyr Gly Pro Met Cys Asp Ile Leu
                165                 170                 175

Trp Ser Asp Pro Leu Glu Asp Phe Gly Asn Glu Lys Thr Gln Glu His
                180                 185                 190

Phe Thr His Asn Thr Val Arg Gly Cys Ser Tyr Phe Tyr Ser Tyr Pro
                195                 200                 205

Ala Val Cys Glu Phe Leu Gln His Asn Asn Leu Leu Ser Ile Leu Arg
                210                 215                 220

Ala His Glu Ala Gln Asp Ala Gly Tyr Arg Met Tyr Arg Lys Ser Gln
225                 230                 235                 240

Thr Thr Gly Phe Pro Ser Leu Ile Thr Ile Phe Ser Ala Pro Asn Tyr
                245                 250                 255

Leu Asp Val Tyr Asn Asn Lys Ala Ala Val Leu Lys Tyr Glu Asn Asn
                260                 265                 270

Val Met Asn Ile Arg Gln Phe Asn Cys Ser Pro His Pro Tyr Trp Leu
                275                 280                 285

Pro Asn Phe Met
                290
```

<210> SEQ ID NO 72
<211> LENGTH: 165
<212> TYPE: PRT
<213> ORGANISM: Artificial Sequence
<220> FEATURE:
<223> OTHER INFORMATION: synthetic polypeptide

<400> SEQUENCE: 72

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
                20                  25                  30

Ala Glu Asn Phe Arg Ala Leu Ser Thr Gly Glu Lys Gly Phe Gly Tyr
            35                  40                  45

Lys Gly Ser Cys Phe His Arg Ile Ile Pro Gly Phe Met Cys Gln Gly
        50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 73
<211> LENGTH: 804
<212> TYPE: PRT
<213> ORGANISM: Artificial Sequence
<220> FEATURE:
<223> OTHER INFORMATION: synthetic polypeptide

<400> SEQUENCE: 73

Met Ser Asn Ser Tyr Asp Ser Ser Ile Lys Val Leu Lys Gly Leu
1               5                   10                  15

Asp Ala Val Arg Lys Arg Pro Gly Met Tyr Ile Gly Asp Thr Asp Asp
                20                  25                  30

Gly Thr Gly Leu His His Met Val Phe Glu Val Val Asp Asn Ala Ile
            35                  40                  45

Asp Glu Ala Leu Ala Gly His Cys Lys Glu Ile Ile Val Thr Ile His
        50                  55                  60

Ala Asp Asn Ser Val Ser Val Gln Asp Gly Arg Gly Ile Pro Thr
65                  70                  75                  80

Gly Ile His Pro Glu Glu Gly Val Ser Ala Ala Glu Val Ile Met Thr
                85                  90                  95

Val Leu His Ala Gly Gly Lys Phe Asp Asp Asn Ser Tyr Lys Val Ser
            100                 105                 110

Gly Gly Leu His Gly Val Gly Val Ser Val Val Asn Ala Leu Ser Gln
        115                 120                 125

Lys Leu Glu Leu Val Ile Gln Arg Glu Gly Lys Ile His Arg Gln Ile

```
                130                 135                 140
Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
                180                 185                 190

Glu Leu Ser Phe Leu Asn Ser Gly Val Ser Ile Arg Leu Arg Asp Lys
                195                 200                 205

Arg Asp Gly Lys Glu Asp His Phe His Tyr Glu Gly Gly Ile Lys Ala
            210                 215                 220

Phe Val Glu Tyr Leu Asn Lys Asn Lys Thr Pro Ile His Pro Asn Ile
225                 230                 235                 240

Phe Tyr Phe Ser Thr Glu Lys Asp Gly Ile Gly Val Glu Val Ala Leu
                245                 250                 255

Gln Trp Asn Asp Gly Phe Gln Glu Asn Ile Tyr Cys Phe Thr Asn Asn
            260                 265                 270

Ile Pro Gln Arg Asp Gly Gly Thr His Leu Ala Gly Phe Arg Ala Ala
            275                 280                 285

Met Thr Arg Thr Leu Asn Ala Tyr Met Asp Lys Glu Gly Tyr Ser Lys
            290                 295                 300

Lys Ala Lys Val Ser Ala Thr Gly Asp Asp Ala Arg Glu Gly Leu Ile
305                 310                 315                 320

Ala Val Val Ser Val Lys Val Pro Asp Pro Lys Phe Ser Ser Gln Thr
                325                 330                 335

Lys Asp Lys Leu Val Ser Ser Glu Val Lys Ser Ala Val Glu Gln Gln
            340                 345                 350

Met Asn Glu Leu Leu Ala Glu Tyr Leu Leu Glu Asn Pro Thr Asp Ala
            355                 360                 365

Lys Ile Val Val Gly Lys Ile Ile Asp Ala Ala Arg Ala Arg Glu Ala
            370                 375                 380

Ala Arg Arg Ala Arg Glu Met Thr Arg Arg Lys Gly Ala Leu Asp Leu
385                 390                 395                 400

Ala Gly Leu Pro Gly Lys Leu Ala Asp Cys Gln Glu Arg Asp Pro Ala
                405                 410                 415

Leu Ser Glu Leu Tyr Leu Val Gly Asp Ser Ala Gly Gly Ser Ala
            420                 425                 430

Lys Gln Gly Arg Asn Arg Lys Asn Gln Ala Ile Leu Pro Leu Lys Gly
            435                 440                 445

Lys Ile Leu Asn Val Glu Lys Ala Arg Phe Asp Lys Met Leu Ser Ser
            450                 455                 460

Gln Glu Val Ala Thr Leu Ile Thr Ala Leu Gly Cys Gly Ile Gly Arg
465                 470                 475                 480

Asp Glu Tyr Asn Pro Asp Lys Leu Arg Tyr His Ser Ile Ile Met
                485                 490                 495

Thr Asp Ala Asp Val Asp Gly Ser His Ile Arg Thr Leu Leu Leu Thr
                500                 505                 510

Phe Phe Tyr Arg Gln Met Pro Glu Ile Val Glu Arg Gly His Val Tyr
                515                 520                 525

Ile Ala Gln Pro Pro Leu Tyr Lys Val Lys Lys Gly Lys Gln Glu Gln
            530                 535                 540

Tyr Ile Lys Asp Asp Glu Ala Met Asp Gln Tyr Gln Ile Ser Ile Ala
545                 550                 555                 560
```

```
Leu Asp Gly Ala Thr Leu His Thr Asn Ala Ser Ala Pro Ala Leu Ala
                565                 570                 575

Gly Glu Ala Leu Glu Lys Leu Val Ser Glu Tyr Asn Ala Thr Gln Lys
            580                 585                 590

Met Ile Asn Arg Met Glu Arg Arg Tyr Pro Lys Ala Met Leu Lys Glu
        595                 600                 605

Leu Ile Tyr Gln Pro Thr Leu Thr Glu Ala Asp Leu Ser Asp Glu Gln
    610                 615                 620

Thr Val Thr Arg Trp Val Asn Ala Leu Val Ser Glu Leu Asn Asp Lys
625                 630                 635                 640

Glu Gln His Gly Ser Gln Trp Lys Phe Asp Val His Thr Asn Ala Glu
                645                 650                 655

Gln Asn Leu Phe Glu Pro Ile Val Arg Val Arg Thr His Gly Val Asp
            660                 665                 670

Thr Asp Tyr Pro Leu Asp His Glu Phe Ile Thr Gly Gly Glu Tyr Arg
        675                 680                 685

Arg Ile Cys Thr Leu Gly Glu Lys Leu Arg Gly Leu Leu Glu Glu Asp
    690                 695                 700

Ala Phe Ile Glu Arg Gly Glu Arg Arg Gln Pro Val Ala Ser Phe Glu
705                 710                 715                 720

Gln Ala Leu Asp Trp Leu Val Lys Glu Ser Arg Arg Gly Leu Ser Ile
                725                 730                 735

Gln Arg Tyr Lys Gly Leu Gly Glu Met Asn Pro Glu Gln Leu Trp Glu
            740                 745                 750

Thr Thr Met Asp Pro Glu Ser Arg Arg Met Leu Arg Val Thr Val Lys
        755                 760                 765

Asp Ala Ile Ala Ala Asp Gln Leu Phe Thr Thr Leu Met Gly Asp Ala
    770                 775                 780

Val Glu Pro Arg Arg Ala Phe Ile Glu Glu Asn Ala Leu Lys Ala Ala
785                 790                 795                 800

Asn Ile Asp Ile

<210> SEQ ID NO 74
<211> LENGTH: 187
<212> TYPE: PRT
<213> ORGANISM: Artificial Sequence
<220> FEATURE:
<223> OTHER INFORMATION: synthetic polypeptide

<400> SEQUENCE: 74

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110
```

```
Val Trp Ile Val Gly Gly Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Lys Gly Ile
                165                 170                 175

Lys Tyr Lys Phe Glu Val Tyr Glu Lys Asn Asp
            180                 185

<210> SEQ ID NO 75
<211> LENGTH: 111
<212> TYPE: PRT
<213> ORGANISM: Artificial Sequence
<220> FEATURE:
<223> OTHER INFORMATION: synthetic polypeptide

<400> SEQUENCE: 75

Met Ala Ser Arg Gly Val Gln Val Glu Thr Ile Ser Pro Gly Asp Gly
1               5                   10                  15

Arg Thr Phe Pro Lys Arg Gly Gln Thr Cys Val Val His Tyr Thr Gly
            20                  25                  30

Met Leu Glu Asp Gly Lys Lys Val Asp Ser Ser Arg Asp Arg Asn Lys
        35                  40                  45

Pro Phe Lys Phe Met Leu Gly Lys Gln Glu Val Ile Arg Gly Trp Glu
    50                  55                  60

Glu Gly Val Ala Gln Met Ser Val Gly Gln Arg Ala Lys Leu Thr Ile
65                  70                  75                  80

Ser Pro Asp Tyr Ala Tyr Gly Ala Thr Gly His Pro Gly Ile Ile Pro
                85                  90                  95

Pro His Ala Thr Leu Val Phe Asp Val Glu Leu Leu Lys Leu Glu
            100                 105                 110

<210> SEQ ID NO 76
<211> LENGTH: 183
<212> TYPE: PRT
<213> ORGANISM: Artificial Sequence
<220> FEATURE:
<223> OTHER INFORMATION: synthetic polypeptide

<400> SEQUENCE: 76

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
            20                  25                  30

Lys His Ile Lys Ala Pro Leu His Leu Val Trp Ser Ile Val Arg Arg
        35                  40                  45

Phe Asp Glu Pro Gln Lys Tyr Lys Pro Phe Ile Ser Arg Cys Val Val
    50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
        115                 120                 125
```

Gly Lys Thr Gly Thr Leu Ala Ile Glu Ser Phe Val Val Asp Val Pro
    130                 135                 140

Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180

<210> SEQ ID NO 77
<211> LENGTH: 161
<212> TYPE: PRT
<213> ORGANISM: Artificial Sequence
<220> FEATURE:
<223> OTHER INFORMATION: synthetic polypeptide

<400> SEQUENCE: 77

Met Glu Thr Ser Gln Lys Tyr His Thr Cys Gly Ser Thr Leu Val Gln
1               5                   10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
            35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
            115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160

Leu

<210> SEQ ID NO 78
<211> LENGTH: 159
<212> TYPE: PRT
<213> ORGANISM: Artificial Sequence
<220> FEATURE:
<223> OTHER INFORMATION: synthetic polypeptide

<400> SEQUENCE: 78

Met Lys Thr Ser Gln Glu Gln His Val Cys Gly Ser Thr Val Val Gln
1               5                   10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
            35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

```
Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
                115                 120                 125

Thr Glu Glu Glu Thr Thr Leu Phe Ala Asp Thr Ile Val Gly Cys Asn
            130                 135                 140

Leu Arg Ser Leu Ala Lys Leu Ser Glu Lys Met Met Glu Leu Thr
145                 150                 155
```

<210> SEQ ID NO 79
<211> LENGTH: 164
<212> TYPE: PRT
<213> ORGANISM: Artificial Sequence
<220> FEATURE:
<223> OTHER INFORMATION: synthetic polypeptide

<400> SEQUENCE: 79

```
Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
                20                  25                  30

Lys Pro Gln Ala Tyr Gln Arg Phe Val Lys Ser Cys Thr Met Arg Ser
            35                  40                  45

Gly Gly Gly Gly Gly Lys Gly Gly Glu Gly Lys Gly Ser Val Arg Asp
        50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys Lys Thr Val Val Val Glu Ser Tyr Val
        115                 120                 125

Val Asp Val Pro Glu Gly Thr Ser Glu Glu Asp Thr Ile Phe Phe Val
    130                 135                 140

Asp Asn Ile Ile Arg Tyr Asn Leu Thr Ser Leu Ala Lys Leu Thr Lys
145                 150                 155                 160

Lys Met Met Lys
```

<210> SEQ ID NO 80
<211> LENGTH: 221
<212> TYPE: PRT
<213> ORGANISM: Artificial Sequence
<220> FEATURE:
<223> OTHER INFORMATION: synthetic polypeptide

<400> SEQUENCE: 80

```
Met Ala Asn Ser Glu Ser Ser Ser Pro Val Asn Glu Glu Glu Asn
1               5                   10                  15

Ser Gln Arg Ile Ser Thr Leu His His Gln Thr Met Pro Ser Asp Leu
                20                  25                  30

Thr Gln Asp Glu Phe Thr Gln Leu Ser Gln Ser Ile Ala Glu Phe His
            35                  40                  45

Thr Tyr Gln Leu Gly Asn Gly Arg Cys Ser Ser Leu Leu Ala Gln Arg
        50                  55                  60
```

```
Ile His Ala Pro Pro Glu Thr Val Trp Ser Val Val Arg Arg Phe Asp
 65                  70                  75                  80

Arg Pro Gln Ile Tyr Lys His Phe Ile Lys Ser Cys Asn Val Ser Glu
                 85                  90                  95

Asp Phe Glu Met Arg Val Gly Cys Thr Arg Asp Val Asn Val Ile Ser
            100                 105                 110

Gly Leu Pro Ala Asn Thr Ser Arg Glu Arg Leu Asp Leu Leu Asp Asp
        115                 120                 125

Asp Arg Arg Val Thr Gly Phe Ser Ile Thr Gly Gly Glu His Arg Leu
130                 135                 140

Arg Asn Tyr Lys Ser Val Thr Thr Val His Arg Phe Glu Lys Glu Glu
145                 150                 155                 160

Glu Glu Glu Arg Ile Trp Thr Val Val Leu Glu Ser Tyr Val Val Asp
                165                 170                 175

Val Pro Glu Gly Asn Ser Glu Glu Asp Thr Arg Leu Phe Ala Asp Thr
            180                 185                 190

Val Ile Arg Leu Asn Leu Gln Lys Leu Ala Ser Ile Thr Glu Ala Met
        195                 200                 205

Asn Arg Asn Asn Asn Asn Asn Asn Ser Ser Gln Val Arg
210                 215                 220
```

```
<210> SEQ ID NO 81
<211> LENGTH: 190
<212> TYPE: PRT
<213> ORGANISM: Artificial Sequence
<220> FEATURE:
<223> OTHER INFORMATION: synthetic polypeptide

<400> SEQUENCE: 81

Met Ser Ser Ser Pro Ala Val Lys Gly Leu Thr Asp Glu Glu Gln Lys
  1               5                  10                  15

Thr Leu Glu Pro Val Ile Lys Thr Tyr His Gln Phe Glu Pro Asp Pro
             20                  25                  30

Thr Thr Cys Thr Ser Leu Ile Thr Gln Arg Ile His Ala Pro Ala Ser
         35                  40                  45

Val Val Trp Pro Leu Ile Arg Arg Phe Asp Asn Pro Glu Arg Tyr Lys
     50                  55                  60

His Phe Val Lys Arg Cys Arg Leu Ile Ser Gly Asp Gly Asp Val Gly
 65                  70                  75                  80

Ser Val Arg Glu Val Thr Val Ile Ser Gly Leu Pro Ala Ser Thr Ser
                 85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190
```

```
<210> SEQ ID NO 82
```

```
<211> LENGTH: 209
<212> TYPE: PRT
<213> ORGANISM: Artificial Sequence
<220> FEATURE:
<223> OTHER INFORMATION: synthetic polypeptide

<400> SEQUENCE: 82

Met Asn Leu Ala Pro Ile His Asp Pro Ser Ser Ser Thr Thr Thr
1               5                   10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
            35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Ser Gly Leu Pro
            100                 105                 110

Ala Ser Thr Ser Val Glu Ile Leu Glu Val Leu Asp Glu Glu Lys Arg
            115                 120                 125

Ile Leu Ser Phe Arg Val Leu Gly Gly Glu His Arg Leu Asn Asn Tyr
            130                 135                 140

Arg Ser Val Thr Ser Val Asn Glu Phe Val Val Leu Glu Lys Asp Lys
145                 150                 155                 160

Lys Lys Arg Val Tyr Ser Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
            195                 200                 205

Thr

<210> SEQ ID NO 83
<211> LENGTH: 207
<212> TYPE: PRT
<213> ORGANISM: Artificial Sequence
<220> FEATURE:
<223> OTHER INFORMATION: synthetic polypeptide

<400> SEQUENCE: 83

Met Leu Ala Val His Arg Pro Ser Ser Ala Val Ser Asp Gly Asp Ser
1               5                   10                  15

Val Gln Ile Pro Met Met Ile Ala Ser Phe Gln Lys Arg Phe Pro Ser
            20                  25                  30

Leu Ser Arg Asp Ser Thr Ala Ala Arg Phe His Thr His Glu Val Gly
            35                  40                  45

Pro Asn Gln Cys Cys Ser Ala Val Ile Gln Glu Ile Ser Ala Pro Ile
    50                  55                  60

Ser Thr Val Trp Ser Val Val Arg Arg Phe Asp Asn Pro Gln Ala Tyr
65                  70                  75                  80

Lys His Phe Leu Lys Ser Cys Ser Val Ile Gly Gly Asp Gly Asp Asn
                85                  90                  95

Val Gly Ser Leu Arg Gln Val His Val Val Ser Gly Leu Pro Ala Ala
            100                 105                 110
```

```
Ser Ser Thr Glu Arg Leu Asp Ile Leu Asp Asp Glu Arg His Val Ile
        115                 120                 125

Ser Phe Ser Val Val Gly Gly Asp His Arg Leu Ser Asn Tyr Arg Ser
130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
                180                 185                 190

Ile Ala Glu Asn Thr Ala Ala Glu Ser Lys Lys Lys Met Ser Leu
        195                 200                 205

<210> SEQ ID NO 84
<211> LENGTH: 203
<212> TYPE: PRT
<213> ORGANISM: Artificial Sequence
<220> FEATURE:
<223> OTHER INFORMATION: synthetic polypeptide

<400> SEQUENCE: 84

Met Arg Ser Pro Val Gln Leu Gln His Gly Ser Asp Ala Thr Asn Gly
1               5                   10                  15

Phe His Thr Leu Gln Pro His Asp Gln Thr Asp Gly Pro Ile Lys Arg
            20                  25                  30

Val Cys Leu Thr Arg Gly Met His Val Pro Glu His Val Ala Met His
        35                  40                  45

His Thr His Asp Val Gly Pro Asp Gln Cys Cys Ser Ser Val Val Gln
50                  55                  60

Met Ile His Ala Pro Pro Glu Ser Val Trp Ala Leu Val Arg Arg Phe
65                  70                  75                  80

Asp Asn Pro Lys Val Tyr Lys Asn Phe Ile Arg Gln Cys Arg Ile Val
                85                  90                  95

Gln Gly Asp Gly Leu His Val Gly Asp Leu Arg Glu Val Met Val Val
            100                 105                 110

Ser Gly Leu Pro Ala Val Ser Ser Thr Glu Arg Leu Glu Ile Leu Asp
        115                 120                 125

Glu Glu Arg His Val Ile Ser Phe Ser Val Val Gly Gly Asp His Arg
    130                 135                 140

Leu Lys Asn Tyr Arg Ser Val Thr Thr Leu His Ala Ser Asp Asp Glu
145                 150                 155                 160

Gly Thr Val Val Val Glu Ser Tyr Ile Val Asp Val Pro Pro Gly Asn
                165                 170                 175

Thr Glu Glu Glu Thr Leu Ser Phe Val Asp Thr Ile Val Arg Cys Asn
            180                 185                 190

Leu Gln Ser Leu Ala Arg Ser Thr Asn Arg Gln
        195                 200

<210> SEQ ID NO 85
<211> LENGTH: 215
<212> TYPE: PRT
<213> ORGANISM: Artificial Sequence
<220> FEATURE:
<223> OTHER INFORMATION: synthetic polypeptide

<400> SEQUENCE: 85

Met Pro Thr Ser Ile Gln Phe Gln Arg Ser Ser Thr Ala Ala Glu Ala
```

```
                1               5                    10                   15
        Ala Asn Ala Thr Val Arg Asn Tyr Pro His His His Gln Lys Gln Val
                        20                  25                  30
        Gln Lys Val Ser Leu Thr Arg Gly Met Ala Asp Val Pro Glu His Val
                        35                  40                  45
        Glu Leu Ser His Thr His Val Val Gly Pro Ser Gln Cys Phe Ser Val
                    50                  55                  60
        Val Val Gln Asp Val Glu Ala Pro Val Ser Thr Val Trp Ser Ile Leu
        65                  70                  75                  80
        Ser Arg Phe Glu His Pro Gln Ala Tyr Lys His Phe Val Lys Ser Cys
                            85                  90                  95
        His Val Val Ile Gly Asp Gly Arg Glu Val Gly Ser Val Arg Glu Val
                        100                 105                 110
        Arg Val Val Ser Gly Leu Pro Ala Ala Phe Ser Leu Glu Arg Leu Glu
                        115                 120                 125
        Ile Met Asp Asp Asp Arg His Val Ile Ser Phe Ser Val Val Gly Gly
                    130                 135                 140
        Asp His Arg Leu Met Asn Tyr Lys Ser Val Thr Thr Val His Glu Ser
        145                 150                 155                 160
        Glu Glu Asp Ser Asp Gly Lys Lys Arg Thr Arg Val Val Glu Ser Tyr
                        165                 170                 175
        Val Val Asp Val Pro Ala Gly Asn Asp Lys Glu Glu Thr Cys Ser Phe
                        180                 185                 190
        Ala Asp Thr Ile Val Arg Cys Asn Leu Gln Ser Leu Ala Lys Leu Ala
                        195                 200                 205
        Glu Asn Thr Ser Lys Phe Ser
                        210                 215

<210> SEQ ID NO 86
<211> LENGTH: 211
<212> TYPE: PRT
<213> ORGANISM: Artificial Sequence
<220> FEATURE:
<223> OTHER INFORMATION: synthetic polypeptide

<400> SEQUENCE: 86

Met Glu Met Ile Gly Gly Asp Asp Thr Asp Thr Glu Met Tyr Gly Ala
        1                   5                   10                  15
        Leu Val Thr Ala Gln Ser Leu Arg Leu Arg His Leu His Cys Arg
                        20                  25                  30
        Glu Asn Gln Cys Thr Ser Val Leu Val Lys Tyr Ile Gln Ala Pro Val
                        35                  40                  45
        His Leu Val Trp Ser Leu Val Arg Arg Phe Asp Gln Pro Gln Lys Tyr
                    50                  55                  60
        Lys Pro Phe Ile Ser Arg Cys Thr Val Asn Gly Asp Pro Glu Ile Gly
        65                  70                  75                  80
        Cys Leu Arg Glu Val Asn Val Lys Ser Gly Leu Pro Ala Thr Thr Ser
                        85                  90                  95
        Thr Glu Arg Leu Glu Gln Leu Asp Asp Glu Glu His Ile Leu Gly Ile
                        100                 105                 110
        Asn Ile Ile Gly Gly Asp His Arg Leu Lys Asn Tyr Ser Ser Ile Leu
                        115                 120                 125
        Thr Val His Pro Glu Met Ile Asp Gly Arg Ser Gly Thr Met Val Met
                    130                 135                 140
        Glu Ser Phe Val Val Asp Val Pro Gln Gly Asn Thr Lys Asp Asp Thr
```

```
                145                 150                 155                 160
Cys Tyr Phe Val Glu Ser Leu Ile Lys Cys Asn Leu Lys Ser Leu Ala
                    165                 170                 175
Cys Val Ser Glu Arg Leu Ala Ala Gln Asp Ile Thr Asn Ser Ile Ala
                    180                 185                 190
Thr Phe Cys Asn Ala Ser Asn Gly Tyr Arg Glu Lys Asn His Thr Glu
                    195                 200                 205
Thr Asn Leu
    210

<210> SEQ ID NO 87
<211> LENGTH: 188
<212> TYPE: PRT
<213> ORGANISM: Artificial Sequence
<220> FEATURE:
<223> OTHER INFORMATION: synthetic polypeptide

<400> SEQUENCE: 87

Met Glu Ala Asn Gly Ile Glu Asn Leu Thr Asn Pro Asn Gln Glu Arg
1               5                   10                  15
Glu Phe Ile Arg Arg His His Lys His Glu Leu Val Asp Asn Gln Cys
                20                  25                  30
Ser Ser Thr Leu Val Lys His Ile Asn Ala Pro Val His Ile Val Trp
            35                  40                  45
Ser Leu Val Arg Arg Phe Asp Gln Pro Gln Lys Tyr Lys Pro Phe Ile
        50                  55                  60
Ser Arg Cys Val Val Lys Gly Asn Met Glu Ile Gly Thr Val Arg Glu
65                  70                  75                  80
Val Asp Val Lys Ser Gly Leu Pro Ala Thr Arg Ser Thr Glu Arg Leu
                85                  90                  95
Glu Leu Leu Asp Asp Asn Glu His Ile Leu Ser Ile Arg Ile Val Gly
                100                 105                 110
Gly Asp His Arg Leu Lys Asn Tyr Ser Ser Ile Ile Ser Leu His Pro
            115                 120                 125
Glu Thr Ile Glu Gly Arg Ile Gly Thr Leu Val Ile Glu Ser Phe Val
        130                 135                 140
Val Asp Val Pro Glu Gly Asn Thr Lys Asp Glu Thr Cys Tyr Phe Val
145                 150                 155                 160
Glu Ala Leu Ile Lys Cys Asn Leu Lys Ser Leu Ala Asp Ile Ser Glu
                165                 170                 175
Arg Leu Ala Val Gln Asp Thr Thr Glu Ser Arg Val
                180                 185

<210> SEQ ID NO 88
<211> LENGTH: 187
<212> TYPE: PRT
<213> ORGANISM: Artificial Sequence
<220> FEATURE:
<223> OTHER INFORMATION: synthetic polypeptide

<400> SEQUENCE: 88

Met Met Asp Gly Val Glu Gly Gly Thr Ala Met Tyr Gly Gly Leu Glu
1               5                   10                  15
Thr Val Gln Tyr Val Arg Thr His His Gln His Leu Cys Arg Glu Asn
                20                  25                  30
Gln Cys Thr Ser Ala Leu Val Lys His Ile Lys Ala Pro Leu His Leu
            35                  40                  45
```

```
Val Trp Ser Leu Val Arg Arg Phe Asp Gln Pro Gln Lys Tyr Lys Pro
 50                  55                  60

Phe Val Ser Arg Cys Thr Val Ile Gly Asp Pro Glu Ile Gly Ser Leu
 65                  70                  75                  80

Arg Glu Val Asn Val Lys Ser Gly Leu Pro Ala Thr Thr Ser Thr Glu
                 85                  90                  95

Arg Leu Glu Leu Leu Asp Asp Glu Glu His Ile Leu Gly Ile Lys Ile
             100                 105                 110

Ile Gly Gly Asp His Arg Leu Lys Asn Tyr Ser Ser Ile Leu Thr Val
         115                 120                 125

His Pro Glu Ile Ile Glu Gly Arg Ala Gly Thr Met Val Ile Glu Ser
 130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185
```

<210> SEQ ID NO 89
<211> LENGTH: 191
<212> TYPE: PRT
<213> ORGANISM: Artificial Sequence
<220> FEATURE:
<223> OTHER INFORMATION: synthetic polypeptide

<400> SEQUENCE: 89

```
Met Pro Ser Glu Leu Thr Pro Glu Glu Arg Ser Glu Leu Lys Asn Ser
 1               5                  10                  15

Ile Ala Glu Phe His Thr Tyr Gln Leu Asp Pro Gly Ser Cys Ser Ser
                 20                  25                  30

Leu His Ala Gln Arg Ile His Ala Pro Pro Glu Leu Val Trp Ser Ile
             35                  40                  45

Val Arg Arg Phe Asp Lys Pro Gln Thr Tyr Lys His Phe Ile Lys Ser
 50                  55                  60

Cys Ser Val Glu Gln Asn Phe Glu Met Arg Val Gly Cys Thr Arg Asp
 65                  70                  75                  80

Val Ile Val Ile Ser Gly Leu Pro Ala Asn Thr Ser Thr Glu Arg Leu
                 85                  90                  95

Asp Ile Leu Asp Asp Glu Arg Arg Val Thr Gly Phe Ser Ile Ile Gly
             100                 105                 110

Gly Glu His Arg Leu Thr Asn Tyr Lys Ser Val Thr Thr Val His Arg
         115                 120                 125

Phe Glu Lys Glu Asn Arg Ile Trp Thr Val Val Leu Glu Ser Tyr Val
 130                 135                 140

Val Asp Met Pro Glu Gly Asn Ser Glu Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190
```

<210> SEQ ID NO 90
<211> LENGTH: 434
<212> TYPE: PRT
<213> ORGANISM: Artificial Sequence
<220> FEATURE:

<223> OTHER INFORMATION: synthetic polypeptide

<400> SEQUENCE: 90

Met Glu Glu Val Ser Pro Ala Ile Ala Gly Pro Phe Arg Pro Phe Ser
1               5                   10                  15

Glu Thr Gln Met Asp Phe Thr Gly Ile Arg Leu Gly Lys Gly Tyr Cys
            20                  25                  30

Asn Asn Gln Tyr Ser Asn Gln Asp Ser Glu Asn Gly Asp Leu Met Val
        35                  40                  45

Ser Leu Pro Glu Thr Ser Ser Cys Ser Val Ser Gly Ser His Gly Ser
    50                  55                  60

Glu Ser Arg Lys Val Leu Ile Ser Arg Ile Asn Ser Pro Asn Leu Asn
65                  70                  75                  80

Met Lys Glu Ser Ala Ala Ala Asp Ile Val Val Asp Ile Ser Ala
                85                  90                  95

Gly Asp Glu Ile Asn Gly Ser Asp Ile Thr Ser Glu Lys Lys Met Ile
                100                 105                 110

Ser Arg Thr Glu Ser Arg Ser Leu Phe Glu Phe Lys Ser Val Pro Leu
            115                 120                 125

Tyr Gly Phe Thr Ser Ile Cys Gly Arg Arg Pro Glu Met Glu Asp Ala
    130                 135                 140

Val Ser Thr Ile Pro Arg Phe Leu Gln Ser Ser Ser Gly Ser Met Leu
145                 150                 155                 160

Asp Gly Arg Phe Asp Pro Gln Ser Ala Ala His Phe Phe Gly Val Tyr
                165                 170                 175

Asp Gly His Gly Gly Ser Gln Val Ala Asn Tyr Cys Arg Glu Arg Met
                180                 185                 190

His Leu Ala Leu Ala Glu Glu Ile Ala Lys Glu Lys Pro Met Leu Cys
            195                 200                 205

Asp Gly Asp Thr Trp Leu Glu Lys Trp Lys Lys Ala Leu Phe Asn Ser
    210                 215                 220

Phe Leu Arg Val Asp Ser Glu Ile Glu Ser Val Ala Pro Glu Thr Val
225                 230                 235                 240

Gly Ser Thr Ser Val Val Ala Val Val Phe Pro Ser His Ile Phe Val
                245                 250                 255

Ala Asn Cys Gly Asp Ser Arg Ala Val Leu Cys Arg Gly Lys Thr Ala
                260                 265                 270

Leu Pro Leu Ser Val Asp His Lys Pro Asp Arg Glu Asp Glu Ala Ala
            275                 280                 285

Arg Ile Glu Ala Ala Gly Gly Lys Val Ile Gln Trp Asn Gly Ala Arg
    290                 295                 300

Val Phe Gly Val Leu Ala Met Ser Arg Ser Ile Gly Asp Arg Tyr Leu
305                 310                 315                 320

Lys Pro Ser Ile Ile Pro Asp Pro Glu Val Thr Ala Val Lys Arg Val
                325                 330                 335

Lys Glu Asp Asp Cys Leu Ile Leu Ala Ser Asp Gly Val Trp Asp Val
                340                 345                 350

Met Thr Asp Glu Glu Ala Cys Glu Met Ala Arg Lys Arg Ile Leu Leu
            355                 360                 365

Trp His Lys Lys Asn Ala Val Ala Gly Asp Ala Ser Leu Leu Ala Asp
    370                 375                 380

Glu Arg Arg Lys Glu Gly Lys Asp Pro Ala Ala Met Ser Ala Ala Glu
385                 390                 395                 400

```
Tyr Leu Ser Lys Leu Ala Ile Gln Arg Gly Ser Lys Asp Asn Ile Ser
                405                 410                 415

Val Val Val Asp Leu Lys Pro Arg Arg Lys Leu Lys Ser Lys Pro
            420                 425                 430

Leu Asn

<210> SEQ ID NO 91
<211> LENGTH: 423
<212> TYPE: PRT
<213> ORGANISM: Artificial Sequence
<220> FEATURE:
<223> OTHER INFORMATION: synthetic polypeptide

<400> SEQUENCE: 91

Met Asp Glu Val Ser Pro Ala Val Ala Val Pro Phe Arg Pro Phe Thr
1               5                   10                  15

Asp Pro His Ala Gly Leu Arg Gly Tyr Cys Asn Gly Glu Ser Arg Val
            20                  25                  30

Thr Leu Pro Glu Ser Ser Cys Ser Gly Asp Gly Ala Met Lys Asp Ser
        35                  40                  45

Ser Phe Glu Ile Asn Thr Arg Gln Asp Ser Leu Thr Ser Ser Ser Ser
50                  55                  60

Ala Met Ala Gly Val Asp Ile Ser Ala Gly Asp Glu Ile Asn Gly Ser
65                  70                  75                  80

Asp Glu Phe Asp Pro Arg Ser Met Asn Gln Ser Glu Lys Lys Val Leu
                85                  90                  95

Ser Arg Thr Glu Ser Arg Ser Leu Phe Glu Phe Lys Cys Val Pro Leu
            100                 105                 110

Tyr Gly Val Thr Ser Ile Cys Gly Arg Arg Pro Glu Met Glu Asp Ser
        115                 120                 125

Val Ser Thr Ile Pro Arg Phe Leu Gln Val Ser Ser Ser Leu Leu
130                 135                 140

Asp Gly Arg Val Thr Asn Gly Phe Asn Pro His Leu Ser Ala His Phe
145                 150                 155                 160

Phe Gly Val Tyr Asp Gly His Gly Gly Ser Gln Val Ala Asn Tyr Cys
                165                 170                 175

Arg Glu Arg Met His Leu Ala Leu Thr Glu Glu Ile Val Lys Glu Lys
            180                 185                 190

Pro Glu Phe Cys Asp Gly Asp Thr Trp Gln Glu Lys Trp Lys Lys Ala
        195                 200                 205

Leu Phe Asn Ser Phe Met Arg Val Asp Ser Glu Ile Glu Thr Val Ala
210                 215                 220

His Ala Pro Glu Thr Val Gly Ser Thr Ser Val Val Ala Val Val Phe
225                 230                 235                 240

Pro Thr His Ile Phe Val Ala Asn Cys Gly Asp Ser Arg Ala Val Leu
                245                 250                 255

Cys Arg Gly Lys Thr Pro Leu Ala Leu Ser Val Asp His Lys Pro Asp
            260                 265                 270

Arg Asp Asp Glu Ala Ala Arg Ile Glu Ala Ala Gly Gly Lys Val Ile
        275                 280                 285

Arg Trp Asn Gly Ala Arg Val Phe Gly Val Leu Ala Met Ser Arg Ser
290                 295                 300

Ile Gly Asp Arg Tyr Leu Lys Pro Ser Val Ile Pro Asp Pro Glu Val
305                 310                 315                 320

Thr Ser Val Arg Arg Val Lys Glu Asp Asp Cys Leu Ile Leu Ala Ser
```

```
            325                 330                 335
Asp Gly Leu Trp Asp Val Met Thr Asn Glu Glu Val Cys Asp Leu Ala
            340                 345                 350

Arg Lys Arg Ile Leu Leu Trp His Lys Lys Asn Ala Met Ala Gly Glu
            355                 360                 365

Ala Leu Leu Pro Ala Glu Lys Arg Gly Glu Gly Lys Asp Pro Ala Ala
            370                 375                 380

Met Ser Ala Ala Glu Tyr Leu Ser Lys Met Ala Leu Gln Lys Gly Ser
385                 390                 395                 400

Lys Asp Asn Ile Ser Val Val Val Asp Leu Lys Gly Ile Arg Lys
                    405                 410                 415

Phe Lys Ser Lys Ser Leu Asn
                    420

<210> SEQ ID NO 92
<211> LENGTH: 612
<212> TYPE: PRT
<213> ORGANISM: Artificial Sequence
<220> FEATURE:
<223> OTHER INFORMATION: synthetic polypeptide

<400> SEQUENCE: 92

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Gly Gln Phe Tyr Pro
            35                  40                  45

Gly Arg Ala Ser Arg Trp Trp Met Lys Gln Ser Leu Ala His Leu Ser
    50                  55                  60

Gln Ser Leu Lys Ala Leu Gly Ser Asp Leu Thr Leu Ile Lys Thr His
65                  70                  75                  80

Asn Thr Ile Ser Ala Ile Leu Asp Cys Ile Arg Val Thr Gly Ala Thr
                    85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
            115                 120                 125

Tyr Asn Gly Asp Leu Leu Tyr Glu Pro Trp Glu Ile Tyr Cys Glu Lys
    130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
            195                 200                 205

Ala Trp Ser Pro Gly Trp Ser Asn Ala Asp Lys Leu Leu Asn Glu Phe
    210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
```

```
            260                 265                 270
Ala Arg Asp Lys Asn Ser Glu Gly Glu Ser Ala Asp Leu Phe Leu
            275                 280                 285

Arg Gly Ile Gly Leu Arg Glu Tyr Ser Arg Tyr Ile Cys Phe Asn Phe
            290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
                420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Pro Asp Glu Ile Val Ala Asp Ser Phe Glu Ala Leu Gly Ala
                500                 505                 510

Asn Thr Ile Lys Glu Pro Gly Leu Cys Pro Ser Val Ser Ser Asn Asp
            515                 520                 525

Gln Gln Val Pro Ser Ala Val Arg Tyr Asn Gly Ser Lys Arg Val Lys
            530                 535                 540

Pro Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Ser Val
                565                 570                 575

Phe Phe Val Ser Gln Ser Cys Ser Leu Ala Ser Glu Gly Lys Asn Leu
            580                 585                 590

Glu Gly Ile Gln Asp Ser Ser Asp Gln Ile Thr Thr Ser Leu Gly Lys
            595                 600                 605

Asn Gly Cys Lys
        610

<210> SEQ ID NO 93
<211> LENGTH: 335
<212> TYPE: PRT
<213> ORGANISM: Artificial Sequence
<220> FEATURE:
<223> OTHER INFORMATION: synthetic polypeptide

<400> SEQUENCE: 93

Met Asn Gly Ala Ile Gly Gly Asp Leu Leu Leu Asn Phe Pro Asp Met
```

```
           1               5                  10                 15
         Ser Val Leu Glu Arg Gln Arg Ala His Leu Lys Tyr Leu Asn Pro Thr
                        20                 25                 30

Phe Asp Ser Pro Leu Ala Gly Phe Ala Asp Ser Ser Met Ile Thr
                        35                 40                 45

Gly Gly Glu Met Asp Ser Tyr Leu Ser Thr Ala Gly Leu Asn Leu Pro
                        50                 55                 60

Met Met Tyr Gly Glu Thr Thr Val Glu Gly Asp Ser Arg Leu Ser Ile
         65                 70                 75                 80

Ser Pro Glu Thr Thr Leu Gly Thr Gly Asn Phe Lys Lys Arg Lys Phe
                        85                 90                 95

Asp Thr Glu Thr Lys Asp Cys Asn Glu Lys Lys Lys Met Thr Met
                        100                105                110

Asn Arg Asp Asp Leu Val Glu Glu Gly Glu Glu Lys Ser Lys Ile
                        115                120                125

Thr Glu Gln Asn Asn Gly Ser Thr Lys Ser Ile Lys Lys Met Lys His
                        130                135                140

Lys Ala Lys Lys Glu Glu Asn Asn Phe Ser Asn Asp Ser Ser Lys Val
         145                150                155                160

Thr Lys Glu Leu Glu Lys Thr Asp Tyr Ile His Val Arg Ala Arg Arg
                        165                170                175

Gly Gln Ala Thr Asp Ser His Ser Ile Ala Glu Arg Val Arg Arg Glu
                        180                185                190

Lys Ile Ser Glu Arg Met Lys Phe Leu Gln Asp Leu Val Pro Gly Cys
                        195                200                205

Asp Lys Ile Thr Gly Lys Ala Gly Met Leu Asp Glu Ile Ile Asn Tyr
         210                215                220

Val Gln Ser Leu Gln Arg Gln Ile Glu Phe Leu Ser Met Lys Leu Ala
         225                230                235                240

Ile Val Asn Pro Arg Pro Asp Phe Asp Met Asp Asp Ile Phe Ala Lys
                        245                250                255

Glu Val Ala Ser Thr Pro Met Thr Val Val Pro Ser Pro Glu Met Val
                        260                265                270

Leu Ser Gly Tyr Ser His Glu Met Val His Ser Gly Tyr Ser Ser Glu
                        275                280                285

Met Val Asn Ser Gly Tyr Leu His Val Asn Pro Met Gln Gln Val Asn
                        290                295                300

Thr Ser Ser Asp Pro Leu Ser Cys Phe Asn Asn Gly Glu Ala Pro Ser
         305                310                315                320

Met Trp Asp Ser His Val Gln Asn Leu Tyr Gly Asn Leu Gly Val
                        325                330                335

<210> SEQ ID NO 94
<211> LENGTH: 533
<212> TYPE: PRT
<213> ORGANISM: Artificial Sequence
<220> FEATURE:
<223> OTHER INFORMATION: synthetic polypeptide

<400> SEQUENCE: 94

Met Lys Arg Asp His His His His His Gln Asp Lys Lys Thr Met
1               5                  10                 15

Met Met Asn Glu Glu Asp Asp Gly Asn Gly Met Asp Glu Leu Leu Ala
                20                 25                 30

Val Leu Gly Tyr Lys Val Arg Ser Ser Glu Met Ala Asp Val Ala Gln
```

```
                35                  40                  45
Lys Leu Glu Gln Leu Glu Val Met Met Ser Asn Val Gln Glu Asp Asp
 50                  55                  60

Leu Ser Gln Leu Ala Thr Glu Thr Val His Tyr Asn Pro Ala Glu Leu
65                   70                  75                  80

Tyr Thr Trp Leu Asp Ser Met Leu Thr Asp Leu Asn Pro Pro Ser Ser
                85                  90                  95

Asn Ala Glu Tyr Asp Leu Lys Ala Ile Pro Gly Asp Ala Ile Leu Asn
                100                 105                 110

Gln Phe Ala Ile Asp Ser Ala Ser Ser Asn Gln Gly Gly Gly Gly
                115                 120                 125

Asp Thr Tyr Thr Thr Asn Lys Arg Leu Lys Cys Ser Asn Gly Val Val
                130                 135                 140

Glu Thr Thr Thr Ala Thr Ala Glu Ser Thr Arg His Val Val Leu Val
145                 150                 155                 160

Asp Ser Gln Glu Asn Gly Val Arg Leu Val His Ala Leu Leu Ala Cys
                165                 170                 175

Ala Glu Ala Val Gln Lys Glu Asn Leu Thr Val Ala Glu Ala Leu Val
                180                 185                 190

Lys Gln Ile Gly Phe Leu Ala Val Ser Gln Ile Gly Ala Met Arg Lys
                195                 200                 205

Val Ala Thr Tyr Phe Ala Glu Ala Leu Ala Arg Arg Ile Tyr Arg Leu
                210                 215                 220

Ser Pro Ser Gln Ser Pro Ile Asp His Ser Leu Ser Asp Thr Leu Gln
225                 230                 235                 240

Met His Phe Tyr Glu Thr Cys Pro Tyr Leu Lys Phe Ala His Phe Thr
                245                 250                 255

Ala Asn Gln Ala Ile Leu Glu Ala Phe Gln Gly Lys Lys Arg Val His
                260                 265                 270

Val Ile Asp Phe Ser Met Ser Gln Gly Leu Gln Trp Pro Ala Leu Met
                275                 280                 285

Gln Ala Leu Ala Leu Arg Pro Gly Gly Pro Pro Val Phe Arg Leu Thr
290                 295                 300

Gly Ile Gly Pro Pro Ala Pro Asp Asn Phe Asp Tyr Leu His Glu Val
305                 310                 315                 320

Gly Cys Lys Leu Ala His Leu Ala Glu Ala Ile His Val Glu Phe Glu
                325                 330                 335

Tyr Arg Gly Phe Val Ala Asn Thr Leu Ala Asp Leu Asp Ala Ser Met
                340                 345                 350

Leu Glu Leu Arg Pro Ser Glu Ile Glu Ser Val Ala Val Asn Ser Val
                355                 360                 365

Phe Glu Leu His Lys Leu Leu Gly Arg Pro Gly Ala Ile Asp Lys Val
                370                 375                 380

Leu Gly Val Val Asn Gln Ile Lys Pro Glu Ile Phe Thr Val Val Glu
385                 390                 395                 400

Gln Glu Ser Asn His Asn Ser Pro Ile Phe Leu Asp Arg Phe Thr Glu
                405                 410                 415

Ser Leu His Tyr Tyr Ser Thr Leu Phe Asp Ser Leu Glu Gly Val Pro
                420                 425                 430

Ser Gly Gln Asp Lys Val Met Ser Glu Val Tyr Leu Gly Lys Gln Ile
                435                 440                 445

Cys Asn Val Val Ala Cys Asp Gly Pro Asp Arg Val Glu Arg His Glu
                450                 455                 460
```

```
Thr Leu Ser Gln Trp Arg Asn Arg Phe Gly Ser Ala Gly Phe Ala Ala
465                 470                 475                 480

Ala His Ile Gly Ser Asn Ala Phe Lys Gln Ala Ser Met Leu Leu Ala
                485                 490                 495

Leu Phe Asn Gly Gly Glu Gly Tyr Arg Val Glu Glu Ser Asp Gly Cys
            500                 505                 510

Leu Met Leu Gly Trp His Thr Arg Pro Leu Ile Ala Thr Ser Ala Trp
        515                 520                 525

Lys Leu Ser Thr Asn
        530

<210> SEQ ID NO 95
<211> LENGTH: 345
<212> TYPE: PRT
<213> ORGANISM: Artificial Sequence
<220> FEATURE:
<223> OTHER INFORMATION: synthetic polypeptide

<400> SEQUENCE: 95

Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
                20                  25                  30

Ile Leu Arg Arg Pro Asp Gly Thr Phe Asn Arg His Leu Ala Glu Tyr
            35                  40                  45

Leu Asp Arg Lys Val Thr Ala Asn Ala Asn Pro Val Asp Gly Val Phe
        50                  55                  60

Ser Phe Asp Val Leu Ile Asp Arg Arg Ile Asn Leu Leu Ser Arg Val
65                  70                  75                  80

Tyr Arg Pro Ala Tyr Ala Asp Gln Glu Gln Pro Ser Ile Leu Asp
                85                  90                  95

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
        115                 120                 125

Thr Leu Cys Arg Arg Leu Val Gly Leu Cys Lys Cys Val Val Val Ser
    130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
    210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
        275                 280                 285
```

-continued

Asp Leu Ile Arg Asp Trp Gln Leu Ala Tyr Ala Glu Gly Leu Lys Lys
    290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
                325                 330                 335

Ile Ser Ala Phe Val Asn Ala Glu Cys
            340                 345

<210> SEQ ID NO 96
<211> LENGTH: 358
<212> TYPE: PRT
<213> ORGANISM: Artificial Sequence
<220> FEATURE:
<223> OTHER INFORMATION: synthetic polypeptide

<400> SEQUENCE: 96

Met Ala Gly Gly Asn Glu Val Asn Leu Asn Glu Cys Lys Arg Ile Val
1               5                   10                  15

Pro Leu Asn Thr Trp Val Leu Ile Ser Asn Phe Lys Leu Ala Tyr Lys
                20                  25                  30

Val Leu Arg Arg Pro Asp Gly Ser Phe Asn Arg Asp Leu Ala Glu Phe
            35                  40                  45

Leu Asp Arg Lys Val Pro Ala Asn Ser Phe Pro Leu Asp Gly Val Phe
50                  55                  60

Ser Phe Asp His Val Asp Ser Thr Thr Asn Leu Leu Thr Arg Ile Tyr
65                  70                  75                  80

Gln Pro Ala Ser Leu Leu His Gln Thr Arg His Gly Thr Leu Glu Leu
                85                  90                  95

Thr Lys Pro Leu Ser Thr Thr Glu Ile Val Pro Val Leu Ile Phe Phe
                100                 105                 110

His Gly Gly Ser Phe Thr His Ser Ser Ala Asn Ser Ala Ile Tyr Asp
            115                 120                 125

Thr Phe Cys Arg Arg Leu Val Thr Ile Cys Gly Val Val Val Val Ser
130                 135                 140

Val Asp Tyr Arg Arg Ser Pro Glu His Arg Tyr Pro Cys Ala Tyr Asp
145                 150                 155                 160

Asp Gly Trp Asn Ala Leu Asn Trp Val Lys Ser Arg Val Trp Leu Gln
                165                 170                 175

Ser Gly Lys Asp Ser Asn Val Tyr Val Tyr Leu Ala Gly Asp Ser Ser
            180                 185                 190

Gly Gly Asn Ile Ala His Asn Val Ala Val Arg Ala Thr Asn Glu Gly
        195                 200                 205

Val Lys Val Leu Gly Asn Ile Leu Leu His Pro Met Phe Gly Gly Gln
    210                 215                 220

Glu Arg Thr Gln Ser Glu Lys Thr Leu Asp Gly Lys Tyr Phe Val Thr
225                 230                 235                 240

Ile Gln Asp Arg Asp Trp Tyr Trp Arg Ala Tyr Leu Pro Glu Gly Glu
                245                 250                 255

Asp Arg Asp His Pro Ala Cys Asn Pro Phe Gly Pro Arg Gly Gln Ser
            260                 265                 270

Leu Lys Gly Val Asn Phe Pro Lys Ser Leu Val Val Ala Gly Leu
        275                 280                 285

Asp Leu Val Gln Asp Trp Gln Leu Ala Tyr Val Asp Gly Leu Lys Lys
    290                 295                 300

```
Thr Gly Leu Glu Val Asn Leu Leu Tyr Leu Lys Gln Ala Thr Ile Gly
305                 310                 315                 320

Phe Tyr Phe Leu Pro Asn Asp His Phe His Cys Leu Met Glu Glu
                325                 330                 335

Leu Asn Lys Phe Val His Ser Ile Glu Asp Ser Gln Ser Lys Ser Ser
                340                 345                 350

Pro Val Leu Leu Thr Pro
            355

<210> SEQ ID NO 97
<211> LENGTH: 344
<212> TYPE: PRT
<213> ORGANISM: Artificial Sequence
<220> FEATURE:
<223> OTHER INFORMATION: synthetic polypeptide

<400> SEQUENCE: 97

Met Ala Gly Ser Glu Glu Val Asn Leu Ile Glu Ser Lys Thr Val Val
1               5                   10                  15

Pro Leu Asn Thr Trp Val Leu Ile Ser Asn Phe Lys Leu Ala Tyr Asn
                20                  25                  30

Leu Leu Arg Arg Pro Asp Gly Thr Phe Asn Arg His Leu Ala Glu Phe
            35                  40                  45

Leu Asp Arg Lys Val Pro Ala Asn Ala Asn Pro Val Asn Gly Val Phe
    50                  55                  60

Ser Phe Asp Val Ile Ile Asp Arg Gln Thr Asn Leu Leu Ser Arg Val
65                  70                  75                  80

Tyr Arg Pro Ala Asp Ala Gly Thr Ser Pro Ser Ile Thr Asp Leu Gln
                85                  90                  95

Asn Pro Val Asp Gly Glu Ile Val Pro Ile Val Phe Phe His Gly
                100                 105                 110

Gly Ser Phe Ala His Ser Ser Ala Asn Ser Ala Ile Tyr Asp Thr Leu
            115                 120                 125

Cys Arg Arg Leu Val Gly Leu Cys Gly Ala Val Val Val Ser Val Asn
130                 135                 140

Tyr Arg Arg Ala Pro Glu Asn Arg Tyr Pro Cys Ala Tyr Asp Asp Gly
145                 150                 155                 160

Trp Ala Val Leu Lys Trp Val Asn Ser Ser Trp Leu Arg Ser Lys
                165                 170                 175

Lys Asp Ser Lys Val Arg Ile Phe Leu Ala Gly Asp Ser Ser Gly Gly
            180                 185                 190

Asn Ile Val His Asn Val Ala Val Arg Ala Val Glu Ser Arg Ile Asp
        195                 200                 205

Val Leu Gly Asn Ile Leu Leu Asn Pro Met Phe Gly Gly Thr Glu Arg
    210                 215                 220

Thr Glu Ser Glu Lys Arg Leu Asp Gly Lys Tyr Phe Val Thr Val Arg
225                 230                 235                 240

Asp Arg Asp Trp Tyr Trp Arg Ala Phe Leu Pro Glu Gly Glu Asp Arg
                245                 250                 255

Glu His Pro Ala Cys Ser Pro Phe Gly Pro Arg Ser Lys Ser Leu Glu
                260                 265                 270

Gly Leu Ser Phe Pro Lys Ser Leu Val Val Val Ala Gly Leu Asp Leu
            275                 280                 285

Ile Gln Asp Trp Gln Leu Lys Tyr Ala Glu Gly Leu Lys Lys Ala Gly
    290                 295                 300
```

```
Gln Glu Val Lys Leu Leu Tyr Leu Glu Gln Ala Thr Ile Gly Phe Tyr
305                 310                 315                 320

Leu Leu Pro Asn Asn Asn His Phe His Thr Val Met Asp Glu Ile Ala
            325                 330                 335

Ala Phe Val Asn Ala Glu Cys Gln
            340

<210> SEQ ID NO 98
<211> LENGTH: 113
<212> TYPE: PRT
<213> ORGANISM: Artificial Sequence
<220> FEATURE:
<223> OTHER INFORMATION: synthetic polypeptide

<400> SEQUENCE: 98

Met Gly Gly Leu Glu Pro Cys Ser Arg Leu Leu Leu Pro Leu Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 99
<211> LENGTH: 112
<212> TYPE: PRT
<213> ORGANISM: Artificial Sequence
<220> FEATURE:
<223> OTHER INFORMATION: synthetic polypeptide

<400> SEQUENCE: 99

Met Gly Gly Leu Glu Pro Cys Ser Arg Leu Leu Leu Pro Leu Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln Arg Pro Tyr Tyr Lys
            100                 105                 110

<210> SEQ ID NO 100
<211> LENGTH: 102
<212> TYPE: PRT
<213> ORGANISM: Artificial Sequence
```

<220> FEATURE:
<223> OTHER INFORMATION: synthetic polypeptide

<400> SEQUENCE: 100

Met Gly Gly Leu Glu Pro Cys Ser Arg Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
            100

<210> SEQ ID NO 101
<211> LENGTH: 101
<212> TYPE: PRT
<213> ORGANISM: Artificial Sequence
<220> FEATURE:
<223> OTHER INFORMATION: synthetic polypeptide

<400> SEQUENCE: 101

Met Gly Gly Leu Glu Pro Cys Ser Arg Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Thr Arg Lys Gln Arg Ile Thr Glu Thr Glu Ser Pro Tyr Gln
65                  70                  75                  80

Glu Leu Gln Gly Gln Arg Ser Asp Val Tyr Ser Asp Leu Asn Thr Gln
                85                  90                  95

Arg Pro Tyr Tyr Lys
            100

<210> SEQ ID NO 102
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 102

Glu Ser Pro Tyr Gln Glu Leu Gln Gly Gln Arg Ser Asp Val Tyr Ser
1               5                   10                  15

Asp Leu Asn Thr Gln
            20

<210> SEQ ID NO 103
<211> LENGTH: 86
<212> TYPE: PRT
<213> ORGANISM: Artificial Sequence
<220> FEATURE:

<223> OTHER INFORMATION: synthetic polypeptide

<400> SEQUENCE: 103

Met Ile Pro Ala Val Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
                35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 104
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 104

Asp Gly Val Tyr Thr Gly Leu Ser Thr Arg Asn Gln Glu Thr Tyr Glu
1               5                   10                  15

Thr Leu Lys His Glu
            20

<210> SEQ ID NO 105
<211> LENGTH: 171
<212> TYPE: PRT
<213> ORGANISM: Artificial Sequence
<220> FEATURE:
<223> OTHER INFORMATION: synthetic polypeptide

<400> SEQUENCE: 105

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
                115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys

<210> SEQ ID NO 106
<211> LENGTH: 127
<212> TYPE: PRT
<213> ORGANISM: Artificial Sequence
<220> FEATURE:
<223> OTHER INFORMATION: synthetic polypeptide

<400> SEQUENCE: 106

```
Met Glu His Ser Thr Phe Leu Ser Gly Leu Val Leu Ala Thr Leu Leu
1               5                   10                  15
Ser Gln Val Ser Pro Phe Lys Ile Pro Ile Glu Glu Leu Glu Asp Arg
            20                  25                  30
Val Phe Val Asn Cys Asn Thr Ser Ile Thr Trp Val Glu Gly Thr Val
        35                  40                  45
Gly Thr Leu Leu Ser Asp Ile Thr Arg Leu Asp Leu Gly Lys Arg Ile
    50                  55                  60
Leu Asp Pro Arg Gly Ile Tyr Arg Cys Asn Gly Thr Asp Ile Tyr Lys
65                  70                  75                  80
Asp Lys Glu Ser Thr Val Gln Val His Tyr Arg Thr Ala Asp Thr Gln
                85                  90                  95
Ala Leu Leu Arg Asn Asp Gln Val Tyr Gln Pro Leu Arg Asp Arg Asp
            100                 105                 110
Asp Ala Gln Tyr Ser His Leu Gly Gly Asn Trp Ala Arg Asn Lys
        115                 120                 125
```

<210> SEQ ID NO 107
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 107

```
Asp Gln Val Tyr Gln Pro Leu Arg Asp Arg Asp Asp Ala Gln Tyr Ser
1               5                   10                  15
His Leu Gly Gly Asn
            20
```

<210> SEQ ID NO 108
<211> LENGTH: 207
<212> TYPE: PRT
<213> ORGANISM: Artificial Sequence
<220> FEATURE:
<223> OTHER INFORMATION: synthetic polypeptide

<400> SEQUENCE: 108

```
Met Gln Ser Gly Thr His Trp Arg Val Leu Gly Leu Cys Leu Leu Ser
1               5                   10                  15
Val Gly Val Trp Gly Gln Asp Gly Asn Glu Glu Met Gly Gly Ile Thr
            20                  25                  30
Gln Thr Pro Tyr Lys Val Ser Ile Ser Gly Thr Thr Val Ile Leu Thr
        35                  40                  45
Cys Pro Gln Tyr Pro Gly Ser Glu Ile Leu Trp Gln His Asn Asp Lys
    50                  55                  60
Asn Ile Gly Gly Asp Glu Asp Asp Lys Asn Ile Gly Ser Asp Glu Asp
65                  70                  75                  80
His Leu Ser Leu Lys Glu Phe Ser Glu Leu Glu Gln Ser Gly Tyr Tyr
                85                  90                  95
```

```
Val Cys Tyr Pro Arg Gly Ser Lys Pro Glu Asp Ala Asn Phe Tyr Leu
                100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
                195                 200                 205

<210> SEQ ID NO 109
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 109

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 110
<211> LENGTH: 182
<212> TYPE: PRT
<213> ORGANISM: Artificial Sequence
<220> FEATURE:
<223> OTHER INFORMATION: synthetic polypeptide

<400> SEQUENCE: 110

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
```

165                 170                 175
Asn Gln Leu Arg Arg Asn
            180

<210> SEQ ID NO 111
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 111

Asp Gln Leu Tyr Gln Pro Leu Lys Asp Arg Glu Asp Asp Gln Tyr Ser
1               5                   10                  15

His Leu Gln Gly Asn
            20

<210> SEQ ID NO 112
<211> LENGTH: 163
<212> TYPE: PRT
<213> ORGANISM: Artificial Sequence
<220> FEATURE:
<223> OTHER INFORMATION: synthetic polypeptide

<400> SEQUENCE: 112

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 113
<211> LENGTH: 164
<212> TYPE: PRT
<213> ORGANISM: Artificial Sequence
<220> FEATURE:
<223> OTHER INFORMATION: synthetic polypeptide

<400> SEQUENCE: 113

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

```
Tyr Leu Leu Asp Gly Ile Leu Phe Ile Tyr Gly Val Ile Leu Thr Ala
             35                  40                  45

Leu Phe Leu Arg Val Lys Phe Ser Arg Ser Ala Asp Ala Pro Ala Tyr
 50                  55                  60

Gln Gln Gly Gln Asn Gln Leu Tyr Asn Glu Leu Asn Leu Gly Arg Arg
65                   70                  75                  80

Glu Glu Tyr Asp Val Leu Asp Lys Arg Gly Arg Asp Pro Glu Met
                 85                  90                  95

Gly Gly Lys Pro Gln Arg Arg Lys Asn Pro Gln Glu Gly Leu Tyr Asn
             100                 105                 110

Glu Leu Gln Lys Asp Lys Met Ala Glu Ala Tyr Ser Glu Ile Gly Met
         115                 120                 125

Lys Gly Glu Arg Arg Arg Gly Lys Gly His Asp Gly Leu Tyr Gln Gly
     130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 114
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 114

Asn Gln Leu Tyr Asn Glu Leu Asn Leu Gly Arg Arg Glu Glu Tyr Asp
1               5                   10                  15

Val Leu Asp Lys Arg
            20

<210> SEQ ID NO 115
<211> LENGTH: 22
<212> TYPE: PRT
<213> ORGANISM: Artificial Sequence
<220> FEATURE:
<223> OTHER INFORMATION: synthetic polypeptide

<400> SEQUENCE: 115

Glu Gly Leu Tyr Asn Glu Leu Gln Lys Asp Lys Met Ala Glu Ala Tyr
1               5                   10                  15

Ser Glu Ile Gly Met Lys
            20

<210> SEQ ID NO 116
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 116

Asp Gly Leu Tyr Gln Gly Leu Ser Thr Ala Thr Lys Asp Thr Tyr Asp
1               5                   10                  15

Ala Leu His Met Gln
            20

<210> SEQ ID NO 117
<211> LENGTH: 226
<212> TYPE: PRT
<213> ORGANISM: Artificial Sequence
```

<220> FEATURE:
<223> OTHER INFORMATION: synthetic polypeptide

<400> SEQUENCE: 117

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65              70                  75                  80

Leu Gly Pro Gly Glu Asp Pro Asn Gly Thr Leu Ile Ile Gln Asn Val
            85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
210                 215                 220

Lys Pro
225

<210> SEQ ID NO 118
<211> LENGTH: 188
<212> TYPE: PRT
<213> ORGANISM: Artificial Sequence
<220> FEATURE:
<223> OTHER INFORMATION: synthetic polypeptide

<400> SEQUENCE: 118

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65              70                  75                  80

Leu Gly Pro Gly Glu Asp Pro Asn Glu Pro Pro Arg Pro Phe Leu
            85                  90                  95

Asp Met Gly Glu Gly Thr Lys Asn Arg Ile Ile Thr Ala Glu Gly Ile

```
                   100                 105                 110
Ile Leu Leu Phe Cys Ala Val Val Pro Gly Thr Leu Leu Phe Arg
            115                 120                 125

Lys Arg Trp Gln Asn Glu Lys Leu Gly Leu Asp Ala Gly Asp Glu Tyr
            130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185

<210> SEQ ID NO 119
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 119

Glu Asn Leu Tyr Glu Gly Leu Asn Leu Asp Asp Cys Ser Met Tyr Glu
1               5                   10                  15

Asp Ile Ser Arg Gly
            20

<210> SEQ ID NO 120
<211> LENGTH: 20
<212> TYPE: PRT
<213> ORGANISM: Artificial Sequence
<220> FEATURE:
<223> OTHER INFORMATION: synthetic polypeptide

<400> SEQUENCE: 120

Arg Pro Arg Arg Ser Pro Ala Gln Asp Gly Lys Val Tyr Ile Asn Met
1               5                   10                  15

Pro Gly Arg Gly
            20

<210> SEQ ID NO 121
<211> LENGTH: 68
<212> TYPE: PRT
<213> ORGANISM: Artificial Sequence
<220> FEATURE:
<223> OTHER INFORMATION: synthetic polypeptide

<400> SEQUENCE: 121

Phe Trp Val Leu Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65

<210> SEQ ID NO 122
<211> LENGTH: 9
<212> TYPE: PRT
<213> ORGANISM: Artificial Sequence
```

```
<220> FEATURE:
<223> OTHER INFORMATION: synthetic polypeptide

<400> SEQUENCE: 122

Tyr Pro Tyr Asp Val Pro Asp Tyr Ala
1               5

<210> SEQ ID NO 123
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 123

Asp Tyr Lys Asp Asp Asp Asp Lys
1               5

<210> SEQ ID NO 124
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 124

His His His His His
1               5

<210> SEQ ID NO 125
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 125

His His His His His His
1               5

<210> SEQ ID NO 126
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 126

Trp Ser His Pro Gln Phe Glu Lys
1               5

<210> SEQ ID NO 127
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 127

Arg Tyr Ile Arg Ser
1               5

<210> SEQ ID NO 128
<211> LENGTH: 4
<212> TYPE: PRT
<213> ORGANISM: Artificial Sequence
<220> FEATURE:
```

```
<223> OTHER INFORMATION: synthetic polypeptide

<400> SEQUENCE: 128

Phe His His Thr
1

<210> SEQ ID NO 129
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 129

Trp Glu Ala Ala Ala Arg Glu Ala Cys Cys Arg Glu Cys Cys Ala Arg
1               5                   10                  15

Ala

<210> SEQ ID NO 130
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: the amino acids in these positions can be any
      amino acid
<220> FEATURE:
<221> NAME/KEY: MISC_FEATURE
<222> LOCATION: (4)..(4)
<223> OTHER INFORMATION: the amino acids in this position can be either
      Leu or Ile

<400> SEQUENCE: 130

Tyr Xaa Xaa Xaa
1

<210> SEQ ID NO 131
<211> LENGTH: 16
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
<222> LOCATION: (2)..(3)
<223> OTHER INFORMATION: the amino acids in these positions can be any
      amino acid
<220> FEATURE:
<221> NAME/KEY: MISC_FEATURE
<222> LOCATION: (4)..(4)
<223> OTHER INFORMATION: the amino acids in this positions can be either
      Leu or Ile
<220> FEATURE:
<221> NAME/KEY: MISC_FEATURE
<222> LOCATION: (5)..(10)
<223> OTHER INFORMATION: the amino acids in these positions can be any
      amino acid
<220> FEATURE:
<221> NAME/KEY: MISC_FEATURE
<222> LOCATION: (11)..(12)
<223> OTHER INFORMATION: the amino acids in these positions may be
      present or absent such that either one or two amino acids are
      present.  the amino acids in these positions can be any amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: MISC_FEATURE
```

```
<222> LOCATION: (16)..(16)
<223> OTHER INFORMATION: the amino acids in this positions can be either
      Leu or Ile

<400> SEQUENCE: 131

Tyr Xaa Xaa Xaa Xaa Xaa Xaa Xaa Xaa Xaa Xaa Tyr Xaa Xaa Xaa
1               5                   10                  15

<210> SEQ ID NO 132
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 132
gattacaagg atgacgatga caag                                              24

<210> SEQ ID NO 133
<211> LENGTH: 732
<212> TYPE: PRT
<213> ORGANISM: Artificial Sequence
<220> FEATURE:
<223> OTHER INFORMATION: synthetic polypeptide

<400> SEQUENCE: 133

Gly Gly Ala Thr Cys Cys Cys Ala Gly Gly Thr Ala Cys Ala Ala Cys
1               5                   10                  15

Thr Gly Cys Ala Gly Cys Ala Gly Thr Cys Thr Gly Gly Cys Cys
                20                  25                  30

Thr Gly Ala Gly Cys Thr Gly Ala Gly Ala Ala Gly Cys Cys Thr
                35                  40                  45

Gly Gly Cys Gly Cys Thr Thr Cys Ala Gly Thr Gly Ala Ala Gly Ala
        50                  55                  60

Thr Ala Thr Cys Cys Thr Gly Cys Ala Ala Gly Gly Cys Thr Thr Cys
65                  70                  75                  80

Thr Gly Gly Thr Thr Ala Cys Thr Cys Ala Thr Thr Cys Ala Cys Thr
                85                  90                  95

Gly Gly Cys Thr Ala Cys Ala Cys Cys Ala Thr Gly Ala Ala Cys Thr
                100                 105                 110

Gly Gly Gly Thr Gly Ala Ala Gly Cys Ala Gly Cys Cys
                115                 120                 125

Thr Gly Gly Ala Ala Gly Ala Gly Cys Cys Thr Thr Gly Ala Gly
                130                 135                 140

Thr Gly Gly Ala Thr Thr Gly Gly Ala Cys Thr Thr Ala Thr Thr Ala
145                 150                 155                 160

Cys Thr Cys Cys Thr Thr Ala Cys Ala Ala Thr Gly Gly Thr Gly Cys
                165                 170                 175

Thr Thr Cys Thr Ala Gly Cys Thr Ala Cys Ala Ala Cys Cys Ala Gly
                180                 185                 190

Ala Ala Gly Thr Thr Cys Ala Gly Gly Gly Cys Ala Ala Gly Gly
                195                 200                 205

Cys Cys Ala Cys Ala Thr Thr Ala Ala Cys Thr Gly Thr Ala Gly Ala
                210                 215                 220

Cys Ala Ala Gly Thr Cys Ala Thr Cys Cys Ala Gly Cys Ala Cys Ala
225                 230                 235                 240

Gly Cys Cys Thr Ala Cys Ala Thr Gly Gly Ala Cys Thr Cys
                245                 250                 255
```

-continued

```
Thr Cys Ala Gly Thr Cys Thr Gly Ala Cys Ala Thr Cys Thr Gly Ala
            260                 265                 270

Ala Gly Ala Cys Thr Cys Thr Gly Cys Ala Gly Thr Cys Thr Ala Thr
            275                 280                 285

Thr Thr Cys Thr Gly Thr Gly Cys Ala Ala Gly Gly Gly Gly Gly Gly
        290                 295                 300

Gly Thr Ala Cys Gly Ala Cys Gly Gly Ala Gly Gly Gly
305                 310                 315                 320

Thr Thr Thr Thr Gly Ala Cys Thr Ala Cys Thr Gly Gly Gly Gly Cys
                325                 330                 335

Cys Ala Ala Gly Gly Gly Ala Cys Cys Ala Cys Gly Gly Thr Cys Ala
            340                 345                 350

Cys Cys Gly Thr Cys Thr Cys Cys Thr Cys Ala Gly Gly Thr Gly Gly
            355                 360                 365

Ala Gly Gly Cys Gly Gly Thr Thr Cys Ala Gly Gly Cys Gly Gly Cys
        370                 375                 380

Gly Gly Thr Gly Gly Cys Thr Cys Thr Ala Gly Cys Gly Gly Thr Gly
385                 390                 395                 400

Gly Cys Gly Gly Ala Thr Cys Gly Gly Ala Cys Ala Thr Cys Gly Ala
                405                 410                 415

Gly Cys Thr Cys Ala Cys Thr Cys Ala Gly Thr Cys Thr Cys Cys Ala
            420                 425                 430

Gly Cys Ala Ala Thr Cys Ala Thr Gly Thr Cys Thr Gly Cys Ala Thr
            435                 440                 445

Cys Thr Cys Cys Ala Gly Gly Gly Ala Gly Ala Ala Gly Gly Thr
450                 455                 460

Cys Ala Cys Cys Ala Thr Gly Ala Cys Cys Thr Gly Cys Ala Gly Thr
465                 470                 475                 480

Gly Cys Cys Ala Gly Cys Thr Cys Ala Ala Gly Thr Gly Thr Ala Ala
                485                 490                 495

Gly Thr Thr Ala Cys Ala Thr Gly Cys Ala Cys Thr Gly Gly Thr Ala
            500                 505                 510

Cys Cys Ala Gly Cys Ala Gly Ala Ala Gly Thr Cys Ala Gly Gly Cys
            515                 520                 525

Ala Cys Cys Thr Cys Cys Cys Cys Ala Ala Ala Ala Gly Ala Thr
530                 535                 540

Gly Gly Ala Thr Thr Thr Ala Thr Gly Ala Cys Ala Cys Ala Thr Cys
545                 550                 555                 560

Cys Ala Ala Ala Cys Thr Gly Gly Cys Thr Thr Cys Thr Gly Gly Ala
                565                 570                 575

Gly Thr Cys Cys Cys Ala Gly Gly Thr Cys Gly Cys Thr Thr Cys Ala
            580                 585                 590

Gly Thr Gly Gly Cys Ala Gly Thr Gly Gly Gly Thr Cys Thr Gly Gly
            595                 600                 605

Ala Ala Ala Cys Thr Cys Thr Ala Cys Thr Cys Thr Cys
610                 615                 620

Ala Cys Ala Ala Thr Cys Ala Gly Cys Ala Gly Cys Gly Thr Gly Gly
625                 630                 635                 640

Ala Gly Gly Cys Thr Gly Ala Ala Gly Ala Thr Gly Ala Thr Gly Cys
                645                 650                 655

Ala Ala Cys Thr Thr Ala Thr Thr Ala Cys Thr Gly Cys Cys Ala Gly
            660                 665                 670

Cys Ala Gly Thr Gly Gly Ala Gly Thr Ala Ala Gly Cys Ala Cys Cys
```

```
                675                 680                 685
Cys Thr Cys Thr Cys Ala Cys Gly Thr Ala Cys Gly Gly Thr Gly Cys
            690                 695                 700
Thr Gly Gly Gly Ala Cys Ala Ala Ala Gly Thr Thr Gly Gly Ala Ala
705                 710                 715                 720
Ala Thr Cys Ala Ala Ala Gly Cys Thr Ala Gly Cys
                725                 730
```

<210> SEQ ID NO 134
<211> LENGTH: 244
<212> TYPE: PRT
<213> ORGANISM: Artificial Sequence
<220> FEATURE:
<223> OTHER INFORMATION: synthetic polypeptide

<400> SEQUENCE: 134

```
Gly Ser Gln Val Gln Leu Gln Gln Ser Gly Pro Glu Leu Glu Lys Pro
1               5                   10                  15
Gly Ala Ser Val Lys Ile Ser Cys Lys Ala Ser Gly Tyr Ser Phe Thr
            20                  25                  30
Gly Tyr Thr Met Asn Trp Val Lys Gln Ser His Gly Lys Ser Leu Glu
        35                  40                  45
Trp Ile Gly Leu Ile Thr Pro Tyr Asn Gly Ala Ser Ser Tyr Asn Gln
    50                  55                  60
Lys Phe Arg Gly Lys Ala Thr Leu Thr Val Asp Lys Ser Ser Ser Thr
65                  70                  75                  80
Ala Tyr Met Asp Leu Leu Ser Leu Thr Ser Glu Asp Ser Ala Val Tyr
                85                  90                  95
Phe Cys Ala Arg Gly Gly Tyr Asp Gly Arg Gly Phe Asp Tyr Trp Gly
            100                 105                 110
Gln Gly Thr Thr Val Thr Val Ser Ser Gly Gly Gly Gly Ser Gly Gly
        115                 120                 125
Gly Gly Ser Ser Gly Gly Gly Ser Asp Ile Glu Leu Thr Gln Ser Pro
    130                 135                 140
Ala Ile Met Ser Ala Ser Pro Gly Glu Lys Val Thr Met Thr Cys Ser
145                 150                 155                 160
Ala Ser Ser Ser Val Ser Tyr Met His Trp Tyr Gln Gln Lys Ser Gly
                165                 170                 175
Thr Ser Pro Lys Arg Trp Ile Tyr Asp Thr Ser Lys Leu Ala Ser Gly
            180                 185                 190
Val Pro Gly Arg Phe Ser Gly Ser Gly Ser Gly Asn Ser Tyr Ser Leu
        195                 200                 205
Thr Ile Ser Ser Val Glu Ala Glu Asp Asp Ala Thr Tyr Tyr Cys Gln
    210                 215                 220
Gln Trp Ser Lys His Pro Leu Thr Tyr Gly Ala Gly Thr Lys Leu Glu
225                 230                 235                 240
Ile Lys Ala Ser
```

<210> SEQ ID NO 135
<211> LENGTH: 729
<212> TYPE: DNA
<213> ORGANISM: Artificial Sequence
<220> FEATURE:
<223> OTHER INFORMATION: synthetic polynucleotide

<400> SEQUENCE: 135
ggatcccagg tgcagctgca ggaatctggc cctggcctcg tgaagcccag cgagacactg    60

```
agcctgacct gtaccgtgtc tggcggctct gtgtccagcg gcagctacta ctggtcctgg    120
atcagacagc cccctggcaa gggcctggaa tggatcggct acatctacta cagcggctcc    180
accaactaca accccagcct gaagtccaga gtgaccatca gcgtggacac cagcaagaac    240
cagttctccc tgaagctgag cagcgtgaca gccgccgata ccgccgtgta ctactgtgcc    300
agagagggca agaacggcgc cttcgacatc tggggccagg gcacaatggt caccgtgtca    360
tctggtggag aggatctggg ggaggcgga agcggaggcg gcggatctga tattcagatg    420
acccagagcc ccagcagcct gagcgcctct gtgggcgaca gagtgacaat acctgccgg    480 gccagccaga gcatcagcag ctacctgaac tggtatcagc agaagcccgg caaggccccc    540
aaactgctga tctacgccgc cagctctctg cagtctggcg tgcccagcag attttccggc    600
tctggcagcg gcaccgactt cacccctgacc atctctagcc tgcagccccga ggacttcgcc    660 acctactact gccagcagag ctacagcacc cccctgacct ttggcggagg caccaaggtg    720
gaaatcaag                                                             729
```

<210> SEQ ID NO 136
<211> LENGTH: 243
<212> TYPE: PRT
<213> ORGANISM: Artificial Sequence
<220> FEATURE:
<223> OTHER INFORMATION: synthetic polypeptide

<400> SEQUENCE: 136

```
Gly Ser Gln Val Gln Leu Gln Glu Ser Gly Pro Gly Leu Val Lys Pro
1               5                   10                  15

Ser Glu Thr Leu Ser Leu Thr Cys Thr Val Ser Gly Gly Ser Val Ser
            20                  25                  30

Ser Gly Ser Tyr Tyr Trp Ser Trp Ile Arg Gln Pro Pro Gly Lys Gly
        35                  40                  45

Leu Glu Trp Ile Gly Tyr Ile Tyr Tyr Ser Gly Ser Thr Asn Tyr Asn
    50                  55                  60

Pro Ser Leu Lys Ser Arg Val Thr Ile Ser Val Asp Thr Ser Lys Asn
65                  70                  75                  80

Gln Phe Ser Leu Lys Leu Ser Ser Val Thr Ala Ala Asp Thr Ala Val
                85                  90                  95

Tyr Tyr Cys Ala Arg Glu Gly Lys Asn Gly Ala Phe Asp Ile Trp Gly
            100                 105                 110

Gln Gly Thr Met Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ser Tyr Ser Thr Pro Leu Thr Phe Gly Gly Gly Thr Lys Val
225                 230                 235                 240
```

Glu Ile Lys

<210> SEQ ID NO 137
<211> LENGTH: 1044
<212> TYPE: DNA
<213> ORGANISM: Artificial Sequence
<220> FEATURE:
<223> OTHER INFORMATION: synthetic polynucleotide

<400> SEQUENCE: 137

```
atggctgcga gcgatgaagt taatcttatt gagagcagaa cagtggttcc tctcaataca     60
tgggttttaa tatccaactt caaagtagcc tacaatatcc ttcgtcgccc tgatggaacc    120
tttaaccgac acttagctga gtatctagac cgtaaagtca ctgcaaacgc caatccggtt    180
gatggggttt tctcgttcga tgtcttgatt gatcgcagga tcaatcttct aagcagagtc    240
tatagaccag cttatgcaga tcaagagcaa cctcctagta ttttagatct cgagaagcct    300
gttgatggcg acattgtccc tgttatattg ttcttccatg gaggtagctt tgctcattct    360
tctgcaaaca gtgccatcta cgatactctt gtcgcaggc ttgttggttt gtgcaagtgt    420
gttgttgtct ctgtgaatta tcggcgtgca ccagagaatc catacccttg tgcttatgat    480
gatggttgga ttgctcttaa ttgggttaac tcgagatctt ggcttaaatc caagaaagac    540
tcaaaggtcc atattttctt ggctggtgat agctctggag gtaacatcgc gcataatgtg    600
gctttaagag cgggtgaatc gggaatcgat gttttgggga acattctgct gaatcctatg    660
tttggtggga atgagagaac ggagtctgag aaaagtttgg atgggaaata ctttgtgacg    720
gttagagacc gcgattggta ctggaaagcg ttttacccg agggagaaga tagagagcat    780
ccagcgtgta atccgtttag cccgagaggg aaaagcttag aaggagtgag tttcccccaag    840
agtcttgtgg ttgtcgcggg tttggatttg attagagatt ggcagttggc atacgcggaa    900
gggctcaaga agcgggtca agaggttaag cttatgcatt tagagaaagc aactgttggg    960
ttttacctct tgcctaataa caatcatttc cataatgtta tggatgagat ttcggcgttt   1020
gtaaacgcgg aatgtatgcg tgac                                          1044
```

<210> SEQ ID NO 138
<211> LENGTH: 348
<212> TYPE: PRT
<213> ORGANISM: Artificial Sequence
<220> FEATURE:
<223> OTHER INFORMATION: synthetic polypeptide

<400> SEQUENCE: 138

```
Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45

Leu Asp Arg Lys Val Thr Ala Asn Ala Asn Pro Val Asp Gly Val Phe
    50                  55                  60

Ser Phe Asp Val Leu Ile Asp Arg Arg Ile Asn Leu Leu Ser Arg Val
65                  70                  75                  80

Tyr Arg Pro Ala Tyr Ala Asp Gln Glu Gln Pro Pro Ser Ile Leu Asp
                85                  90                  95

Leu Glu Lys Pro Val Asp Gly Asp Ile Val Pro Val Ile Leu Phe Phe
            100                 105                 110
```

```
His Gly Gly Ser Phe Ala His Ser Ser Ala Asn Ser Ala Ile Tyr Asp
        115                 120                 125

Thr Leu Cys Arg Arg Leu Val Gly Leu Cys Lys Cys Val Val Val Ser
    130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
    210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Val Ala Gly Leu
        275                 280                 285

Asp Leu Ile Arg Asp Trp Gln Leu Ala Tyr Ala Glu Gly Leu Lys Lys
    290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
                325                 330                 335

Ile Ser Ala Phe Val Asn Ala Glu Cys Met Arg Asp
            340                 345

<210> SEQ ID NO 139
<211> LENGTH: 276
<212> TYPE: DNA
<213> ORGANISM: Artificial Sequence
<220> FEATURE:
<223> OTHER INFORMATION: synthetic polynucleotide

<400> SEQUENCE: 139
atgaagagag atcatcatca tcatcatcat caagataaga agactatgat gatgaatgaa    60
gaagacgacg gtaacggcat ggatgagctt ctagctgttc ttggttacaa ggttaggtca   120
tccgaaatgg ctgatgttgc tcagaaactc gagcagcttg aagttatgat gtctaatgtt   180
caagaagacg atctttctca actcgctact gagactgttc actataatcc ggcggagctt   240
tacacgtggc ttgattctat gctcaccgac cttaat                             276

<210> SEQ ID NO 140
<211> LENGTH: 92
<212> TYPE: PRT
<213> ORGANISM: Artificial Sequence
<220> FEATURE:
<223> OTHER INFORMATION: synthetic polypeptide

<400> SEQUENCE: 140

Met Lys Arg Asp His His His His His His Gln Asp Lys Lys Thr Met
1               5                   10                  15
```

```
Met Met Asn Glu Glu Asp Asp Gly Asn Gly Met Asp Glu Leu Leu Ala
                20                  25                  30

Val Leu Gly Tyr Lys Val Arg Ser Ser Glu Met Ala Asp Val Ala Gln
            35                  40                  45

Lys Leu Glu Gln Leu Glu Val Met Met Ser Asn Val Gln Glu Asp Asp
50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn
                85                  90

<210> SEQ ID NO 141
<211> LENGTH: 729
<212> TYPE: DNA
<213> ORGANISM: Artificial Sequence
<220> FEATURE:
<223> OTHER INFORMATION: synthetic polynucleotide

<400> SEQUENCE: 141
ggatcccagg tgcagctggt gcagtctggc gccgaagtga aaagaccagg cgccagcgtg    60
caggtctcct gtagagccag cggctacagc atcaacacct actacatgca gtgggtgcgc   120
caggccccag cgctggact ggaatggatg ggcgtgatca accccagcgg cgtgacaagc    180
tacgcccaga aattccaggg cagagtgacc ctgaccaacg acaccagcac caacacagtg   240
tacatgcagc tgaacagcct gaccagcgcc gacaccgccg tgtactactg tgccagatgg   300
gccctgtggg gcgacttcgg catggatgtg tggggcaagg gcaccctcgt gaccgtgtct   360
agcggaggcg gaggatctgg cggaggggga tctggaggcg gcggaagcga catccagatg   420
acccagagcc ctagcaccct gagcgccagc atcggcgata gagtgaccat cacctgtcgg   480
gccagcgagg gcatctatca ctggctggcc tggtatcagc agaagcccgg caaggccccc   540
aagctgctga tctacaaggc cagctctctg gcctctggcg cccctagcag attttctggc   600
agcggctccg gcaccgactt cacccctgaca atcagcagcc tgcagcccga cgacttcgcc   660
acctactatt gccagcagta cagcaactac cccctgacct tcggcggagg caccaagctg   720
gaaatcaag                                                            729

<210> SEQ ID NO 142
<211> LENGTH: 243
<212> TYPE: PRT
<213> ORGANISM: Artificial Sequence
<220> FEATURE:
<223> OTHER INFORMATION: synthetic polypeptide

<400> SEQUENCE: 142

Gly Ser Gln Val Gln Leu Val Gln Ser Gly Ala Glu Val Lys Arg Pro
1               5                   10                  15

Gly Ala Ser Val Gln Val Ser Cys Arg Ala Ser Gly Tyr Ser Ile Asn
            20                  25                  30

Thr Tyr Tyr Met Gln Trp Val Arg Gln Ala Pro Gly Ala Gly Leu Glu
            35                  40                  45

Trp Met Gly Val Ile Asn Pro Ser Gly Val Thr Ser Tyr Ala Gln Lys
    50                  55                  60

Phe Gln Gly Arg Val Thr Leu Thr Asn Asp Thr Ser Thr Asn Thr Val
65                  70                  75                  80

Tyr Met Gln Leu Asn Ser Leu Thr Ser Ala Asp Thr Ala Val Tyr Tyr
                85                  90                  95
```

```
Cys Ala Arg Trp Ala Leu Trp Gly Asp Phe Gly Met Asp Val Trp Gly
                100                 105                 110

Lys Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Thr Leu Ser Ala Ser Ile Gly Asp Arg Val Thr Ile Thr Cys Arg
145                 150                 155                 160

Ala Ser Glu Gly Ile Tyr His Trp Leu Ala Trp Tyr Gln Gln Lys Pro
                165                 170                 175

Gly Lys Ala Pro Lys Leu Leu Ile Tyr Lys Ala Ser Ser Leu Ala Ser
            180                 185                 190

Gly Ala Pro Ser Arg Phe Ser Gly Ser Gly Ser Gly Thr Asp Phe Thr
            195                 200                 205

Leu Thr Ile Ser Ser Leu Gln Pro Asp Asp Phe Ala Thr Tyr Tyr Cys
        210                 215                 220

Gln Gln Tyr Ser Asn Tyr Pro Leu Thr Phe Gly Gly Gly Thr Lys Leu
225                 230                 235                 240

Glu Ile Lys

<210> SEQ ID NO 143
<211> LENGTH: 135
<212> TYPE: DNA
<213> ORGANISM: Artificial Sequence
<220> FEATURE:
<223> OTHER INFORMATION: synthetic polynucleotide

<400> SEQUENCE: 143
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                     135

<210> SEQ ID NO 144
<211> LENGTH: 204
<212> TYPE: DNA
<213> ORGANISM: Artificial Sequence
<220> FEATURE:
<223> OTHER INFORMATION: synthetic polynucleotide

<400> SEQUENCE: 144
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc ccgccgcccc cgggcccacc cgcaagcatt accagcccta tgccccacca     180
cgcgacttcg cagcctatcg ctcc                                           204

<210> SEQ ID NO 145
<211> LENGTH: 111
<212> TYPE: DNA
<213> ORGANISM: Artificial Sequence
<220> FEATURE:
<223> OTHER INFORMATION: synthetic polynucleotide

<400> SEQUENCE: 145
cggagggacc agaggctgcc ccccgatgcc cacaagcccc ctggggagg cagtttccgg       60 accccccatcc aagaggagca ggccgacgcc cactccaccc tggccaagat c              111
```

CHIMERIC ANTIGEN RECEPTOR AND METHODS OF USE THEREOF

CROSS-REFERENCE

This application is a continuation of U.S. patent application Ser. No. 15/835,329, filed Dec. 7, 2017, now U.S. Pat. No. 10,888,581, which is a continuation of U.S. patent application Ser. No. 15/801,133, filed Nov. 1, 2017, now U.S. patent Ser. No. 10/105,391, which is a division of U.S. patent application Ser. No. 15/419,729, filed on Jan. 30, 2017, now U.S. Pat. No. 9,821,012, which is a continuation of U.S. patent application Ser. No. 15/064,938, filed on Mar. 9, 2016, now U.S. Pat. No. 9,587,020, which is a continuation of U.S. patent application Ser. No. 14/766,105, filed on Aug. 5, 2015, which is a national stage filing under 35 U.S.C. § 371 of PCT/US2014/016527, filed Feb. 14, 2014, which claims the benefit of U.S. Provisional Patent Application No. 61/765,585, filed Feb. 15, 2013, each of which applications is incorporated herein by reference in its entirety.

STATEMENT REGARDING FEDERALLY SPONSORED RESEARCH

This invention was made with government support under Grant Nos. EY016546 and GM101782 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCSF-464WO SeqList_ST25.txt" created on Feb. 13, 2014 and having a size of 153 KB. The contents of the text file are incorporated by reference herein in their entirety.

Introduction

In cell-based adoptive immunotherapy, immune cells isolated from a patient can be modified to express synthetic proteins that enable the cells to perform new therapeutic functions after they are subsequently transferred back into the patient. An example of such a synthetic protein is a chimeric antigen receptor (CAR). An example of a currently used CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell, such are release of cytolytic molecules to induce tumor cell death, etc. However, such CARs are not capable of being pharmacologically controlled. There is a need in the art for a conditionally activatable CAR that can be controlled pharmacologically.

SUMMARY

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided.

BRIEF DESCRIPTION OF THE DRAWINGS

FIGS. 1A and 1B provide nucleotide and amino acid sequences of the domains of construct #122.

FIGS. 2A and 2B provide nucleotide and amino acid sequences of the domains of construct #123.

FIGS. 3A and 3B provide nucleotide and amino acid sequences of the domains of construct #125.

FIG. 4 provides nucleotide and amino acid sequences of the domains of construct #126.

FIGS. 5A and 5B provide nucleotide and amino acid sequences of the domains of construct #168.

FIGS. 6A-C provide nucleotide and amino acid sequences of the domains of construct #169.

FIGS. 7A and 7B provide nucleotide and amino acid sequences of the domains of construct #170.

FIGS. 8A and 8B provide nucleotide and amino acid sequences of the domains of construct #197.

FIGS. 9A-C provide nucleotide and amino acid sequences of the domains of construct #206.

FIGS. 10A and 10B provide nucleotide and amino acid sequences of the domains of construct #207.

FIGS. 11A-C provide nucleotide and amino acid sequences of the domains of construct #199.

FIGS. 18A and 18B depict various exemplary On-switch CAR.

FIGS. 22A and 22B provide nucleotide and amino acid sequences of the domains of construct #270.

FIGS. 23A and 23B provide nucleotide and amino acid sequences of the domains of construct #300.

FIGS. 24A and 24B provide nucleotide and amino acid sequences of the domains of construct #336.

FIGS. 25A and 25B provide nucleotide and amino acid sequences of the domains of construct #337.

FIGS. 26A and 26B provide nucleotide and amino acid sequences of the domains of construct #357.

FIGS. 27A and 27B provide nucleotide and amino acid sequences of the domains of construct #365.

FIGS. 28A and 28B provide nucleotide and amino acid sequences of the domains of construct #366.

FIGS. 29A and 29B provide nucleotide and amino acid sequences of the domains of construct #367.

FIGS. 30A and 30B provide nucleotide and amino acid sequences of the domains of construct #398.

FIGS. 31A and 31B provide nucleotide and amino acid sequences of the domains of construct #399.

FIGS. 32A and 32B provide nucleotide and amino acid sequences of the domains of construct #400.

FIGS. 33A and 33B provide nucleotide and amino acid sequences of the domains of construct #358.

DEFINITIONS

Figure 12:
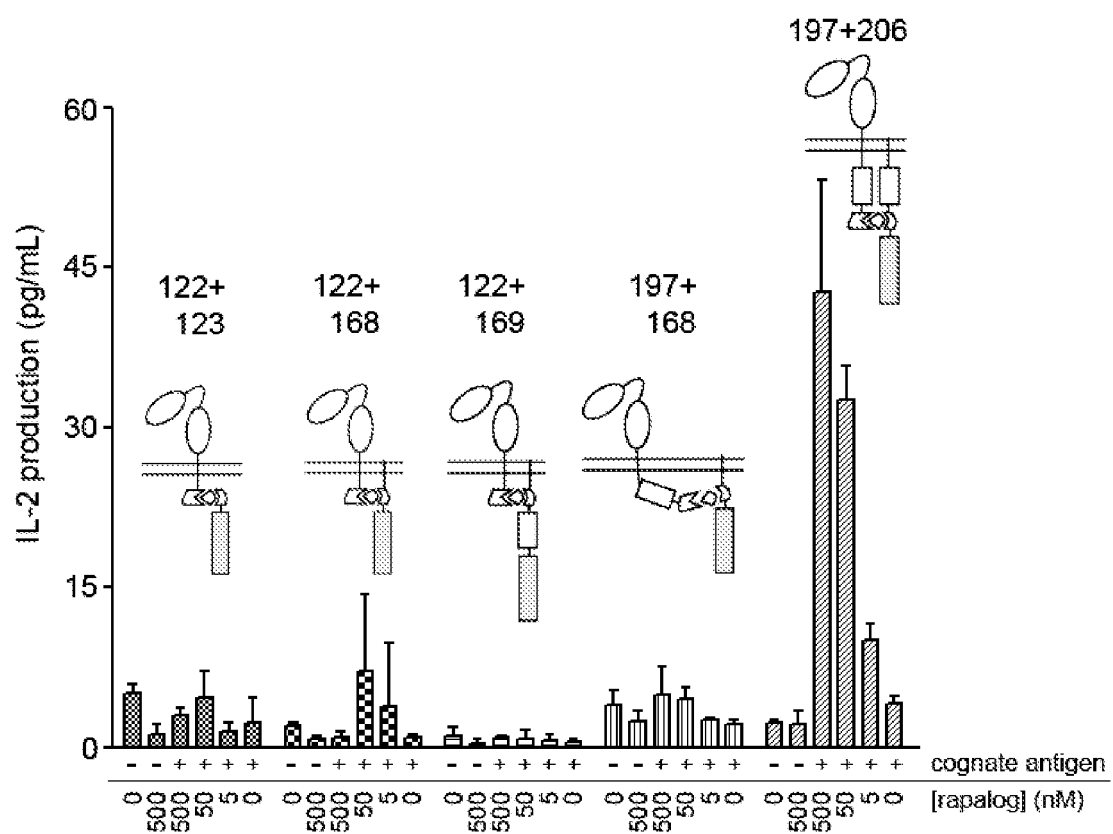
FIG. 12 depicts IL-2 production triggered by five On-switch CAR variants.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Single-chain Fv" or "sFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies, vol. 113, Rosenburg and Moore* eds., Springer-Verlag, New York, pp. 269-315 (1994).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "hinge region" refers to a flexible polypeptide connector region (also referred to herein as "hinge" or "spacer") providing structural flexibility and spacing to flanking polypeptide regions and can consist of natural or synthetic polypeptides. A "hinge region" derived from an immunoglobulin (e.g., IgG1) is generally defined as stretching from $Glu_{216}$ to $Pro_{230}$ of human IgG1 (Burton (1985) *Molec. Immunol.*, 22:161-206). Hinge regions of other IgG isotypes may be aligned with the IgG1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include complete hinge region derived from an antibody of a different class or subclass from that of the CH1 domain. The term "hinge region" can also include regions derived from CD8 and other receptors that provide a similar function in providing flexibility and spacing to flanking regions.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells (CD4$^+$ cells), cytotoxic T-cells (CD8$^+$ cells), T-regulatory cells (Treg) and gamma-delta T cells.

A "cytotoxic cell" includes CD8+ T cells, natural-killer (NK) cells, and neutrophils, which cells are capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent, or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptor and reference to "the dimerizer-binding pair" includes reference to one or more dimerizer-binding pairs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a heterodimeric, conditionally active chimeric antigen receptor (CAR), and a nucleic acid comprising a nucleotide sequence encoding the CAR. The present disclosure provides cells genetically modified to produce the CAR. A CAR of the present disclosure can be used in various methods, which are also provided. HETERODIMERIC, CONDITIONALLY ACTIVE CHIMERIC ANTIGEN RECEPTOR.

The present disclosure provides a heterodimeric, conditionally active chimeric antigen receptor, which, for simplicity, is referred to herein as "CAR."

In some embodiments, a CAR of the present disclosure comprises: a) a first polypeptide comprising: i) a member of a specific binding pair (e.g., an antigen-binding domain); ii) a first modulatory domain; iii) a first member of a dimerization pair; and iv) a transmembrane domain interposed between the member of a specific binding pair (e.g., an antigen-binding domain) and the first modulatory domain; and b) a second polypeptide comprising: i) a transmembrane domain; ii) a second modulatory domain; iii) a second member of the dimerization pair; and iv) an intracellular signaling domain. The modulatory domain can be a co-stimulatory domain.

In some embodiments, a CAR of the present disclosure comprises: a) a first polypeptide comprising: i) a member of a specific binding pair (e.g., an antigen-binding domain); ii) a first co-stimulatory domain; iii) a first member of a dimerization pair (e.g., a dimerizer-binding pair); and iv) a transmembrane domain interposed between the member of a specific binding pair (e.g., an antigen-binding domain) and the first co-stimulatory domain; and b) a second polypeptide comprising: i) a transmembrane domain; ii) a second co-stimulatory domain; iii) a second member of the dimerization pair (e.g., the dimerizer-binding pair); and iv) an intracellular signaling domain.

In some embodiments, a CAR of the present disclosure comprises: a) a first polypeptide comprising: i) a member of a specific binding pair (e.g., an antigen-binding domain); ii) a modulatory domain; iii) a first member of a dimerization pair (e.g., a dimerizer-binding pair); iv) a transmembrane domain interposed between the member of a specific binding pair (e.g., an antigen-binding domain) and the modulatory domain; and b) a second polypeptide comprising: i) a second member of the dimerization pair (e.g., the dimerizer-binding pair); and ii) an intracellular signaling domain. The modulatory domain can be a co-stimulatory domain.

In some embodiments, a CAR of the present disclosure comprises: a) a first polypeptide comprising: i) a member of a specific binding pair (e.g., an antigen-binding domain); ii)

a co-stimulatory domain; iii) a first member of a dimerization pair (e.g., a dimerizer-binding pair); iv) a transmembrane domain interposed between the member of a specific binding pair (e.g., an antigen-binding domain) and the co-stimulatory domain; and b) a second polypeptide comprising: i) a second member of the dimerization pair (e.g., the dimerizer-binding pair); and ii) an intracellular signaling domain.

Figure 17:
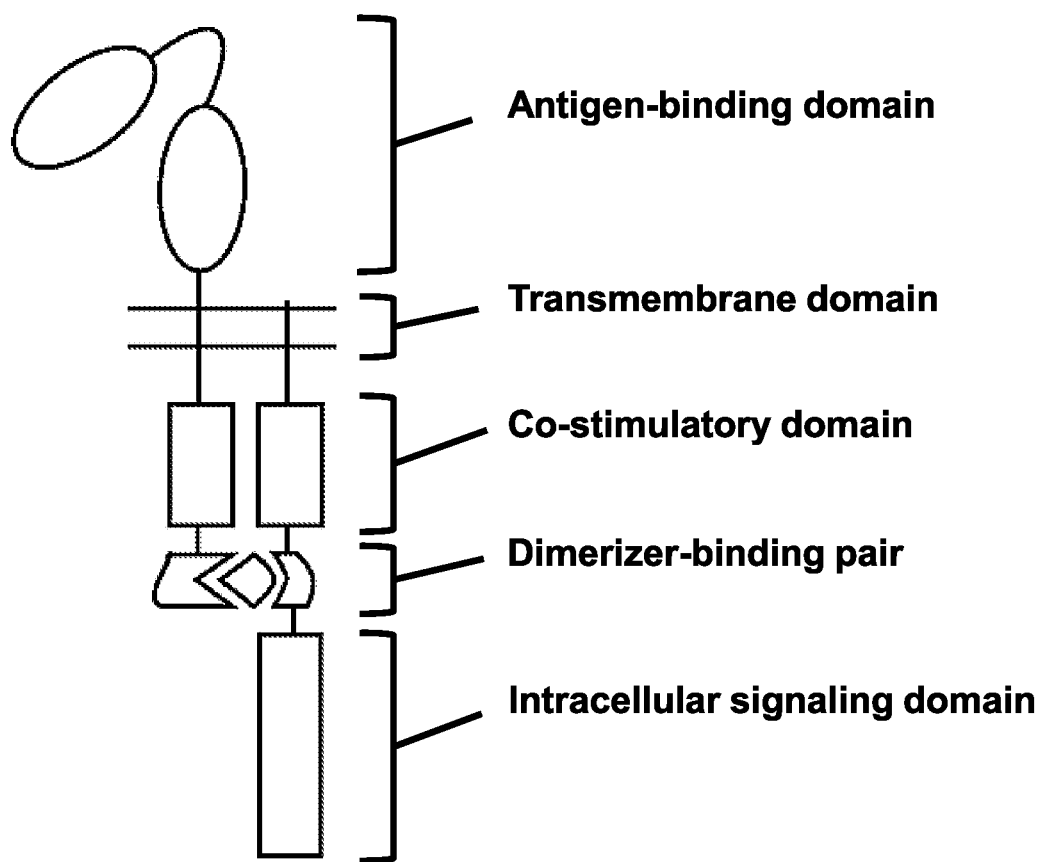
FIG. 17 is a schematic representation of an exemplary On-switch CAR.

An example of a subject CAR is represented schematically in FIG. 17. A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell. When present in the plasma membrane of a eukaryotic cell, a CAR of the present disclosure is active in the presence of: 1) a dimerizing agent binds to the first and second members of the dimerizer-binding pair in the CAR, or otherwise induces dimerization of the first and second members of the dimer; and 2) a factor that binds the member of a specific binding pair (e.g., an antigen-binding domain), e.g., an antigen that binds the antigen-binding domain of the CAR. The factor that binds the member of the specific binding pair is a second member of the specific binding pair. The second member of the specific binding pair can be a soluble (e.g., not bound to a cell) factor; a factor present on the surface of a cell such as a target cell; a factor presented on a solid surface; a factor present in a lipid bilayer; and the like. Where the member of a specific binding pair is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by a second member of a specific binding pair that binds the member of the specific-binding pair of the CAR (e.g., an antigen that binds the antigen-binding domain of the CAR) and a dimerizing agent, increases expression of at least one nucleic acid in the cell. For example, in some cases, a CAR of the present disclosure, when present in the plasma membrane of a eukaryotic cell, and when activated by an antigen that binds the antigen-binding domain of the CAR and a dimerizing agent, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of the antigen and/or the dimerizing agent.

As an example, the second polypeptide of a CAR of the present disclosure can include an immunoreceptor tyrosine-based activation motif (ITAM)-containing intracellular signaling polypeptide; in such cases, a CAR of the present disclosure, when present in the plasma membrane of a eukaryotic cell, and when activated by an antigen that binds the antigen-binding domain of the CAR and a dimerizing agent, increases nuclear factor of activated T cells (NFAT)-dependent transcription. NFAT-dependent transcription includes transcription induced by any member of the NFAT family, including, e.g., NFATc1, NFATc2, NFATc3, NFATc4, NFAT5; AP-1; Sp1; NKκB; and the like.

A CAR of the present disclosure, when present in the plasma membrane of a eukaryotic cell, and when activated by an antigen that binds the antigen-binding domain of the CAR and a dimerizing agent, can, in some instances, result in increased production of one or more cytokines by the cell. For example, a CAR of the present disclosure, when present in the plasma membrane of a eukaryotic cell, and when activated by an antigen that binds the antigen-binding domain of the CAR and a dimerizing agent, can increase production of a cytokine by the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the cell in the absence of the antigen and/or the dimerizing agent. Cytokines whose production can be increased include, but are not limited to, an interferon, e.g., IL-2, interferon gamma (IFN-γ), tumor necrosis factor-alpha (TNF-α), IL-15, IL-12, IL-4, IL-5, IL-10; a chemokine; a growth factor; and the like.

In some cases, a CAR of the present disclosure, when present in the plasma membrane of a eukaryotic cell, and when activated by an antigen that binds the antigen-binding domain of the CAR and a dimerizing agent, can result in both an increase in transcription of a nucleic acid in the cell and an increase in production of a cytokine by the cell.

In some instances, a CAR of the present disclosure, when present in the plasma membrane of a eukaryotic cell, and when activated by a dimerizing agent, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by a dimerizing agent, increases cytotoxic activity of the cell toward a target cell that expresses on its cell surface an antigen to which the antigen-binding domain of the first polypeptide of the CAR binds. For example, where the eukaryotic cell is an NK cell or a T lymphocyte, a CAR of the present disclosure, when present in the plasma membrane of the cell, and when activated by a dimerizing agent, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the dimerizing agent.

In some cases, a CAR of the present disclosure, when present in the plasma membrane of a eukaryotic cell, and when activated by an antigen that binds the antigen-binding domain of the CAR and a dimerizing agent, can result in other CAR activation related events such as proliferation and expansion (either due to increased cellular division or anti-apoptotic responses).

In some cases, a CAR of the present disclosure, when present in the plasma membrane of a eukaryotic cell, and when activated by an antigen that binds the antigen-binding domain of the CAR and a dimerizing agent, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane. Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a hinge region present in both the first polypeptide of the first CAR and the first polypeptide of the second CAR.

In some cases, a CAR of the present disclosure can be present in a eukaryotic cell membrane, where the first polypeptides of the CAR comprise an antibody fragment and the second polypeptides of the CAR comprise a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

Member of a Specific Binding Pair

A CAR of the present disclosure includes a member of a specific binding pair. Specific binding pairs include, but are not limited to, antigen-antibody binding pairs; ligand-receptor binding pairs; and the like. Thus, a member of a specific binding pair suitable for use in a CAR of the present disclosure includes an antigen; an antibody; a ligand; and a ligand-binding receptor.

Antigen-Binding Domain

An antigen-binding domain suitable for use in a CAR of the present disclosure can be any antigen-binding polypeptide, a wide variety of which are known in the art. In some instances, the antigen-binding domain is a single chain Fv (scFv). Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

An antigen-binding domain suitable for use in a CAR of the present disclosure can have a variety of antigen-binding specificities. In some cases, the antigen-binding domain is specific for an epitope present in an antigen that is expressed by (synthesized by) a cancer cell, i.e., a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an antigen-binding domain of a subject CAR can bind include, e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like.

Ligand

In some cases, a member of a specific binding pair suitable for use in a subject CAR is a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); and the like.

Where the member of a specific binding pair in a subject CAR is a ligand, the CAR can be activated in the presence of both a dimerizer agent and a second member of the specific binding pair, where the second member of the specific binding pair is a receptor for the ligand. For example, where the ligand is VEGF, the second member of the specific binding pair can be a VEGF receptor, including a soluble VEGF receptor. As another example, where the ligand is heregulin, the second member of the specific binding pair can be Her2.

Receptors

As noted above, in some cases, the member of a specific binding pair that is included in a subject CAR is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); Her2; CD27; a natural cytotoxicity receptor (NCR) (e.g., NKP30 (NCR3/CD337) polypeptide (receptor for HLA-B-associated transcript 3 (BAT3) and B7-H6); etc.); etc.

Hinge Region

In some cases, the first polypeptide of a subject CAR comprises a hinge region (also referred to herein as a "spacer"), where the hinge region is interposed between the antigen-binding domain and the transmembrane domain. In some cases, the hinge region is an immunoglobulin heavy chain hinge region. In some cases, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Suitable spacers can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids.

Exemplary spacers include glycine polymers $(G)_n$, glycine-serine polymers (including, for example, $(GS)_n$, $(GSGGS)_n$(SEQ ID NO:37) and $(GGGS)_n$(SEQ ID NO:38), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, Rev. *Computational Chem.* 11173-142 (1992)). Exemplary spacers can comprise amino acid sequences including, but not limited to, GGSG (SEQ ID NO:39), GGSGG (SEQ ID NO:40), GSGSG (SEQ ID NO:41), GSGGG (SEQ ID NO:42), GGGSG (SEQ ID NO:43), GSSSG (SEQ ID NO:44), and the like.

In some cases, the hinge region in the first polypeptide of a subject CAR includes at least one cysteine. For example, in some cases, the hinge region can include the sequence Cys-Pro-Pro-Cys. If present, a cysteine in the hinge region of a first CAR can be available to form a disulfide bond with a hinge region in a second CAR.

Immunoglobulin hinge region amino acid sequences are known in the art; see, e.g., Tan et al. (1990) *Proc. Natl. Acad. Sci.* USA 87:162; and Huck et al. (1986) *Nucl. Acids Res.* 14:1779. As non-limiting examples, an immunoglobulin hinge region can include one of the following amino acid sequences: DKTHT (SEQ ID NO:45); CPPC (SEQ ID NO:46); CPEPKSCDTPPPCPR (SEQ ID NO:47) (see, e.g., Glaser et al. (2005) *J. Biol. Chem.* 280:41494); ELKTPLGDTTHT (SEQ ID NO:48); KSCDKTHTCP (SEQ ID NO:49); KCCVDCP (SEQ ID NO:50); KYGPPCP (SEQ ID NO:51); EPKSCDKTHTCPPCP (SEQ ID NO:52) (human IgG1 hinge); ERKCCVECPPCP (SEQ ID NO:53) (human IgG2 hinge); ELKTPLGDTTHTCPRCP (SEQ ID NO:54) (human IgG3 hinge); SPNMVPHAHHAQ (SEQ ID NO:55) (human IgG4 hinge); and the like.

The hinge region can comprise an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, $His_{229}$ of human IgG1 hinge can be substituted with Tyr, so that the hinge region comprises the sequence EPKSCDKTYTCPPCP (SEQ ID NO:52); see, e.g., Yan et al. (2012) *J. Biol. Chem.* 287:5891.

The hinge region can comprise an amino acid sequence derived from human CD8; e.g., the hinge region can comprise the amino acid sequence: TTTPAPRPPTPAPTIA-SQPLSLRPEACRPAAGGAVHTRGLDFACD (SEQ ID NO:56), or a variant thereof.

Transmembrane Domain

The first and the second polypeptides of a CAR of the present disclosure include transmembrane domains for insertion into a eukaryotic cell membrane. The transmembrane domain of the first polypeptide is interposed between the antigen-binding domain and the co-stimulatory domain. Where the first polypeptide includes a hinge region, the transmembrane domain is interposed between the hinge region and the co-stimulatory domain, such that the first polypeptide comprises, in order from the amino terminus (N-terminus) to the carboxyl terminus (C-terminus): an antigen-binding domain; a hinge region; a transmembrane domain; a first co-stimulatory domain; and a first member of a dimerizer-binding pair.

The transmembrane domain of the second polypeptide is at or near the N-terminus of the polypeptide, such that the second polypeptide comprises, in order from N-terminus to C-terminus: a transmembrane domain; a second co-stimulatory domain; a second member of the dimerizer-binding pair; and an intracellular signaling domain.

Any transmembrane (TM) domain that provides for insertion of a polypeptide into the cell membrane of a eukaryotic (e.g., mammalian) cell is suitable for use. As one non-limiting example, the TM sequence IYI-WAPLAGTCGVLLLSLVITLYC (SEQ ID NO:30) can be used. Additional non-limiting examples of suitable™ sequences include: a) CD8 beta derived: LGLL-VAGVLVLLVSLGVAIHLCC (SEQ ID NO:57); b) CD4 derived: ALIVLGGVAGLLLFIGLGIFFCVRC (SEQ ID NO:58); c) CD3 zeta derived: LCYLLDGILFIYGVILT-ALFLRV (SEQ ID NO:59); d) CD28 derived: WVLVVVGGVLACYSLLVTVAFIIFWV (SEQ ID NO:60); e) CD134 (OX40) derived: VAAILGLGLVLGLLGPLAILLALYLL (SEQ ID NO:61); and f) CD7 derived: ALPAALAVISFLLGLGLGVACVLA (SEQ ID NO:62).

Linkers

In some cases, a first polypeptide of a subject CAR includes a linker between any two adjacent domains. For example, a linker can be disposed between the transmembrane domain and the first co-stimulatory domain of the first polypeptide. As another example, a linker can be disposed between the first co-stimulatory domain and the first member of a dimerizer-binding pair of the first polypeptide. As another example, a linker can be disposed between the transmembrane domain and the second co-stimulatory domain of the second polypeptide. As another example, a linker can be disposed between the second co-stimulatory domain and the second member of the dimerizer-binding pair of the second polypeptide. As another example, a linker can be disposed between the second member of the dimerizer-binding pair and the intracellular signaling domain of the second polypeptide.

The linker peptide may have any of a variety of amino acid sequences. Proteins can be joined by a spacer peptide, generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, GSGGS$_n$ (SEQ ID NO:37) and GGGS$_n$ (SEQ ID NO:38), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGSG (SEQ ID NO:39), GGSGG (SEQ ID NO:40), GSGSG (SEQ ID NO:41), GSGGG (SEQ ID NO:42), GGGSG (SEQ ID NO:43), GSSSG (SEQ ID NO:44), and the like. The ordinarily skilled artisan will recognize that design of a peptide conjugated to any elements described above can include linkers that are all or partially flexible, such that the linker can include a flexible linker as well as one or more portions that confer less flexible structure.

Modulatory Domains

Modulatory domains suitable for use in a CAR of the present disclosure include co-stimulatory domains.

In some cases, the modulatory domain on the first polypeptide of a subject CAR has substantially the same amino acid sequence as the modulatory domain on the second polypeptide of the CAR. For example, in some cases, the modulatory domain on the first polypeptide of a CAR comprises an amino acid sequence that is at least about 90%, at least about 95%, at least about 98%, at least about 99%, or 100%, identical to the amino acid sequence of the modulatory domain on the second polypeptide of the CAR. The modulatory domain of the first polypeptide of a subject CAR can have substantially the same length as the modulatory domain of the second polypeptide of a subject CAR; e.g., the first and second modulatory domains can differ in length from one another by fewer than 10 amino acids, or fewer than 5 amino acids. In some cases, the first and second modulatory domains have the same length.

A modulatory domain suitable for inclusion in the first and the second polypeptide of a subject CAR can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains suitable for use in a CAR of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD28, ICOS, OX-40, BTLA, CD27, CD30, GITR, and HVEM.

In some cases, the co-stimulatory domain on the first polypeptide of a subject CAR has substantially the same amino acid sequence as the co-stimulatory domain on the second polypeptide of the CAR. For example, in some cases, the co-stimulatory domain on the first polypeptide of a CAR comprises an amino acid sequence that is at least about 90%, at least about 95%, at least about 98%, at least about 99%, or 100%, identical to the amino acid sequence of the co-stimulatory domain on the second polypeptide of the CAR. The co-stimulatory domain of the first polypeptide of a subject CAR can have substantially the same length as the co-stimulatory domain of the second polypeptide of a subject CAR; e.g., the first and second co-stimulatory domains can differ in length from one another by fewer than 10 amino acids, or fewer than 5 amino acids. In some cases, the first and second co-stimulatory domains have the same length.

A co-stimulatory domain suitable for inclusion in the first and the second polypeptide of a subject CAR can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some cases, the co-stimulatory domain is derived from an intracellular portion of the transmembrane protein 4-1BB (also known as TNFRSF9; CD137; 4-1BB; CDw137; ILA; etc.). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: KRGRKKLLY-IFKQPFMRPVQTTQEEDGCSCRFPEEEEGGCEL (SEQ ID NO:24). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 (also known as Tp44). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: FWVRSKRSRLLHSDYMNMTPRRPGP-TRKHYQPYAPPRDFAAYRS (SEQ ID NO:63).

In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein ICOS (also known as AILIM, CD278, and CVID1). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: TKKKYSSSVHDPNG-EYMFMRAVNTAKKSRLTDVTL (SEQ ID NO:64). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein OX-40 (also known as TNFRSF4, RP5-902P8.3, ACT35, CD134, OX40, TXGP1L). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: RRDQRLPPDAHKPPGGGSFRTPIQEEQA-DAHSTLAKI (SEQ ID NO:65). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein BTLA (also known as BTLA1 and CD272). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: CCLR-RHQGKQNELSDTAGREINLVDAHLKSEQTEAST-RQNSQVLLSETGIYDNDPD LCFRMQEG-SEVYSNPCLEENKPGIVYASLNHSVIGPNSRLARNVK EAPTEYASICVR S (SEQ ID NO:66).

In some cases, the co-stimulatory domain is derived from an intracellular portion of the transmembrane protein CD27 (also known as S152, T14, TNFRSF7, and Tp55). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: HQRRKYRSNKGESPVEPAEPCRYSCPREEEGSTIP-IQEDYRKPEPACSP (SEQ ID NO:67). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD30 (also known as TNFRSF8, D1S166E, and Ki-1). For example, a suitable co-stimulatory domain can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of the following amino acid sequence: RRACRKRIRQKLHLCY-PVQTSQPKLELVDSRPRRSSTQLRSGASVTEPVAEER-GLMS QPLMETCHSVGAAYLESLPLQ-DASPAGGPSSPRDLPEPRVSTEHTNNKIEKIYIMKA DTVIVGTVKAELPEGRGLAGPAEPELEEELEADHTP-HYPEQETEPPLGSCSDVMLSV EEEGKEDPLPTAASGK (SEQ ID NO:68).

In some cases, the co-stimulatory domain is derived from an intracellular portion of the transmembrane protein GITR (also known as TNFRSF18, RP5-902P8.2, AITR, CD357, and GITR-D). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: HIWQLRSQCMWPRETQLLLEVPPSTE-DARSCQFPEEERGERSAEEKGRLGDLWV (SEQ ID NO:69). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can comprise an amino acid sequence having at least about 75%, at least about 80%, at least about 85%, at least about 90%, at least about 95%, at least about 98%, or 100% amino acid sequence identity to the following amino acid sequence: CVKRRKPRGDVVKVIVSVQRKRQEAEGEAT-VIEALQAPPDVTTVAVEETIPSFTGRS PNH (SEQ ID NO:70). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Dimer Pairs

Dimer pairs suitable for use in a subject CAR include dimerizer-binding pairs. Dimerizer-binding pairs suitable for use in a CAR of the present disclosure are in some embodiments polypeptides that bind to a different site of the same molecule (referred to herein as a "dimerizer"). In the presence of a dimerizer, both members of the dimerizer-binding pair bind to a different site of the dimerizer and are thus brought into proximity with one another. In some embodiments, binding to the dimerizer is reversible. In some embodiments, binding to the dimerizer is irreversible. In some embodiments, binding to the dimerizer is non-covalent. In some embodiments, binding to the dimerizer is covalent.

Other dimer pairs suitable for use include dimerizer-binding pairs that dimerize upon binding of a first member of a dimer pair to a dimerizing agent, where the dimerizing agent induces a conformational change in the first member of the dimer pair, and where the conformational change allows the first member of the dimer pair to bind (covalently or non-covalently) to a second member of the dimer pair.

Other dimer pairs suitable for use include dimer pairs in which exposure to light (e.g., blue light) induces dimerization of the dimer pair.

Regardless of the mechanism, the dimer pair will dimerize upon exposure to an agent that induces dimerization, where the agent is in some cases a small molecule, or, in other cases, light. Thus, for simplicity, the discussion below referring to "dimerizer-binding pairs" includes dimer pairs that dimerize regardless of the mechanism.

Non-limiting examples of suitable dimers (e.g., dimerizer-binding pairs) include, but are not limited to:
a) FK506 binding protein (FKBP) and FKBP;
b) FKBP and calcineurin catalytic subunit A (CnA);
c) FKBP and cyclophilin;
d) FKBP and FKBP-rapamycin associated protein (FRB);
e) gyrase B (GyrB) and GyrB;
f) dihydrofolate reductase (DHFR) and DHFR;
g) DmrB and DmrB;
h) PYL and ABI;
i) Cry2 and CIB1; and
j) GAI and GID1.

A first or a second member of a dimer (e.g., a dimerizer-binding pair) of a subject CAR can have a length of from about 50 amino acids to about 300 amino acids or more; e.g., a first or a second member of a dimer (e.g., a dimerizer-binding pair) of a subject CAR can have a length of from about 50 aa to about 100 aa, from about 100 aa to about 150 aa, from about 150 aa to about 200 aa, from about 200 aa to about 250 aa, from about 250 aa to about 300 aa, or more than 300 aa.

In some cases, a member of a dimer (e.g., a dimerizer-binding pair) of a subject CAR is derived from FKBP. For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence: MGVQVETISPGDGRTFPKRGQTCVVHYTGMLEDGK KFDSSRDRNKPFKFMLGKQE VIR-GWEEGVAQMSVGQRAKLTISPDYAYGATGHPGIIP-PHATLVFDVELLKLE (SEQ ID NO:12).

In some cases, a member of a dimerizer-binding pair of a subject CAR is derived from calcineurin catalytic subunit A (also known as PPP3CA; CALN; CALNA; CALNA1; CCN1; CNA1; PPP2B; CAM-PRP catalytic subunit; calcineurin A alpha; calmodulin-dependent calcineurin A subunit alpha isoform; protein phosphatase 2B, catalytic subunit, alpha isoform; etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (PP2Ac domain): LEESVALRIITE-GASILRQEKNLLDIDAPVTVCGDIHGQFFDLMKLFE-VGGSPANTRY LFLGDYVDRGYFSIECVLYLWALKI-LYPKTLFLLRGNHECRHLTEYFTFKQECKIKY SERVYDACMDAFDCLPLAALMNQQFLCVHGGL-SPEINTLDDIRKLDRFKEPPAYGP MCDILWSDPLEDFGNEKTQEHFTH-NTVRGCSYFYSYPAVCEFLQHNNLLSILRAHE AQDAGYRMYRKSQTTGFPSLITIFSAPNYLDVYNN-KAAVLKYENNVMNIRQFNCSP HPYWLPNFM (SEQ ID NO:71).

In some cases, a member of a dimer (e.g., a dimerizer-binding pair) is derived from cyclophilin (also known cyclophilin A, PPIA, CYPA, CYPH, PPIase A, etc.). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence: MVNPTVFFDIAVDGEPLGRVSFELFADKVPKTAEN-FRALSTGEKGFGYKGSCFHRII PGFMCQGGDFTRHNGTGGKSIYGEKFEDEN-FILKHTGPGILSMANAGPNTNGSQFFI CTAKTEWL-DGKHVVFGKVKEGMNIVEAMERFGSRNGKTSKKI-TIADCGQLE (SEQ ID NO:72).

In some cases, a member of a dimer (e.g., a dimerizer-binding pair) is derived from MTOR (also known as FKBP-rapamycin associated protein; FK506 binding protein 12-rapamycin associated protein 1; FK506 binding protein 12-rapamycin associated protein 2; FK506-binding protein 12-rapamycin complex-associated protein 1; FRAP; FRAP1; FRAP2; RAFT1; and RAPT1). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence (also known as "Frb": Fkbp-Rapamycin Binding Domain): MILWHEMWHEGLEEASRLYFGERNVKGMFEVLEPL-HAMMERGPQTLKETSFNQA YGRDLMEAQEWCR-KYMKSGNVKDLLQAWDLYYHVFRRISK (SEQ ID NO:14).

In some cases, a member of a dimer (e.g., a dimerizer-binding pair) is derived from GyrB (also known as DNA gyrase subunit B). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 200 amino acids (aa), from about 200 aa to about 300 aa, from about 300 aa to about 400 aa, from about 400 aa to about 500 aa, from about 500 aa to about 600 aa, from about 600 aa to about 700 aa, or from about 700 aa to about 800 aa, of the following GyrB amino acid sequence from *Escherichia coli* (or to the DNA gyrase subunit B sequence from any organism): MSNSYDSSSIKVLKGLDAVRKRPG-MYIGDTDDGTGLHHMVFEVVDNAIDEALAGH CKEIIVTIHADNSVSVQDDGRGIPTGIHPEEGVSAAE-VIMTVLHAGGKFDDNSYKVS GGLHGVGVSVVNALSQKLELVIQREGKIHRQI-YEHGVPQAPLAVTGETEKTGTMV RFWPS-LETFTNVTEFEYEILAKRLRELSFLNSGV-SIRLRDKRDGKEDHFHYEGGIKAF VEYLNKNKTPIHPNIFYFSTEKDG-IGVEVALQWNDGFQENIYCFTNNIPQRDGGTHL AGFRAAMTRTLNAYMDKEGYSKKAKVSATGD-DAREGLIAVVSVKVPDPKFSSQT KDKLVSSEV-KSAVEQQMNELLAEYLLENPTDAKIVVGKIIDAARA-REAARRAREM TRRRKGALDLAGLPGKLADCQERDPALSELYLVEGD-SAGGSAKQGRNRKNQAILPL KGKILN-VEKARFDKMLSSQEVATLITALGCGIGRDEYNPDKL-RYHSIIIMTDADVDG SHIRTLLLTFFYRQMPEIVERGHVYIAQP-PLYKVKKGKQEQYIKDDEAMDQYQISIALDGATLHT-NASAPALAGEALEKLVSEYNATQKMINRMER-RYPKAMLKELIYQPTL TEADLSDEQTVTRWVNALVSELND-KEQHGSQWKFDVHTNAEQNLFEPIVRVRTHG VDTDYPLDHEFITGGEYRRICTLGEKLR-GLLEEDAFIERGERRQPVASFEQALDWLV KESRRGL-SIQRYKGLGEMNPEQLWETTMDPESRRMLRVTVK-DAIAADQLFTTLMG DAVEPRRAFIEENALKAANIDI (SEQ ID NO:73). In some cases, a member of a dimerizer-binding pair comprises an amino acid sequence having at least about 75%, at least about 80%, at least about 85%, at least about 90%, at least about 95%, at least about 98%, or 100% amino acid sequence identity to amino acids 1-220 of the above-listed GyrB amino acid sequence from *Escherichia coli*.

In some cases, a member of a dimer (e.g., a dimerizer-binding pair) is derived from DHFR (also known as dihydrofolate reductase, DHFRP1, and DYR). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence: MVGSLNCIVAVSQNMGIGKNGDLPWPPLRNEFRYFQRMTTTSSVEGKQNLVIMGK KTWFSIPEKNRPLKGRINLVLSRELKEPPQGAHFLSRSLDDALKLTEQPELANKVDM VWIVGGSSVYKEAMNHPGHLKLFVTRIMQDFESDTFFPEIDLEKYKLLPEYPGVLS DVQEEKGIKYKFEVYEKND (SEQ ID NO:74).

In some cases, a member of a dimer (e.g., a dimerizer-binding pair) is derived from the DmrB binding domain (i.e., DmrB homodimerization domain). For example, a suitable dimerizer-binding pair member can comprise an amino acid sequence having at least about 75%, at least about 80%, at least about 85%, at least about 90%, at least about 95%, at least about 98%, or 100% amino acid sequence identity to the following amino acid sequence: MASRGVQVETISPGDGRTFPKRGQTCVVHYTGMLEDGKK VDSSRDRNKPFKFMLG KQEVIRGWEEGVAQMSVGQRAKLTISPDYAYGATGHPGIIPPHATLVFDVELLKLE (SEQ ID NO:75).

In some cases, a member of a dimer (e.g., a dimerizer-binding pair) is derived from a PYL protein (also known as abscisic acid receptor and as RCAR). For example a member of a subject dimerizer-binding pair can be derived from proteins such as those of *Arabidopsis thaliana*: PYR1, RCAR1(PYL9), PYL1, PYL2, PYL3, PYL4, PYL5, PYL6, PYL7, PYL8 (RCAR3), PYL10, PYL11, PYL12, PYL13. For example, a suitable dimerizer-binding pair member can comprise an amino acid sequence having at least about 75%, at least about 80%, at least about 85%, at least about 90%, at least about 95%, at least about 98%, or 100% amino acid sequence identity to any of the following amino acid sequences:

PYL10:
(SEQ ID NO: 76)
MNGDETKKVESEYIKKHHRHELVESQCSSTLVKHIKAPLHLVWSIVRRFD

EPQKYKPFISRCVVQGKKLEVGSVREVDLKSGLPATKSTEVLEILDDNEH

ILGIRIVGGDHRLKNYSSTISLHSETIDGKTGTLAIESFVVDVPEGNTKE

ETCFFVEALIQCNLNSLADVTERLQAESMEKKI.

PYL11:
(SEQ ID NO: 77)
METSQKYHTCGSTLVQTIDAPLSLVWSILRRFDNPQAYKQFVKTCNLSSG

DGGEGSVREVTVVSGLPAEFSRERLDELDDESHVMMISIIGGDHRLVNYR

SKTMAFVAADTEEKTVVVESYVVDVPEGNSEEETTSFADTIVGFNLKSLA

KLSERVAHLKLPYL12:
(SEQ ID NO: 78)
MKTSQEQHVCGSTVVQTINAPLPLVWSILRRFDNPKTFKHFVKTCKLRSG

DGGEGSVREVTVVSDLPASFSLERLDELDDESHVMVISIIGGDHRLVNYQ

SKTTVFVAAEEEKTVVVESYVVDVPEGNTEEETTLFADTIVGCNLRSLAK

LSEKMMELT.

PYL13:
(SEQ ID NO: 79)
MESSKQKRCRSSVVETIEAPLPLVWSILRSFDKPQAYQRFVKSCTMRSGG

GGGKGGEGKGSVRDVTLVSGFPADFSTERLEELDDESHVMVVSIIGGNHR

LVNYKSKTKVVASPEDMAKKTVVVESYVVDVPEGTSEEDTIFFVDNIIRY

NLTSLAKLTKKMMK.

PYL1:
(SEQ ID NO: 80)
MANSESSSSPVNEEENSQRISTLHHQTMPSDLTQDEFTQLSQSIAEFHTY

QLGNGRCSSLLAQRIHAPPETVWSVVRRFDRPQIYKHFIKSCNVSEDFEM

RVGCTRDVNVISGLPANTSRERLDLLDDDRRVTGFSITGGEHRLRNYKSV

TTVHRFEKEEEEERIVVTVVLESYVVDVPEGNSEEDTRLFADTVIRLNLQ

KLASITEAMNRNNNNNNNSSQVR.

PYL2:
(SEQ ID NO: 81)
MSSSPAVKGLTDEEQKTLEPVIKTYHQFEPDPTTCTSLITQRIHAPASVV

WPLIRRFDNPERYKHFVKRCRLISGDGDVGSVREVTVISGLPASTSTERL

EFVDDDHRVLSFRVVGGEHRLKNYKSVTSVNEFLNQDSGKVYTVVLESYT

VDIPEGNTEEDTKMFVDTVVKLNLQKLGVAATSAPMHDDE.

PYL3:
(SEQ ID NO: 82)
MNLAPIHDPSSSSTTTTSSSTPYGLTKDEFSTLDSIIRTHHTFPRSPNTC

TSLIAHRVDAPAHAIVVRFVRDFANPNKYKHFIKSCTIRVNGNGIKEIKV

GTIREVSVVSGLPASTSVEILEVLDEEKRILSFRVLGGEHRLNNYRSVTS

VNEFVVLEKDKKKRVYSVVLESYIVDIPQGNTEEDTRMFVDTVVKSNLQN

LAVISTASPT.

PYL4:
(SEQ ID NO: 83)
MLAVHRPSSAVSDGDSVQIPMMIASFQKRFPSLSRDSTAARFHTHEVGPN

QCCSAVIQEISAPISTVWSVVRRFDNPQAYKHFLKSCSVIGGDGDNVGSL

RQVHVVSGLPAASSTERLDILDDERHVISFSVVGGDHRLSNYRSVTTLHP

SPISGTVVVESYVVDVPPGNTKEETCDFVDVIVRCNLQSLAKIAENTAAE

SKKKMSL.

PYL5:
(SEQ ID NO: 84)
MRSPVQLQHGSDATNGFHTLQPHDQTDGPIKRVCLTRGMHVPEHVAMHHT

HDVGPDQCCSSVVQMIHAPPESVWALVRRFDNPKVYKNFIRQCRIVQGDG

LHVGDLREVMVVSGLPAVSSTERLEILDEERHVISFSVVGGDHRLKNYRS

VTTLHASDDEGTVVVESYIVDVPPGNTEEETLSFVDTIVRCNLQSLARST

NRQ.

PYL6:
(SEQ ID NO: 85)
MPTSIQFQRSSTAAEAANATVRNYPHHHQKQVQKVSLTRGMADVPEHVEL

SHTHVVGPSQCFSVVVQDVEAPVSTVWSILSRFEHPQAYKHFVKSCHVVI

GDGREVGSVREVRVVSGLPAAFSLERLEIMDDDRHVISFSVVGGDHRLMN

YKSVTTVHESEEDSDGKKRTRVVESYVVDVPAGNDKEETCSFADTIVRCN

LQSLAKLAENTSKFS.

PYL7:
(SEQ ID NO: 86)
MEMIGGDDTDTEMYGALVTAQSLRLRHLHHCRENQCTSVLVKYIQAPVHL

VWSLVRRFDQPQKYKPFISRCTVNGDPEIGCLREVNVKSGLPATTSTERL

EQLDDEEHILGINIIGGDHRLKNYSSILTVHPEMIDGRSGTMVMESFVVD

VPQGNTKDDTCYFVESLIKCNLKSLACVSERLAAQDITNSIATFCNASNG

YREKNHTETNL.

PYL8:
(SEQ ID NO: 87)
MEANGIENLTNPNQEREFIRRHHKHELVDNQCSSTLVKHINAPVHIVWSL

VRRFDQPQKYKPFISRCVVKGNMEIGTVREVDVKSGLPATRSTERLELLD

DNEHILSIRIVGGDHRLKNYSSIISLHPETIEGRIGTLVIESFVVDVPEG

NTKDETCYFVEALIKCNLKSLADISERLAVQDTTESRV.

PYL9:
(SEQ ID NO: 88)
MMDGVEGGTAMYGGLETVQYVRTHHQHLCRENQCTSALVKHIKAPLHLVW

SLVRRFDQPQKYKPFVSRCTVIGDPEIGSLREVNVKSGLPATTSTERLEL

LDDEEHILGIKIIGGDHRLKNYSSILTVHPEIIEGRAGTMVIESFVVDVP

QGNTKDETCYFVEALIRCNLKSLADVSERLASQDITQ.

PYR1:
(SEQ ID NO: 89)
MPSELTPEERSELKNSIAEFHTYQLDPGSCSSLHAQRIHAPPELVWSIVR

RFDKPQTYKHFIKSCSVEQNFEMRVGCTRDVIVISGLPANTSTERLDILD

DERRVTGFSIIGGEHRLTNYKSVTTVHRFEKENRIVVTVVLESYVVDMPE

GNSEDDTRMFADTVVKLNLQKLATVAEAMARNSGDGSGSQVT.

In some cases, a member of a dimer (e.g., a dimerizer-binding pair) is derived from an ABI protein (also known as Abscisic Acid-Insensitive). For example a member of a subject dimerizer-binding pair can be derived from proteins such as those of *Arabidopsis thaliana*: ABI1 (Also known as ABSCISIC ACID-INSENSITIVE 1, Protein phosphatase 2C 56, AtPP2C56, P2C56, and PP2C ABI1) and/or ABI2 (also known as P2C77, Protein phosphatase 2C 77, AtPP2C77, ABSCISIC ACID-INSENSITIVE 2, Protein phosphatase 2C ABI2, and PP2C ABI2). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

ABI1:
(SEQ ID NO: 90)
MEEVSPAIAGPFRPFSETQMDFTGIRLGKGYCNNQYSNQDSENGDLMVSL

PETSSCSVSGSHGSESRKVLISRINSPNLNMKESAAADIVVVDISAGDEI

NGSDITSEKKMISRTESRSLFEFKSVPLYGFTSICGRRPEMEDAVSTIPR

FLQSSSGSMLDGRFDPQSAAHFFGVYDGHGGSQVANYCRERMHLALAEEI

AKEKPMLCDGDTWLEKWKKALFNSFLRVDSEIESVAPETVGSTSVVAVVF

PSHIFVANCGDSRAVLCRGKTALPLSVDHKPDREDEAARIEAAGGKVIQW

NGARVFGVLAMSRSIGDRYLKPSIIPDPEVTAVKRVKEDDCLILASDGVW

DVMTDEEACEMARKRILLWHKKNAVAGDASLLADERRKEGKDPAAMSAAE

YLSKLAIQRGSKDNISVVVVDLKPRRKLKSKPLN.

ABI2:
(SEQ ID NO: 91)
MDEVSPAVAVPFRPFTDPHAGLRGYCNGESRVTLPESSCSGDGAMKDSSF

EINTRQDSLTSSSSAMAGVDISAGDEINGSDEFDPRSMNQSEKKVLSRTE

SRSLFEFKCVPLYGVTSICGRRPEMEDSVSTIPRFLQVSSSSLLDGRVTN

GFNPHLSAHFFGVYDGHGGSQVANYCRERMHLALTEEIVKEKPEFCDGDT

WQEKWKKALFNSFMRVDSEIETVAHAPETVGSTSVVAVVFPTHIFVANCG

DSRAVLCRGKTPLALSVDHKPDRDDEAARIEAAGGKVIRWNGARVFGVLA

MSRSIGDRYLKPSVIPDPEVTSVRRVKEDDCLILASDGLWDVMTNEEVCD

LARKRILLWHKKNAMAGEALLPAEKRGEGKDPAAMSAAEYLSKMALQKGS

KDNISVVVVDLKGIRKFKSKSLN.

In some cases, a member of a dimer (e.g., a dimerizer-binding pair) is derived from a Cry2 protein (also known as cryptochrome 2). For example a member of a subject dimer (e.g., a dimerizer-binding pair) can be derived from Cry2 proteins from any organism (e.g., a plant) such as, but not limited to, those of *Arabidopsis thaliana*. For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

Cry2 (*Arabidopsis thaliana*)
(SEQ ID NO: 92)
MKMDKKTIVWFRRDLRIEDNPALAAAAHEGSVFPVFIVVCPEEEGQFYPG

RASRWWMKQSLAHLSQSLKALGSDLTLIKTHNTISAILDCIRVTGATKVV

FNHLYDPVSLVRDHTVKEKLVERGISVQSYNGDLLYEPWEIYCEKGKPFT

SFNSYWKKCLDMSIESVMLPPPWRLMPITAAAEAIVVACSIEELGLENEA

EKPSNALLTRAWSPGWSNADKLLNEFIEKQLIDYAKNSKKVVGNSTSLLS

PYLHFGEISVRHVFQCARMKQIIWARDKNSEGEESADLFLRGIGLREYSR

YICFNFPFTHEQSLLSHLRFFPWDADVDKFKAWRQGRTGYPLVDAGMREL

WATGWMHNRIRVIVSSFAVKFLLLPWKWGMKYFWDTLLDADLECDILGWQ

YISGSIPDGHELDRLDNPALQGAKYDPEGEYIRQWLPELARLPTEWIHHP

WDAPLTVLKASGVELGTNYAKPIVDIDTARELLAKAISRTREAQIMIGAA

-continued
PDEIVADSFEALGANTIKEPGLCPSVSSNDQQVPSAVRYNGSKRVKPEEE

EERDMKKSRGFDERELFSTAESSSSSSVFFVSQSCSLASEGKNLEGIQDS

SDQITTSLGKNGCK.

In some cases, a member of a dimer (e.g., a dimerizer-binding pair) is derived from the CIB1 *Arabidopsis thaliana* protein (also known as transcription factor bHLH63). For example, a suitable dimer (e.g., a dimerizer-binding pair) member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence: MNGAIGGDLLLNFPDMSVLERQRAHLKYLNPTFDS-PLAGFFADSSMITGGEMDSYL STAGLNLPMMY-GETTVEGDSRLSISPET-TLGTGNFKKRKFDTETKDCNEKKKKMT MNRDDLVEEGEEEKSKITEQNNGSTKSIKKM-KHKAKKEENNFSNDSSKVTKELEKT DYIHVRARRGQATDSHSIAERVRREKISER-MKFLQDLVPGCDKITGKAGMLDEIINY VQSLQRQIEFLSMKLAIVNPRPDFDMDDIFAKEV-ASTPMTVVPSPEMVLSGYSHEM VHSGYS-SEMVNSGYLHVNPMQQVNTSSDPLSCFNNGEAPSM WDSHVQNLYGNLG V (SEQ ID NO:93).

In some cases, a member of a dimer (e.g., a dimerizer-binding pair) is derived from the GAI *Arabidopsis thaliana* protein (also known as Gibberellic Acid Insensitive, and DELLA protein GAI). For example, a suitable dimerizer-binding pair member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of the following amino acid sequence: MKRDHHHHHHQDKKTMMMNEEDDGNGMDEL-LAVLGYKVRSSEMADVAQKLEQ LEVMMSNVQED-DLSQLATETVHYNPAELYTWLDSMLTDLNPPSS-NAEYDLKAIPG DAILNQFAIDSASSSNQGGGGDTYTTNK-RLKCSNGVVETTTATAESTRHVVLVDSQ ENGVRLVHALLACAEAVQKENLTVAEALVKQIGFLA-VSQIGAMRKVATYFAEALA RRIYRLSPSQSPI-DHSLSDTLQMHFYETCPYLKFAHF-TANQAILEAFQGKKRVHVIDF SMSQGLQWPALMQALALRPGGPPVFRLTGIGPPAP-DNFDYLHEVGCKLAHLAEAIH VEFEYRGFVANT-LADLDASMLELRPSEIESVAVNSVFELHKLLGRP-GAIDKVLGVV NQIKPEIFTVVEQESNHNSPIFLDRFTESLHYYSTLFD-SLEGVPSGQDKVMSEVYLGK QICNV-VACDGPDRVERHETLSQWRNRFGSAGFAAAHIG-SNAFKQASMLLALFNGG EGYRVEESDGCLMLGWHTRPLIATSAWKLSTN (SEQ ID NO:94).

In some cases, a member of a dimer (e.g., a dimerizer-binding pair) is derived from a GID1 *Arabidopsis thaliana* protein (also known as Gibberellin receptor GID1). For example, a suitable dimer member can comprise an amino acid sequence having at least about 75%, at least about 80%, at least about 85%, at least about 90%, at least about 95%, at least about 98%, or 100% amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, from about 160 aa to about 170 aa, from about 170 aa to about 180 aa, from about 180 aa to about 190 aa, or from about 190 aa to about 200 aa of any of the following amino acid sequences:

GID1A:
(SEQ ID NO: 95)
MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC.

GID1B:
(SEQ ID NO: 96)
MAGGNEVNLNECKRIVPLNTWVLISNFKLAYKVLRRPDGSFNRDLAEFLD

RKVPANSFPLDGVFSFDHVDSTTNLLTRIYQPASLLHQTRHGTLELTKPL

STTEIVPVLIFFHGGSFTHSSANSAIYDTFCRRLVTICGVVVVSVDYRRS

PEHRYPCAYDDGWNALNWVKSRVWLQSGKDSNVYVYLAGDSSGGNIAHNV

AVRATNEGVKVLGNILLHPMFGGQERTQSEKTLDGKYFVTIQDRDWYWRA

YLPEGEDRDHPACNPFGPRGQSLKGVNFPKSLVVVAGLDLVQDWQLAYVD

GLKKTGLEVNLLYLKQATIGFYFLPNNDHFHCLMEELNKFVHSIEDSQSK

SSPVLLTP

GID1C:
(SEQ ID NO: 97)
MAGSEEVNLIESKTVVPLNTWVLISNFKLAYNLLRRPDGTFNRHLAEFLD

RKVPANANPVNGVFSFDVIIDRQTNLLSRVYRPADAGTSPSITDLQNPVD

GEIVPVIVFFHGGSFAHSSANSAIYDTLCRRLVGLCGAVVVSVNYRRAPE

NRYPCAYDDGWAVLKWVNSSSWLRSKKDSKVRIFLAGDSSGGNIVHNVAV

RAVESRIDVLGNILLNPMFGGTERTESEKRLDGKYFVTVRDRDWYWRAFL

PEGEDREHPACSPFGPRSKSLEGLSFPKSLVVVAGLDLIQDWQLKYAEGL

KKAGQEVKLLYLEQATIGFYLLPNNNHFHTVMDEIAAFVNAECQ.

Dimerizers

Dimerizers ("dimerizing agents") that can provide for dimerization of a first member of a dimerizer-binding pair and a second member of a dimerizer-binding pair include, e.g. (where the dimerizer is in parentheses following the dimerizer-binding pair:

a) FKBP and FKBP (rapamycin);
b) FKBP and CnA (rapamycin);
c) FKBP and cyclophilin (rapamycin);
d) FKBP and FRG (rapamycin);
e) GyrB and GyrB (coumermycin);
f) DHFR and DHFR (methotrexate);
g) DmrB and DmrB (AP20187);
h) PYL and ABI (abscisic acid);
i) Cry2 and CIB1 (blue light); and
j) GAI and GID1 (gibberellin).

As noted above, rapamycin can serve as a dimerizer. Alternatively, a rapamycin derivative or analog can be used. See, e.g., WO96/41865; WO 99/36553; WO 01/14387; and Ye et al (1999) *Science* 283:88-91. For example, analogs, homologs, derivatives and other compounds related structurally to rapamycin ("rapalogs") include, among others, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Additional information is presented in, e.g., U.S. Pat. Nos. 5,525,610; 5,310,903 5,362,718; and 5,527,907. Selective epimerization of the C-28 hydroxyl group has been described; see, e.g., WO 01/14387. Additional synthetic dimerizing agents suitable for use as an alternative to rapamycin include those described in U.S. Patent Publication No. 2012/0130076.

Rapamycin has the structure:

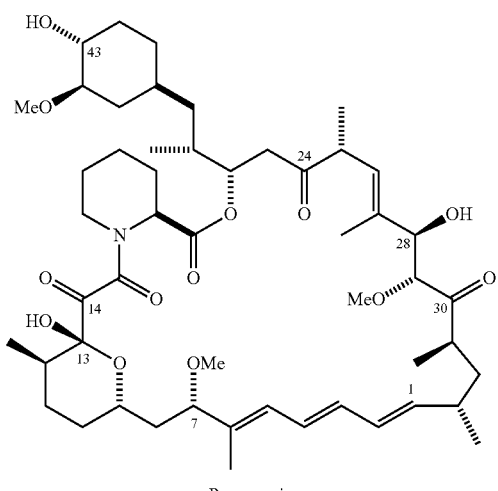

Rapamycin

Suitable rapalogs include e.g.,

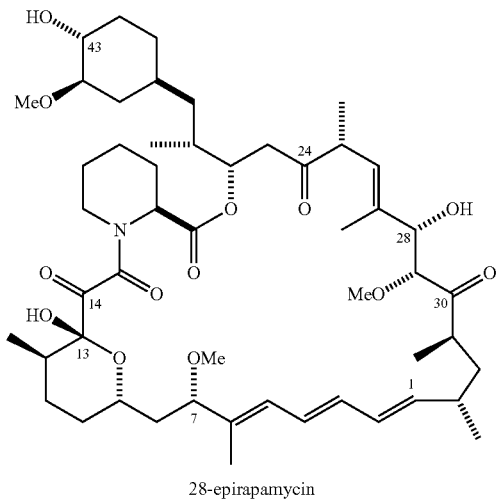

28-epirapamycin

Also suitable as a rapalog is a compound of the formula:

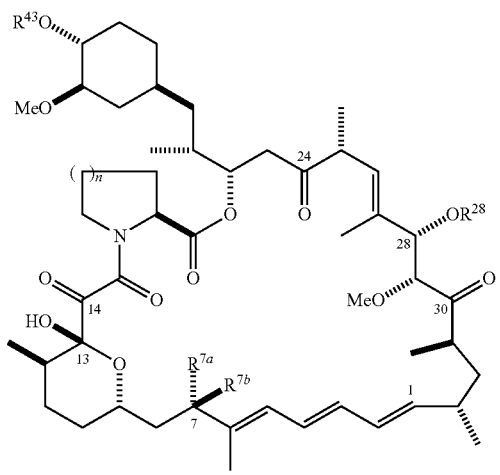

where n is 1 or 2; $R^{28}$ and $R^{43}$ are independently H, or a substituted or unsubstituted aliphatic or acyl moiety; one of $R^{7a}$ and $R^{7b}$ is H and the other is halo, $R^A$, $OR^A$, $SR^A$, —OC(O)$R^A$, —OC(O)NR$^A$R$^B$, —NR$^A$R$^B$, —NR$^B$C(OR)R$^A$, NR$^B$C(O)OR$^A$, —NR$^B$SO$_2$R$^A$, or NR$^B$SO$_2$NR$^A$R$^{B'}$; or $R^{7a}$ and $R^{7b}$, taken together, are H in the tetraene moiety:

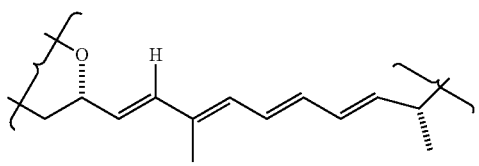

where $R^A$ is H or a substituted or unsubstituted aliphatic, heteroaliphatic, aryl, or heteroaryl moiety and where $R^B$ and $R^{B'}$ are independently H, OH, or a substituted or unsubstituted aliphatic, heteroaliphatic, aryl, or heteroaryl moiety.

As noted above, coumermycin can serve as a dimerizing agent. Alternatively, a coumermycin analog can be used. See, e.g., Farrar et al. (1996) *Nature* 383:178-181; and U.S. Pat. No. 6,916,846.

As noted above, in some cases, the dimerizing agent is methotrexate, e.g., a non-cytotoxic, homo-bifunctional methotrexate dimer. See, e.g., U.S. Pat. No. 8,236,925.

Intracellular Signaling Domain

Intracellular signaling domains suitable for use in a CAR of the present disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

ITAM

Intracellular signaling domains suitable for use in a CAR of the present disclosure include immunoreceptor tyrosine-based activation motif (ITAM)-containing intracellular signaling polypeptides. An ITAM motif is $YX_1X_2L/I$, where $X_1$ and $X_2$ are independently any amino acid (SEQ ID NO:130). In some cases, the intracellular signaling domain of a subject CAR comprises 1, 2, 3, 4, or 5 ITAM motifs. In some cases, an ITAM motif is repeated twice in an intracellular signaling domain, where the first and second instances of the ITAM motif are separated from one another by 6 to 8 amino acids, e.g., $(YX_1X_2L/I)(X_3)_n(YX_1X_2L/I)$, where n is an integer from 6 to 8, and each of the 6-8 $X_3$ can be any amino acid (SEQ ID NO:131). In some cases, the intracellular signaling domain of a subject CAR comprises 3 ITAM motifs.

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain).

In some cases, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences (4 isoforms): MGGLEPCSRLLLLPLLLAVSGLRPVQAQAQSDCSCSTVSPGVLAGIVMGDLVLTVLI ALAVYFLGRLVPRGRGAAEAATRKQRITETESPYOELQGQRSDVYSDLN TQRPYY K (SEQ ID NO:98); MGGLEPCSRLLLLPLLLAVSGLRPVQAQAQSDCSCSTVSPGVLAGIVMGDLVLTVLI ALAVYFLGRLVPRGRGAAEATRKQRITETESPYOELQGQRSDVYSDLNTQRPYYK (SEQ ID NO:99); MGGLEPCSRLLLLPLLLAVSDCSCSTVSPGVLAGIVMGDLVLTVLIALAVYFLGRLV PRGR-GAAEAATRKQRITETESPYOELQGQRSDVYSDLNTQ RPYYK (SEQ ID NO:100); or MGGLEPCSRLLLLPLLLAVSDCSCSTVSPGVLAGIVMGDLVLTVLIALAVYFL-GRLV PRGRGAAEATRKQRITETESPYOELQGQRSDVYSDLNTQRPYYK (SEQ ID NO:101), where the ITAM motifs are in bold and are underlined.

Likewise, a suitable intracellular signaling domain polypeptide can comprise an ITAM motif-containing portion of the full length DAP12 amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: ESPYOELQGQRSDVYSDLNTQ (SEQ ID NO:102), where the ITAM motifs are in bold and are underlined.

In some cases, the intracellular signaling domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular signaling domain polypeptide can comprise an amino acid sequence having at least about 75%, at least about 80%, at least about 85%, at least about 90%, at least about 95%, at least about 98%, or 100% amino acid sequence identity to the following amino acid sequence: MIPAVVLLLLLLVEQAAALGEPQLCYILDAILFLYGIVLTLLYCRLKIQVRKAAITSY EKSDGVYTGLSTRNQETYETLKHEKPPQ (SEQ ID NO:103), where the ITAM motifs are in bold and are underlined.

Likewise, a suitable intracellular signaling domain polypeptide can comprise an ITAM motif-containing portion of the full length FCER1G amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: DGVYTGLSTRNQETYETLKHE (SEQ ID NO:104), where the ITAM motifs are in bold and are underlined.

In some cases, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 170 aa, of either of the following amino acid sequences (2 isoforms): MEHSTFLSGLV- LATLLSQVSPFKIPIEELEDRVFVNCNTSITWVEG-TVGTLLSDITRL DLGKRILDPRGIYRCNGTDIYKD-KESTVQVHYRMCQSCVELDPATVAGIIVTDVIAT LLLALGVFCFAGHET-GRLSGAADTQALLRNDQVYOPLRDRD-DAQYSHLGGNWAR NK (SEQ ID NO:105) or MEHST-FLSGLVLATLLSQVSPFKIPIEELEDRVFVNCNTSITW VEGTVGTLLSDITRL DLGKRILDPRGIYRC-NGTDIYKDKESTVQVHYR-TADTQALLRNDQVYOPLRDRDD AOYSHLGGN-WARNK (SEQ ID NO:106), where the ITAM motifs are in bold and are underlined.

Likewise, a suitable intracellular signaling domain polypeptide can comprise an ITAM motif-containing portion of the full length CD3 delta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: DQVYOPLRDRDDAQYSHLGGN (SEQ ID NO:107), where the ITAM motifs are in bold and are underlined.

In some cases, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 205 aa, of the following amino acid sequence: MQSGTH-WRVLGLCLLSVGVWGQDGNEEMGGITQTPYKVSIS-GTTVILTCPQYPGSE ILWQHNDKNIGGDEDDKNIGS-DEDHLSLKEFSELEQSGYYVCYPRGSKPEDANFYL YLRARVCENCMEMDVMSVATIVIVDICITGGLLLL-VYYWSKNRKAKAKPVTRGAG AGGRQRGQNKER-PPPVPNPDYEPIRKGQRDLYSGLNQRRI (SEQ ID NO:108), where the ITAM motifs are in bold and are underlined.

Likewise, a suitable intracellular signaling domain polypeptide can comprise an ITAM motif-containing portion of the full length CD3 epsilon amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: NPDYEPIRKGQRDLYSGLNQR (SEQ ID NO:109), where the ITAM motifs are in bold and are underlined.

In some cases, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 180 aa, of the following amino acid sequence: MEQGKGLAVLILAIILLQGT-LAQSIKGNHLVKVYDYQEDGSVLLTCDAEAKNITWF KDGKMIGFLTEDKKKWNLGSNAKDPRG-MYQCKGSQNKSKPLQVYYRMCQNCIEL NAATIS-GFLFAEIVSIFVLAVGVYFIAGQDGVRQSR-ASDKQTLLPNDQLYOPLKDRE DDOYSHLQGNQLRRN (SEQ ID NO:110), where the ITAM motifs are in bold and are underlined.

Likewise, a suitable intracellular signaling domain polypeptide can comprise an ITAM motif-containing portion of the full length CD3 gamma amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: DQLYOPLKDREDDQYSHLQGN (SEQ ID NO:111), where the ITAM motifs are in bold and are underlined.

In some cases, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms): MKWKALFTAAILQAQLPITEA-QSFGLLDPKLCYLLDGILFIYGVILTALFLRVKFSRS ADAPAYQQGQNQLYNELNLGRREEYDVLDKRR-GRDPEMGGKPRRKNPQEGLYN ELQKDKMAEAYSEI-GMKGERRRGKGHDGLYOGLSTATKDTY-DALHMQALPPR (SEQ ID NO:112) or MKWKALFTAAILQAQLPITEAQSFGLLDPKLCYLL-DGILFIYGVILTALFLRVKFSRS ADAPAYQQGQNQLY-NELNLGRREEYDVLDKRR-GRDPEMGGKPQRRKNPQEGLY NELQKDKMAEAYSEIGMKGERRRGKGHDGLYOGL-STATKDTYDALHMQALPPR(SEQ ID NO:113), where the ITAM motifs are in bold and are underlined.

Likewise, a suitable intracellular signaling domain polypeptide can comprise an ITAM motif-containing portion of the full length CD3 zeta amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to any of the following amino acid sequences: RVKFSRSADAPAYQQGQNQLYNELNLGR-REEYDVLDKRRGRDPEMGGKPRRKNP QEGLY-NELQKDKMAEAYSEIGMKGERRRGKGHDGLYOGL-STATKDTYDALHMQ ALPPR (SEQ ID NO:18); NQLYNELNLGRREEYDVLDKR (SEQ ID NO:114); EGLYNELQKDKMAEAYSEIGMK (SEQ ID NO:115); or DGLYOGLSTATKDTYDALHMQ (SEQ ID NO:116), where the ITAM motifs are in bold and are underlined.

In some cases, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). For example, a suitable intracellular signaling domain polypeptide can comprise an amino acid sequence having at least about 75%, at least about 80%, at least about 85%, at least about 90%, at least about 95%, at least about 98%, or 100%, amino acid sequence identity to a contiguous stretch of from about 100 amino acids to about 110 amino acids (aa), from about 110 aa to about 115 aa, from about 115 aa to about 120 aa, from about 120 aa to about 130 aa, from about 130 aa to about 150 aa, from about 150 aa to about 200 aa, or from about 200 aa to about 220 aa, of either of the following amino acid sequences (2 isoforms):

MPGGPGVLQALPATIFLLFLL-
SAVYLGPGCQALWMHKVPASLMVSLGEDA
HFQCPHNSSNNANVTWWRVLHGNYTWPPE-
FLGPGEDPNGTLIIQNVNKSHGGIYV
CRVQEGNESYQQSCGTYLRVRQPPPRP-
FLDMGEGTKNRIITAEGIILLFCAVVPGTLL
LFRKRWQNEKLGLDAGDEYEDENLY-
EGLNLDDCSMYEDISRGLQGTYQDVGSLN
IGDVQLEKP (SEQ ID NO:117); or
MPGGPGVLQALPATIFLLFLL-
SAVYLGPGCQALWMHKVPASLMVSLGEDA
HFQCPHNSSNNANVTWWRVLHGNYTWPPE-
FLGPGEDPNEPPPRPFLDMGEGTKNR IITAE-
GIILLFCAVVPGTLLL-
FRKRWQNEKLGLDAGDEYEDENLYEGLNLDDC
SMYE DISRGLQGTYQDVGSLNIGDVQLEKP
(SEQ ID NO:118), where the ITAM motifs are in bold and are underlined.

Likewise, a suitable intracellular signaling domain polypeptide can comprise an ITAM motif-containing portion of the full length CD79A amino acid sequence. Thus, a suitable intracellular signaling domain polypeptide can comprise an amino acid sequence having at least about 75%, at least about 80%, at least about 85%, at least about 90%, at least about 95%, at least about 98%, or 100%, amino acid sequence identity to the following amino acid sequence: ENLYEGLNLDDCSMYEDISRG (SEQ ID NO:119), where the ITAM motifs are in bold and are underlined.

DAP10/CD28

Intracellular signaling domains suitable for use in a CAR of the present disclosure include a DAP10/CD28 type signaling chain.

An example of a DAP10 signaling chain is the amino acid sequence is: RPRRSPAQDGKVYINMPGRG (SEQ ID NO:120). In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence RPRRSPAQDGKVYINMPGRG (SEQ ID NO:120).

An example of a CD28 signaling chain is the amino acid sequence is FWVLVVVGGVLACYSLLVTVAFIIFWVR-SKRSRLLHSDYMNMTPRRPGPTRKHYQ PYAPPRD-FAAYRS (SEQ ID NO:121). In some embodiments, a suitable intracellular signaling domain comprises an amino acid sequence having at least about 85%, at least about 90%, at least about 95%, at least about 98%, or at least about 99%, amino acid sequence identity to the entire length of the amino acid sequence FWVLVVVGGVLACYSLL-VTVAFIIFWVRSKRSRLLHSDYMNMTPRRPGP-TRKHYQ PYAPPRDFAAYRS (SEQ ID NO:121).

ZAP70

Intracellular signaling domains suitable for use in a CAR of the present disclosure include a ZAP70 polypeptide, e.g., a polypeptide comprising an amino acid sequence having at least about 85%, at least about 90%, at least about 95%, at least about 98%, at least about 99%, or 100%, amino acid sequence identity to a contiguous stretch of from about 300 amino acids to about 400 amino acids, from about 400 amino acids to about 500 amino acids, or from about 500 amino acids to 619 amino acids, of the following amino acid sequence:

MPDPAAHLPFFYGSISRAEAEEHLKLAGMADG-
LFLLRQCLRSLGGYVLSLVHDVRF HHFPIER-
QLNGTYAIAGGKAHCGPAELCEFYSRDPDG-
LPCNLRKPCNRPSGLEPQPG
VFDCLRDAMVRDYVRQTWKLEGEALEQAI-
ISQAPQVEKLIATTAHERMPWYHSSL TREE-
AERKLYSGAQTDGKFLLRPRKEQGTY-
ALSLIYGKTVYHYLISQDKAGKYCIP
EGTKFDTLWQLVEYLKLKADGLIYCLKEACPNS-
SASNASGAAAPTLPAHPSTLTHP
QRRIDTLNSDGYTPEPARIT-
SPDKPRPMPMDTSVYESPYSDPEELKDKKLFLK
RDNL LIADIEL-
GCGNFGSVRQGVYRMRKKQIDVAI-
KVLKQGTEKADTEEMMREAQIMHQ
LDNPYIVRLIGVCQAEALMLVMEMAGGG-
PLHKFLVGKREEIPVSNVAELLHQVSM
GMKYLEEKNFVHRDLAARNVLLVNRHYAKIS-
DFGLSKALGADDSYYTARSAGKW PLKWY-
APECINFRKFSSRSDVWSYGVTMWEAL-
SYGQKPYKKMKGPEVMAFIEQG
KRMECPPECPPELYALMSDCWIYKWEDRPD-
FLTVEQRMRACYYSLASKVEGPPGS
TQKAEAACA (SEQ ID NO:36).

Additional Sequences

The first and/or the second polypeptide of a subject CAR can further include one or more additional polypeptide domains, where such domains include, but are not limited to, a signal sequence; an epitope tag; an affinity domain; and a polypeptide that produces a detectable signal.

Signal Sequences

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc.

Epitope Tag

Suitable epitope tags include, but are not limited to, hemagglutinin (HA; e.g., YPYDVPDYA (SEQ ID NO:122); FLAG (e.g., DYKDDDDK (SEQ ID NO:123); c-myc (e.g., EQKLISEEDL; SEQ ID NO:4), and the like.

Affinity Domain

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include His5 (HHHHH) (SEQ ID NO:124), HisX6 (HHHHHH) (SEQ ID NO:125), C-myc (EQKLISEEDL) (SEQ ID NO:4), Flag (DYKDDDDK) (SEQ ID NO:123), StrepTag (WSHPQFEK) (SEQ ID NO:126), hemagluttinin, e.g., HA Tag (YPYDVPDYA) (SEQ ID NO:122), GST, thioredoxin, cellulose binding domain, RYIRS (SEQ ID NO:127), Phe-His-His-Thr (SEQ ID NO:128), chitin binding domain, S-peptide, T7 peptide, SH2 domain, C-end RNA tag, WEAAAREACCRECCARA (SEQ ID NO:129), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Detectable Signal-Producing Polypeptides

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recombination of Sequences

In certain instances, sequences of the polypeptides of a CAR, e.g., CAR domains, may be rearranged or deleted in a cell through the use of site-specific recombination technology. In certain embodiments, the cellular activation-related response to a particular CAR can be changed by site-specific recombination, e.g., a first intracellular signaling domain of a CAR eliciting a first activation-related response may be exchanged for a second intracellular signaling domain eliciting a second activation-related response. In certain instances, the response to a particular dimerizer of a CAR can be changed by site-specific recombination, e.g., a first dimerizer-binding pair causing the dimerization of a CAR in the presence of a first dimerizer may be exchanged for a second dimerizer-binding pair causing the dimerization of the CAR in the presence of a second dimerizer. As will be clear to one skilled in the art, site-specific recombination can be used in a cell to exchange any domain or sequence of a CAR with any other domain or sequence as disclosed herein. As will also be clear to one skilled in the art, site-specific recombination can be used in a cell to delete any domain or sequence of a CAR. Such exchange and excision of sequences and domains is known in the art, see, e.g., domain switching in signalobodies as described in Tone et al. (2013) *Biotechnology and Bioengineering,* 3219-3226, the disclosure of which is disclosed herein by reference. Mechanisms and requirements for performing site-specific recombination in vivo are also well known in the art, see, e.g., Grindley et al. (2006) *Annual Review of Biochemistry,* 567-605 and Tropp (2012) Molecular Biology (Jones & Bartlett Publishers, Sudbury, MA), the disclosures of which are incorporated herein by reference.

Nucleic Acids

The present disclosure provides a nucleic acid that comprises a nucleotide sequence encoding the first and/or the second polypeptide of a heterodimeric, conditionally active CAR of the present disclosure. A nucleic acid comprising a nucleotide sequence encoding the first and/or the second polypeptide of a heterodimeric, conditionally active CAR of the present disclosure will in some embodiments be DNA, including, e.g., a recombinant expression vector. A nucleic acid comprising a nucleotide sequence encoding the first and/or the second polypeptide of a heterodimeric, conditionally active CAR of the present disclosure will in some embodiments be RNA, e.g., in vitro synthesized RNA.

In some cases, a nucleic acid of the present disclosure comprises a nucleotide sequence encoding only the first polypeptide (and not the second polypeptide) of a heterodimeric, conditionally active CAR of the present disclosure. In some cases, a nucleic acid of the present disclosure comprises a nucleotide sequence encoding only the second polypeptide (and not the first polypeptide) of a heterodimeric, conditionally active CAR of the present disclosure. In some cases, a nucleic acid of the present disclosure comprises a nucleotide sequence encoding both the first polypeptide and the second polypeptide of a heterodimeric, conditionally active CAR of the present disclosure.

In some cases, a subject nucleic acid provides for production of a CAR of the present disclosure, e.g., in a mammalian cell. In other cases, a subject nucleic acid provides for amplification of the CAR-encoding nucleic acid.

A nucleotide sequence encoding the first and/or the second polypeptide of a CAR of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., PNAS (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) Annual Review of Biochemistry, 567-605 and Tropp (2012) Molecular Biology (Jones & Bartlett Publishers, Sudbury, MA), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) Proc. Natl. Acad. Sci. USA 90:7739; and Marodon et al. (2003) Blood 101:3416. As another example, a CD8 gene promoter can be used. NK cell-specific expression can be achieved by use of an Ncr1 (p46) promoter; see, e.g., Eckelhart et al. (2011) Blood 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367); a tet promoter (see, e.g., Hillen,W. and Wissmann,A. (1989) In Saenger,W. and Heinemann,U. (eds), Topics in Molecular and Structural Biology, Protein-Nucleic Acid Interaction. Macmillan, London, UK, Vol. 10, pp. 143-162); an SP6 promoter (see, e.g., Melton et al. (1984) Nucl. Acids Res. 12:7035); and the like. Suitable strong promoters for use in prokaryotes such as Escherichia coli include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a subject CAR can be present in an expression vector and/or a cloning vector. Where a subject CAR comprises two separate polypeptides, nucleotide sequences encoding the two polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding the first and/or the second polypeptide of a heterodimeric, conditionally active CAR of the present disclosure will in some embodiments be RNA, e.g., in vitro synthesized RNA. Methods for in vitro synthesis of RNA are known in the art; any known method can be used to synthesize RNA comprising a nucleotide sequence encoding the first and/or the second polypeptide of a heterodimeric, conditionally active CAR of the present disclosure. Methods for introducing RNA into a host cell are known in the art. See, e.g., Zhao et al. (2010) Cancer Res. 15:9053. Introducing RNA comprising a nucleotide sequence encoding the first and/or the second polypeptide of a heterodimeric, conditionally active CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding the first and/or the second polypeptide of a heterodimeric, conditionally active CAR of the present disclosure.

Cells

The present disclosure provides a mammalian cell that is genetically modified to produce a heterodimeric, conditionally active CAR of the present disclosure.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

Methods of Activating an Immune Cell

The present disclosure provides methods of activating an immune cell in vitro, in vivo, or ex vivo. The methods generally involve contacting an immune cell (in vitro, in vivo, or ex vivo) with a dimerizing agent and an antigen, where the immune cell is genetically modified to produce a heterodimeric, conditionally active CAR of the present disclosure. In the presence of the dimerizing agent and the antigen, the heterodimeric, conditionally active CAR dimerizes and activates the immune cell, thereby producing an activated immune cell. Immune cells include, e.g., a cytotoxic T lymphocyte, an NK cell, a $CD4^+$ T cell, a T regulatory (Treg) cell, etc.

Contacting the genetically modified immune cell (e.g., a T lymphocyte, an NK cell) with a dimerizing agent and a second member of a specific binding pair (e.g., an antigen, a ligand, a receptor) can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the second member of a specific binding pair and/or the dimerizing agent. Cytokines whose production can be increased include, but are not limited to, IL-2 and IFN-γ.

Contacting the genetically modified immune cell (e.g., a T lymphocyte, an NK cell) with a dimerizing agent and an antigen can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the antigen and/or the dimerizing agent. Cytokines whose production can be increased include, but are not limited to, IL-2 and IFN-γ.

Contacting a genetically modified cytotoxic cell (e.g., cytotoxic T lymphocyte) with a dimerizing agent and a second member of a specific binding pair (e.g., an antigen, a ligand, a receptor) can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the dimerizing agent.

Contacting a genetically modified cytotoxic cell (e.g., cytotoxic T lymphocyte) with a dimerizing agent and an antigen can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the dimerizing agent.

In other embodiments, e.g., depending on the host immune cell, contacting a genetically modified host cell with a dimerizing agent and an antigen can increase or decrease cell proliferation, cell survival, cell death, and the like.

Methods of Generating a Conditionally Activatable Cell

The present disclosure provides a method of generating a conditionally activatable cell. The method generally involves genetically modifying a mammalian cell with an expression vector, or an RNA (e.g., in vitro transcribed RNA), comprising nucleotide sequences encoding a heterodimeric, conditionally active CAR of the present disclosure. The genetically modified cell is conditionally activatable in the presence of: a) an antigen to which the first polypeptide of the CAR binds; and b) a dimerizer (a dimerizing agent). The genetic modification can be carried out in vivo, in vitro, or ex vivo. The cell can be an immune cell (e.g., a T lymphocyte or NK cell), a stem cell, a progenitor cell, etc.

In some cases, the genetic modification is carried out ex vivo. For example, a T lymphocyte, a stem cell, or an NK cell is obtained from an individual; and the cell obtained from the individual is genetically modified to express a CAR of the present disclosure. The genetically modified cell is conditionally activatable in the presence of: a) an antigen to which the first polypeptide of the CAR binds; and b) a dimerizer. In some cases, the genetically modified cell is activated ex vivo. In other cases, the genetically modified cell is introduced into an individual (e.g., the individual from whom the cell was obtained); and the genetically modified cell is activated in vivo, e.g., by administering to the individual a dimerizer. For example, where the antigen is present on the surface of a cell in the individual, there is no need to administer the antigen. The genetically modified cell comes into contact with the antigen present on the surface of a cell in the individual; and, upon administration to the individual of a dimerizer, the genetically modified cell is activated. For example, where the genetically modified cell is a T lymphocyte, the genetically modified cell can exhibit cytotoxicity toward a cell that presents an antigen on its surface to which the CAR binds.

Treatment Methods

The present disclosure provides various treatment methods using a subject CAR.

Cytotoxicity Methods

A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The antigen-binding domain of the CAR binds to an antigen present on the surface of a target cell.

Target cells include, but are not limited to, cancer cells. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cancer cell, and mediates killing of the target cell.

The present disclosure provides a method of treating cancer in an individual having a cancer, the method comprising: i) genetically modifying T lymphocytes obtained from the individual with an expression vector comprising nucleotide sequences encoding the heterodimeric, conditionally active CAR of the present disclosure, where the antigen-binding domain of the heterodimeric, conditionally active CAR is specific for an epitope on a cancer cell in the individual, and where the genetic modification is carried out ex vivo; ii) introducing the genetically modified T lymphocytes into the individual; and iii) administering to the individual an effective amount of a dimerizing agent, wherein the dimerizing agent induces dimerization of the heterodimeric, conditionally active CAR, wherein said dimerization provides for activation of the genetically modified T lymphocytes and killing of the cancer cell, thereby treating the cancer.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Immunomodulatory Methods

A subject method can also be used to treat inflammatory conditions and autoimmune disease. A subject CAR is expressed in a T-helper cell or a Tregs for use in an immunomodulatory method. Immunomodulatory methods include, e.g., enhancing an immune response in a mammalian subject toward a pathogen; enhancing an immune response in a subject who is immunocompromised; reducing an inflammatory response; reducing an immune response in a mammalian subject to an autoantigen, e.g., to treat an autoimmune disease; and reducing an immune response in a mammalian subject to a transplanted organ or tissue, to reduce organ or tissue rejection.

Where the method involves reducing an immune response to an autoantigen, the antigen used to activate the CAR is an autoantigen. Where the method involves reducing an immune response to a transplanted organ or tissue, the antigen used to activate the CAR is an antigen specific to the transplanted organ.

Formulations, Dosages, and Routes of Administration

As discussed above, a treatment method of the present disclosure involves administration to an individual in need thereof of an effective amount of a dimerizer agent, and may also involve administration of an antigen.

An "effective amount" of a dimerizer agent is in some cases an amount that, when administered in one or more doses to an individual in need thereof, increases the level of cytotoxic activity of a T lymphocyte expressing a subject CAR by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the T lymphocyte in the absence of the dimerizing agent.

An "effective amount" of a dimerizer agent is in some cases an amount that, when administered in one or more doses to an individual in need thereof, increases the level of cytotoxic activity of an NK cell expressing a subject CAR by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the NK cell in the absence of the dimerizing agent.

An "effective amount" of a dimerizer agent is in some cases an amount that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the dimerizing agent.

In some embodiments, an effective amount of a dimerizer is an amount that, when administered alone (e.g., in monotherapy) or in combination (e.g., in combination therapy) with one or more additional therapeutic agents, in one or more doses, is effective to reduce one or more of tumor growth rate, cancer cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, cancer cell number, or tumor mass in the absence of treatment with the dimerizer.

Formulations

In the subject methods, a dimerizer can be administered to the host using any convenient means capable of resulting in the desired therapeutic effect or diagnostic effect. Thus, the dimerizer can be incorporated into a variety of formulations for therapeutic administration. More particularly, a dimerizer can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a dimerizer can be administered in the form of their pharmaceutically acceptable salts, or they may also be used alone or in appropriate association, as well as in combination, with other pharmaceutically active compounds. The following methods and excipients are merely exemplary and are in no way limiting.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a dimerizer adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

For oral preparations, a dimerizer can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A dimerizer can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a dimerizer are prepared by mixing the dimerizer having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration; see also Chen (1992) Drug Dev Ind Pharm 18, 1311-54.

The term "unit dosage form," as used herein, refers to physically discrete units suitable as unitary dosages for human and animal subjects, each unit containing a predetermined quantity a dimerizer calculated in an amount sufficient to produce the desired effect in association with a pharmaceutically acceptable diluent, carrier or vehicle. The specifications for a given dimerizer may depend on the particular dimerizer employed and the effect to be achieved, and the pharmacodynamics associated with each dimerizer in the host.

In some embodiments, a dimerizer is formulated in a controlled release formulation. Sustained-release preparations may be prepared using methods well known in the art. Suitable examples of sustained-release preparations include semipermeable matrices of solid hydrophobic polymers containing the dimerizer in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(–)-3-hydroxybutyric acid. Possible loss of biological activity may be prevented by using appropriate additives, by controlling moisture content and by developing specific polymer matrix compositions.

Dosages

A suitable dosage can be determined by an attending physician or other qualified medical personnel, based on various clinical factors. As is well known in the medical arts, dosages for any one patient depend upon many factors, including the patient's size, body surface area, age, the particular dimerizer to be administered, sex of the patient, time, and route of administration, general health, and other drugs being administered concurrently. A dimerizer may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 g to 10 mg per kilogram of body weight per minute.

Those of skill will readily appreciate that dose levels can vary as a function of the specific dimerizer, the severity of the symptoms and the susceptibility of the subject to side effects. Preferred dosages for a given compound are readily determinable by those of skill in the art by a variety of means.

Routes of Administration

A dimerizer is administered to an individual using any available method and route suitable for drug delivery, including in vivo and ex vivo methods, as well as systemic and localized routes of administration.

Conventional and pharmaceutically acceptable routes of administration include intratumoral, peritumoral, intramuscular, intratracheal, intracranial, subcutaneous, intradermal, topical application, intravenous, intraarterial, rectal, nasal, oral, and other enteral and parenteral routes of administration. Routes of administration may be combined, if desired, or adjusted depending upon the dimerizer and/or the desired effect. A dimerizer can be administered in a single dose or in multiple doses. In some embodiments, a dimerizer is administered orally. In some embodiments, a dimerizer is administered via an inhalational route. In some embodiments, a dimerizer is administered intranasally. In some embodiments, a dimerizer is administered locally. In some embodiments, a dimerizer is administered intratumorally. In some embodiments, a dimerizer is administered peritumorally. In some embodiments, a dimerizer is administered intracranially. In some embodiments, a dimerizer is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, peritumoral, and intravenous routes, i.e., any route of administration other than through the alimentary canal. Parenteral administration can be carried to effect systemic or local delivery of a dimerizer. Where systemic delivery is desired, administration typically involves invasive or systemically absorbed topical or mucosal administration of pharmaceutical preparations.

A dimerizer can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

In some embodiments, a dimerizer is administered by injection and/or delivery, e.g., to a site in a brain artery or directly into brain tissue. A dimerizer can also be administered directly to a target site e.g., by direct injection, by implantation of a drug delivery device such as an osmotic pump or slow release particle, by biolistic delivery to the target site, etc.

Combination Therapy

In some embodiments, a dimerizer is administered as an adjuvant therapy to a standard cancer therapy. Standard cancer therapies include surgery (e.g., surgical removal of cancerous tissue), radiation therapy, bone marrow transplantation, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™) Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), $^{90}$Y-labelled ibritumomab tiuxetan (Zevalin™), I-labelled tositumoma (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le$^y$, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α.; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Subjects Suitable for Treatment

A variety of subjects are suitable for treatment with a subject method of treating cancer. Suitable subjects include any individual, e.g., a human or non-human animal who has cancer, who has been diagnosed with cancer, who is at risk for developing cancer, who has had cancer and is at risk for recurrence of the cancer, who has been treated with an agent other than a dimerizer for the cancer and failed to respond to such treatment, or who has been treated with an agent other than a dimerizer for the cancer but relapsed after initial response to such treatment.

Subjects suitable for treatment with a subject immunomodulatory method include individuals who have an autoimmune disorder; individuals who are organ or tissue transplant recipients; and the like; individuals who are immunocompromised; and individuals who are infected with a pathogen.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); i.v., intravenous(ly); and the like.

Example 1: Generation of CAR

Materials and Methods

The anti-human CD19 scFv was selected as the antigen recognition domain in CARs throughout the design optimization process. FIGS. 18A and 18B summarize the molecular structure of each CAR consisting of two numerically identified polypeptides. All membrane-anchored polypeptides are di-sulfide bonded homo-dimers. The membrane-anchored polypeptides are depicted as monomers for graphical simplicity.

Generation of CAR Constructs

Sequence encoding the anti-human CD19 scFv was cloned from a construct. The human 4-1BB co-stimulation and CD3 zeta ITAM signaling chains were cloned from cDNAs supplied by Open Biosystems. FKBP- and FRB-encoding sequences were cloned from plasmids supplied by Addgene.

Standard molecular cloning techniques (polymerase chain reaction (PCR), restriction digestion, ligation, etc.) were applied to generate lentiviral expression plasmids.

Effector and Target Cell Culturing Conditions

Human primary CD8+ T cells were isolated from anonymous donor's blood after apheresis (Trima residuals from Blood Centers of the Pacific, San Francisco, CA) by negative selection using RosetteSep Human CD8+ T Cell Enrichment Cocktail (STEMCELL Technologies #15063) as approved by University Institutional Review Board. Cells were cultured in human T cell medium, consisting of X-VIVO15 (Lonza #04-418Q), 5% human AB serum (Valley Biomedical Inc., #HP1022), 10 mM N-acetyl L-Cysteine (Sigma-Aldrich #A9165) and 100 IU/mL recombinant human IL-2 (NCI/BRB Preclinical Repository). A Jurkat cell line expressing the Green Fluorescent Protein (GFP) upon NFAT activation was maintained in RPMI-1640 medium supplemented with 10% fetal bovine serum (FBS), penicillin and streptomycin. K562 target cells from U. Penn were cultured in IMDM supplemented with 10% FBS.

Effector and Target Cell Engineering with Lentivirus

Pantropic VSV-G pseudotyped lentivirus was produced from *Lenti*-X 293T cells (Clontech Laboratories #632180) co-transfected with a pHR' SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Twenty four hours prior to viral transduction, primary human T cells were activated using the human T-Activator CD3/CD28 Dynabeads (Life Technologies #111-31D) at a 1:3 cell:bead ratio. Jurkat and K562 cells were split 1-2 days in advance to ensure that cultures would be in log phase at the time of transduction. Transduced Jurkat and K562 cells were cultured for at least 7 days before experiments were conducted. Primary T cells were maintained at ~10^6/mL in human T cell medium for about two weeks until cells returned to a resting state. Expression levels of CARs encoded in the lentiviral constructs were quantified by detecting either fluorophore-conjugated antibodies or fluorescent reporter proteins using a flow cytometer.

Quantitation of IL-2 Production and NFAT Activity

Jurkat CD4+ T cells expressing CARs were mixed with cognate or non-cognate K562 target cells from U. Penn at a 1:2 effector:target ratio. The rapalog A/C Heterodimerizer (Clontech Laboratories #635055) were serially diluted in medium and added to reaction mixtures. After 20~24 hours of incubation, medium supernatants were collected and analyzed with BD OptEIA Human IL-2 ELISA Set (BD Biosciences #555190). Flow cytometry was performed to quantify NFAT-dependent GFP reporter expression in Jurkat cells as a separate indicator for CAR activity.

Flow Cytometry-Based Re-Directed Cytotoxicity Assay

The cognate and non-cognate K562 target cells were engineered to express distinct fluorescent proteins so that both cell types in a mixture could be simultaneously quantified by flow cytometry. The target cell types were mixed at a 1:1 ratio and co-incubated with human primary CD8+ effector T cells at a 5:2 effector:target ratio. 100 IU/mL human IL-2 and varying amounts of the rapalog (Clontech Laboratories #635055) were added to reaction mixtures. After 24 hours of incubation, samples were centrifuged at 400 g for 5 minutes. Pelleted cells were resuspended in wash buffer (PBS+0.5% BSA+0.1% sodium azide) and fixed with an equal volume of BD Cytofix (BD cat #554655) prior to flow cytometry. Ratios of the surviving cognate target cells to non-cognate target cells were calculated for each sample to enumerate re-directed cytotoxic activities of the effector cells.

Results

IL-2 production elicited by the various CAR constructs was assessed. The data are presented in FIG. 12.

FIG. 12. IL-2 production triggered by five On-switch CAR variants. Effector=human CD4+ Jurkat T cells engineered with CARs. Target=K562 cell lines with or without the cognate CD19 antigen. Amounts of secreted IL-2 by effector cells were quantified by enzyme-linked immunosorbent assay (ELISA).

Figure 13:
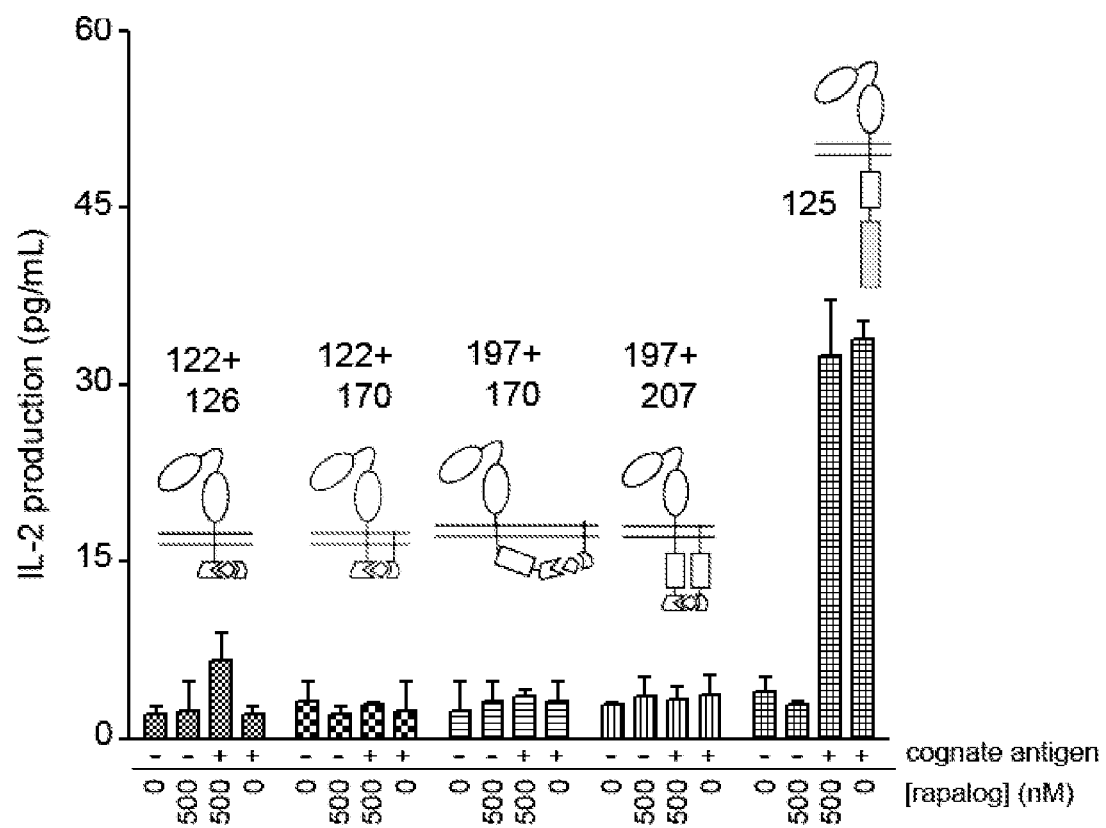
FIG. 13 depicts IL-2 production by control Jurkat lines.

FIG. 13. IL-2 production by control Jurkat lines in the same experiment as that described in FIG. 12. Construct "125" encodes a conventional control currently used in clinical trials.

Figure 14:
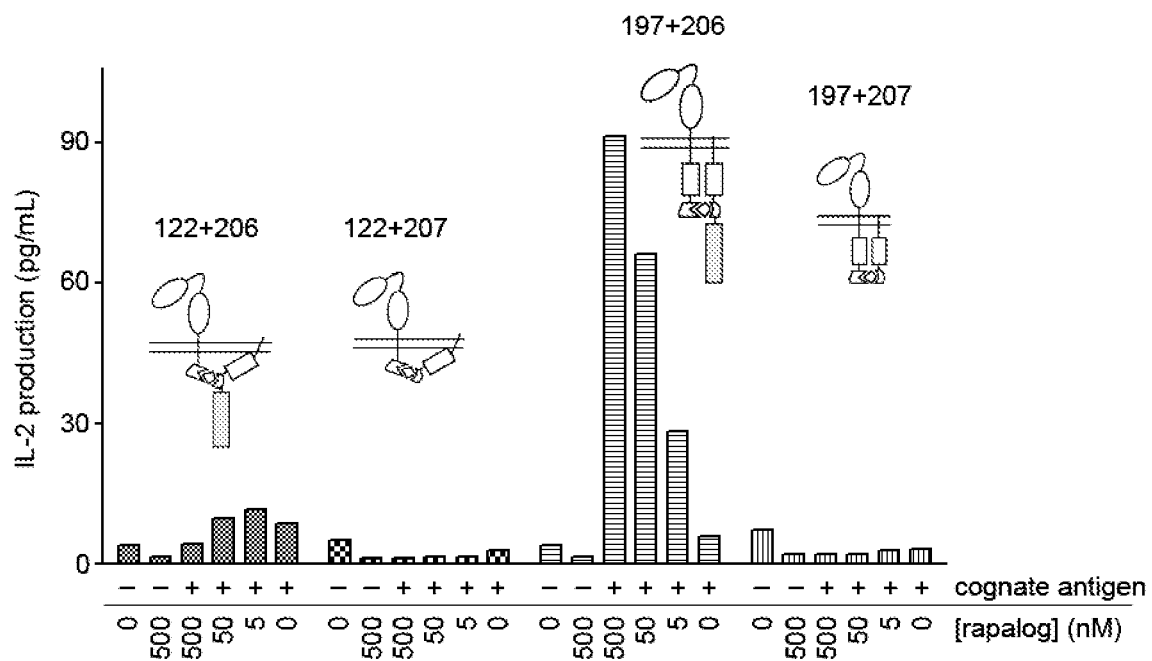
FIG. 14 depicts a comparison between CAR constructs "122+206" and "197+206".

FIG. 14. Comparison between "122+206" and "197+206" in a separate experiment under conditions identical to those described in FIG. 12.

Figure 15:
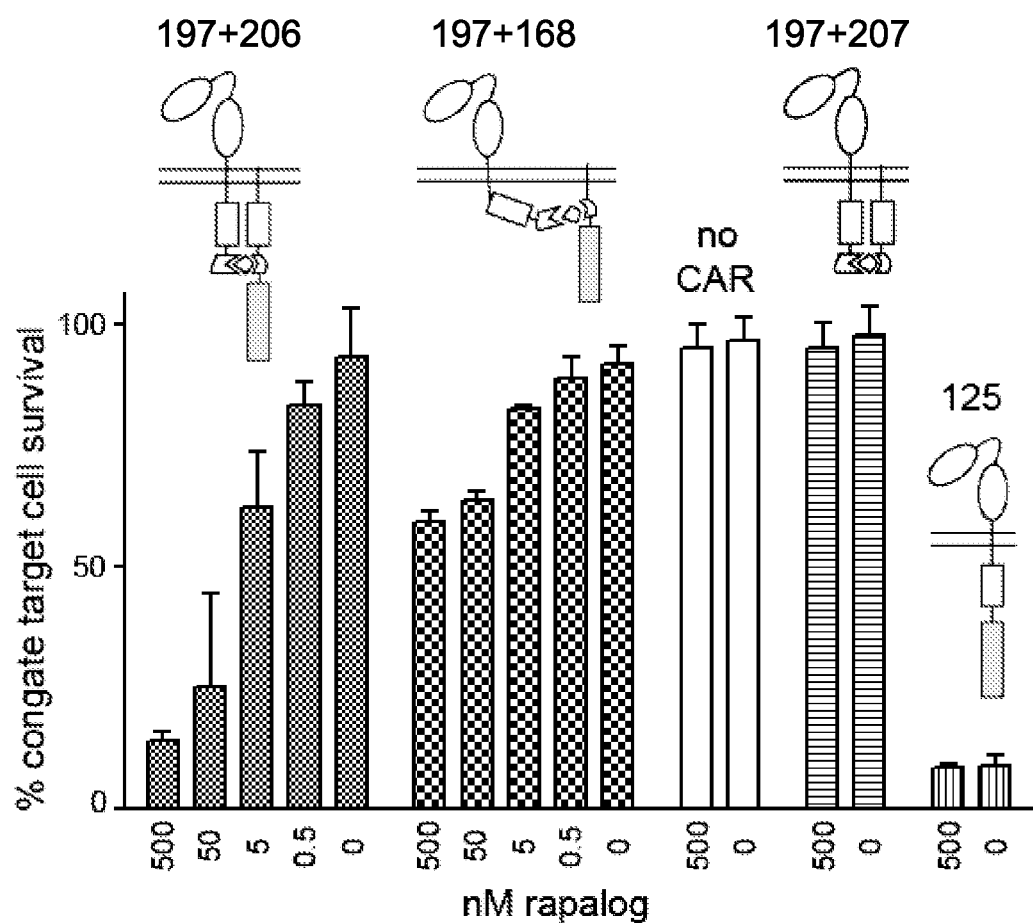
FIG. 15 depicts cytotoxicity data with the On-switch CAR "197+206."

FIG. 15 demonstrates pharmacologically titratable cytoxicity conferred by the On-switch CAR "197+206" In the presence of the small molecule rapalog, the CAR effectively mediates re-directed cytotoxicity towards cognate target cells. At high dosages of rapalog, this On-switch CAR can signal as strongly as the "125" conventional CAR. Effector=human primary CD8+ T cells engineered with CARs or a control vector. Target=fluorescent derivatives of K562 cell lines expressing either the cognate human CD19 antigen or the non-cognate human mesothelin antigen.

Figure 16:
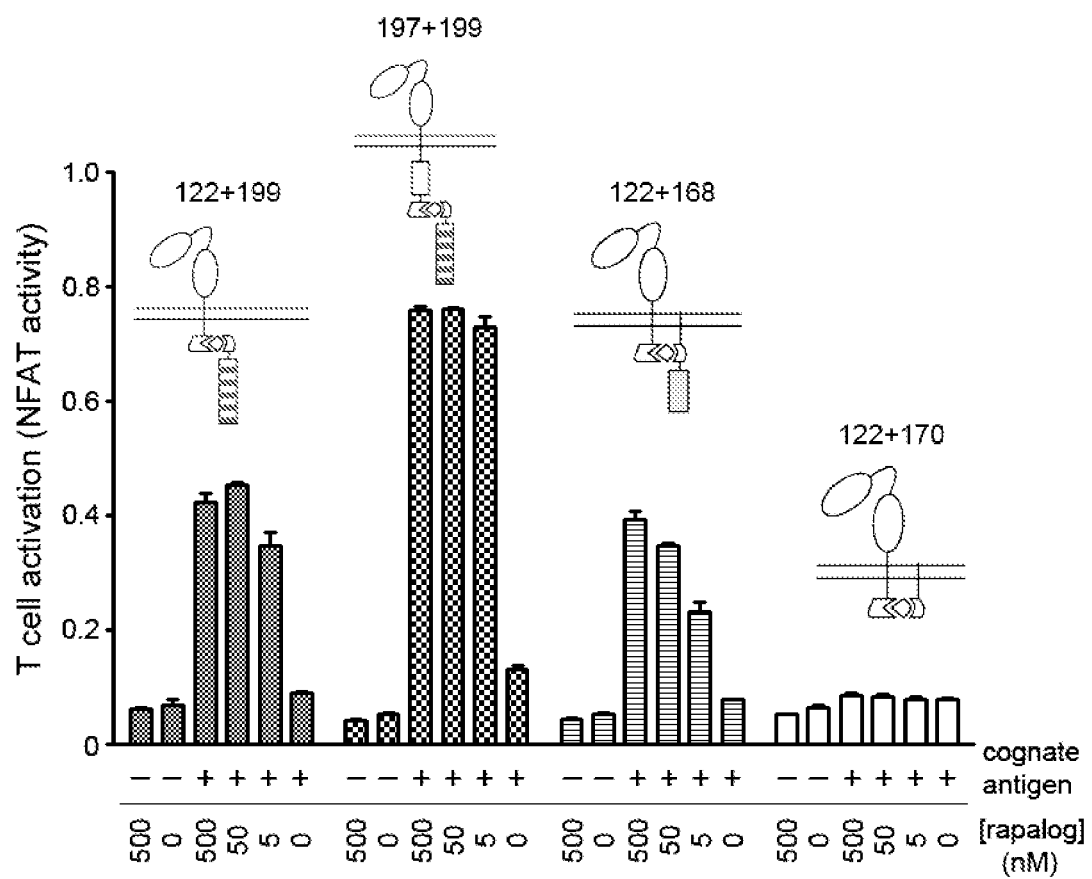
FIG. 16 depicts T cell activation data using CAR constructs "122+199"; "197+199"; and "122+168."

FIG. 16 depicts data for CARs constructed with the cytoplasmic tyrosine kinase Zap70 from the T cell receptor pathway as the intracellular signaling domain.

FIG. 16 shows data from Jurkat cells engineered with several variants of On-switch CARs. The engineered Jurkat cells were co-incubated with K562 target cells with or without the cognate antigen (CD19) and the indicated concentrations of rapalog. As a CAR component, the Zap70 kinase (first and second structures from left featuring "199") was as effective as the ITAM (third structure from left featuring "168") in activating NFAT function. Addition of the 4-1BB signaling domain increased surface expression of the antigen recognition portion of the receptor and led to stronger signaling by "197+199". A non-signaling CAR (far-right) was included as a negative control.

Example 2: CARs Targeting Mesothelin

Materials and Methods

Figure 19A:
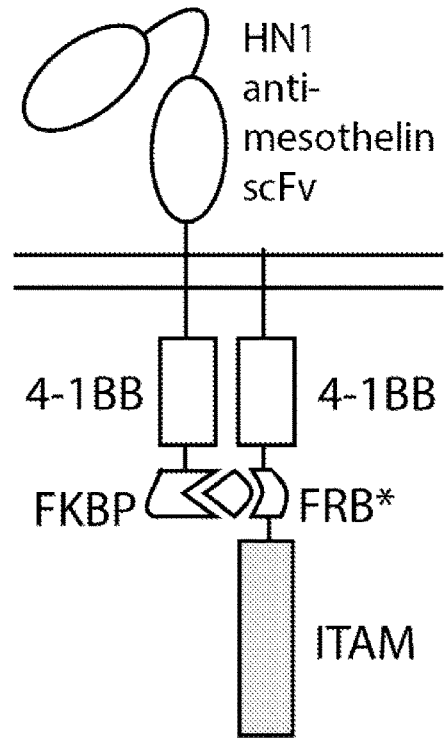
FIGS. 19A-G depict IL-2 production triggered by 3 different On-switch CAR variants recognizing human mesothelin.
Figure 19B:
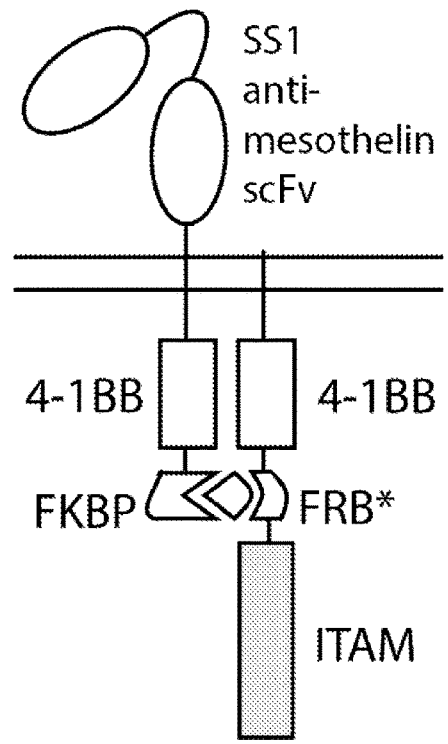
Figure 19C:
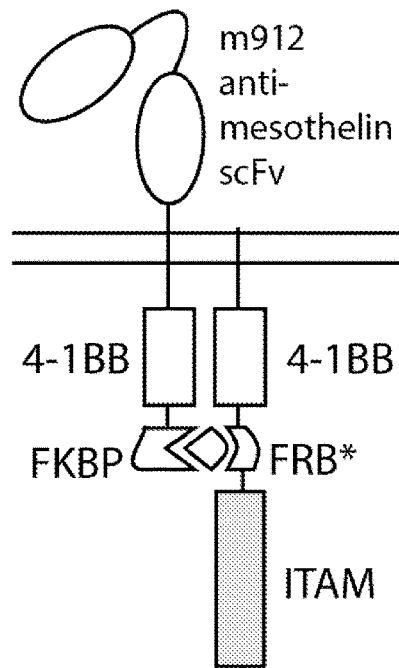

A number of chimeric antigen receptor constructs were made and tested. The constructs shown here encode three different anti-human mesothelin scFv as the antigen recognition domains. FIGS. 19A, 19B, and 19C summarize the molecular structure of each anti-human mesothelin CAR, with each CAR comprising two polypeptides. The intercellular portion of each anti-human mesothelin CAR comprises two 4-1BB co-stimulatory domains, an FKBP and FRB dimerizer-binding pair, and an ITAM intracellular signaling domain. The three different antigen recognition domains shown here are anti-mesothelin HN1 scFv, SS1 scFv, and m912 scFv. All membrane-anchored polypeptides are disulfide bonded homo-dimers.

Generation of CAR Constructs

Sequences encoding the anti-mesothelin were cloned from constructs or synthesized via gene assembly by PCR. The human 4-1BB co-stimulation and CD3 zeta ITAM signaling chains were cloned from cDNAs supplied by Open Biosystems. HN1 scFv-, SS1 scFv-, and m912 scFv-encoding sequences were synthesized by PCR and, in some cases, codon optimized. FKBP- and FRB-encoding sequences were cloned from Addgene plasmids.

Standard molecular cloning techniques (polymerase chain reaction (PCR), restriction digestion, ligation, etc.) were applied to generate lentiviral expression plasmids.

Effector and Target Cell Culturing Conditions

A Jurkat cell line expressing GFP upon NFAT activation was maintained in RPMI-1640 medium supplemented with 10% FBS, penicillin and streptomycin. K562 target cells were cultured in IMDM supplemented with 10% fetal bovine serum (FBS).

Effector and Target Cell Engineering with Lentivirus

Pantropic VSV-G pseudotyped lentivirus was produced from Lenti-X 293T cells (Clontech Laboratories #632180) co-transfected with a pHR' SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Jurkat and K562 cells were split 1-2 days in advance to ensure that cultures would be in log phase at the time of transduction. Transduced Jurkat and K562 cells were cultured for at least 7 days before experiments were conducted. Expression levels of CARs encoded in the lentiviral constructs were quantified by detecting either fluorophore-conjugated antibodies or fluorescent reporter proteins using a flow cytometer.

Quantitation of IL-2 Production

Jurkat CD4+ T cells expressing CARs were mixed with cognate or non-cognate K562 target cells at a 1:2 effector:target ratio. The rapalog A/C Heterodimerizer (Clontech Laboratories #635055) were serially diluted in medium and added to reaction mixtures. After 20~24 hours of incubation, medium supernatants were collected and analyzed with BD OptEIA Human IL-2 ELISA Set (BD Biosciences #555190).

Results

Figure 19D:
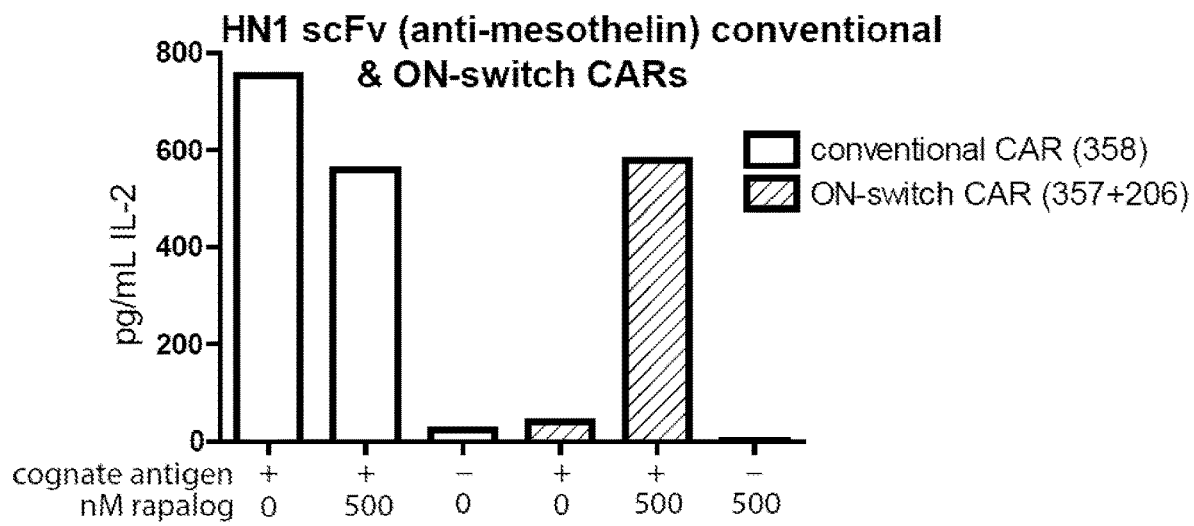
Figure 19E:
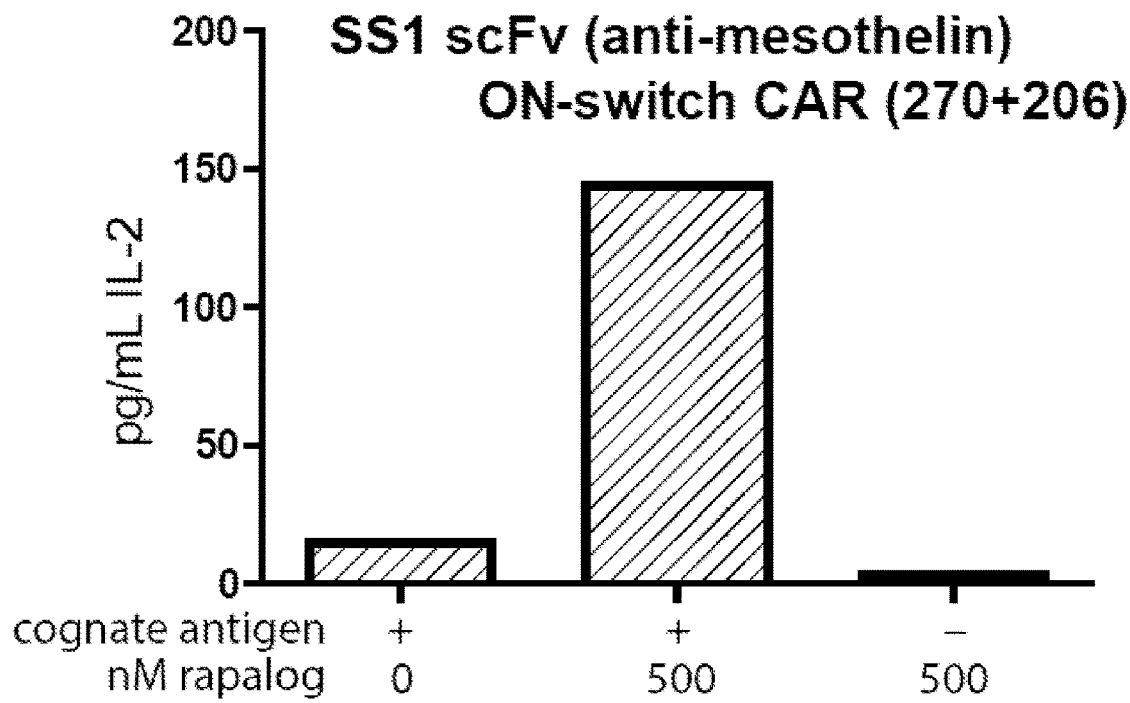
Figure 19F:
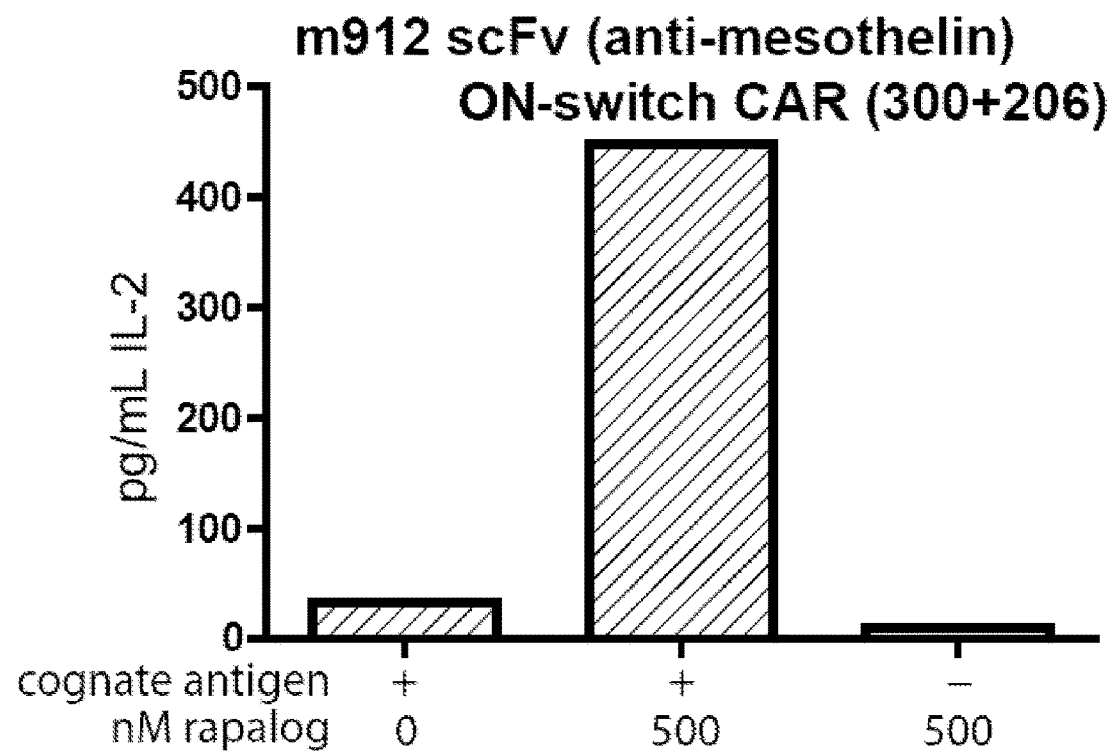
Figure 19G:
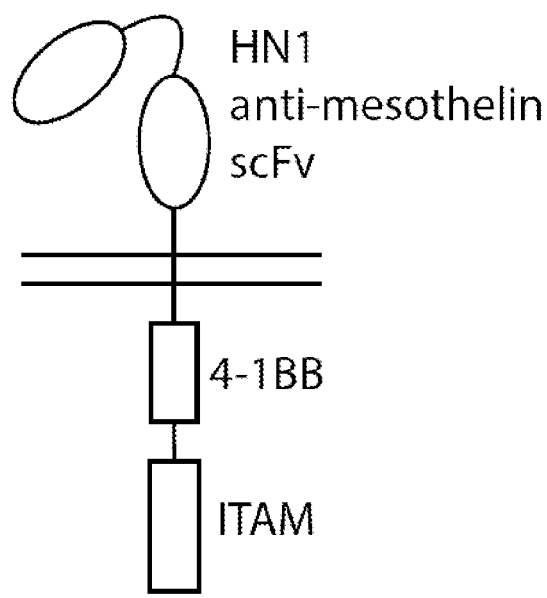

IL-2 production elicited by the anti-mesothelin CAR constructs was assessed. The data are presented in FIG. 19D-F.

FIG. 19. IL-2 production triggered by HN1 scFv (FIG. 19D), SS1 scFv (FIG. 19E), and m912 scFv (FIG. 19F) On-switch CAR variants. IL-2 production by a conventional CAR (FIG. 19G, construct #358) was measured and included for comparison to On-switch CARs (FIG. 19D). Effector=human CD4+ Jurkat T cells engineered with CARs. Target=K562 cell lines with or without the cognate mesothelin antigen. Amounts of secreted IL-2 by effector cells were quantified by enzyme-linked immunosorbent assay (ELISA).

Example 3: Gibberellic Acid as a Dimerizer of On-Switch CARs

Materials and Methods

Figure 20A:
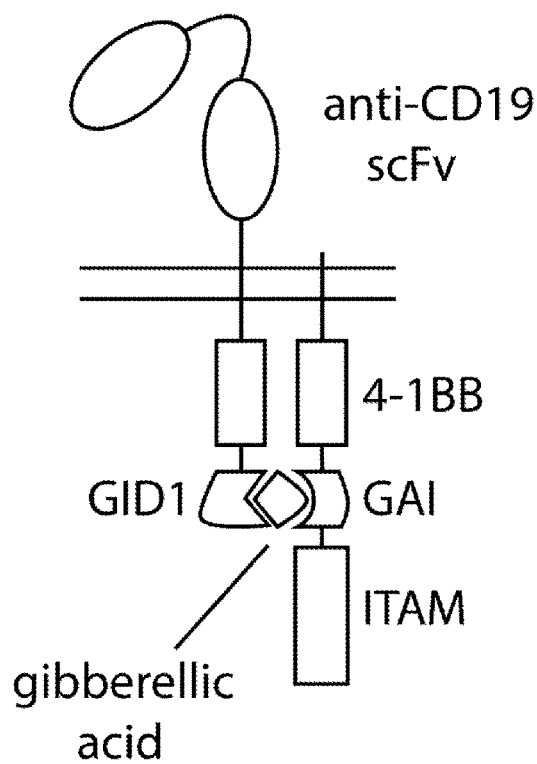
FIGS. 20A-C depict IL-2 production triggered by an On-switch CAR variant with a gibberellic acid responsive dimerization pair.

FIG. 20A summarizes the molecular structure of the subject gibberellic acid dimerizer CAR. The antigen binding portion comprises the anti-human CD19 scFv. The intracellular portion comprises two 4-1BB co-stimulatory domains, a GID1 and GAI dimerizer-binding pair, and an ITAM intracellular signaling domain. All membrane-anchored polypeptides are di-sulfide bonded homo-dimers.

Generation of CAR Constructs

Sequences encoding the gibberellic acid dimerizer CAR were cloned from constructs. The anti-CD19 scFv was cloned from a plasmid. The human 4-1BB co-stimulation and CD3 zeta ITAM signaling chains were cloned from cDNAs supplied by Open Biosystems. GID1- and GAI-encoding sequences were cloned from Addgene plasmids. Standard molecular cloning techniques (polymerase chain reaction (PCR), restriction digestion, ligation, etc.) were applied to generate lentiviral expression plasmids.

Effector and Target Cell Culturing Conditions

A Jurkat cell line expressing GFP upon NFAT activation was maintained in RPMI-1640 medium supplemented with 10% FBS, penicillin and streptomycin. K562 target cells were cultured in IMDM supplemented with 10% fetal bovine serum (FBS).

Effector and Target Cell Engineering with Lentivirus

Pantropic VSV-G pseudotyped lentivirus was produced from Lenti-X 293T cells (Clontech Laboratories #632180) co-transfected with a pHR' SIN:CSW transgene expression vector, viral packaging plasmids pCMVdR8.91 and pMD2.G using Lipofectamine LTX (Life Technologies #15338). Infection medium supernatant was collected 48 hours after transfection and used directly for transduction.

Jurkat and K562 cells were split 1-2 days in advance to ensure that cultures would be in log phase at the time of transduction. Transduced Jurkat and K562 cells were cultured for at least 7 days before experiments were conducted. Expression levels of CARs encoded in the lentiviral constructs were quantified by detecting either fluorophore-conjugated antibodies or fluorescent reporter proteins using a flow cytometer.

Quantitation of IL-2 Production

Jurkat CD4+ T cells expressing CARs were mixed with cognate or non-cognate K562 target cells at a 1:2 effector:target ratio. The gibberellic acid-3 acetoxymethyl ester (gibberrelic acid-3 AM) pre-dissolved in ethanol (Toronto Research Chemicals #G377500) was diluted in growth medium and added to reaction mixtures. Gibberellic acid (gibberellic acid-3 AM) was used at 10 mM. After 20~24 hours of incubation, medium supernatants were collected and analyzed with BD OptEIA Human IL-2 ELISA Set (BD Biosciences #555190).

Results

IL-2 production elicited by the gibberellic acid dimerizer CAR construct was assessed. The data are presented in FIG. 20.

Figure 20B:
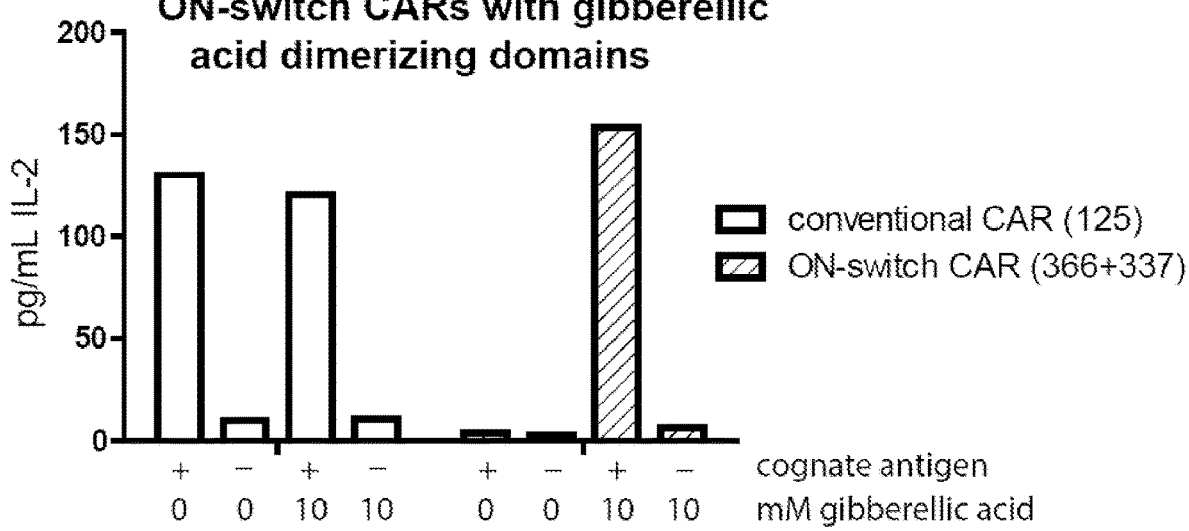
Figure 20C:
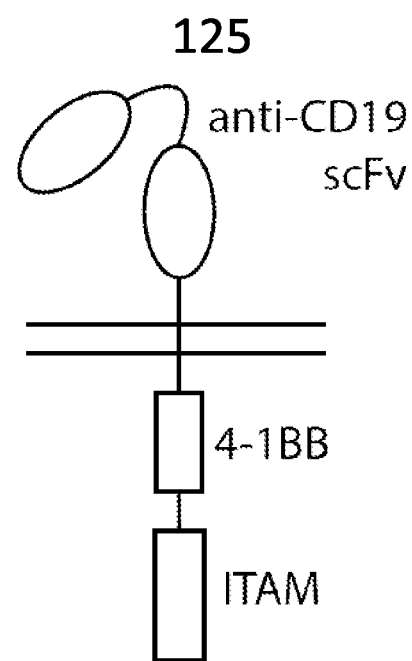

FIG. 20. IL-2 production triggered by gibberellic acid dimerizer CAR variant (FIG. 20B). IL-2 production by a conventional CAR (FIG. 20C, construct "125") was measured and included for comparison to On-switch CAR. Effector=human CD4+ Jurkat T cells engineered with CARs. Target=K562 cell lines with or without the cognate CD19 antigen. Amounts of secreted IL-2 by effector cells were quantified by enzyme-linked immunosorbent assay (ELISA).

Example 4: On-Switch CARs with Various Co-Stimulatory Domains

Materials and Methods

Figure 21A:
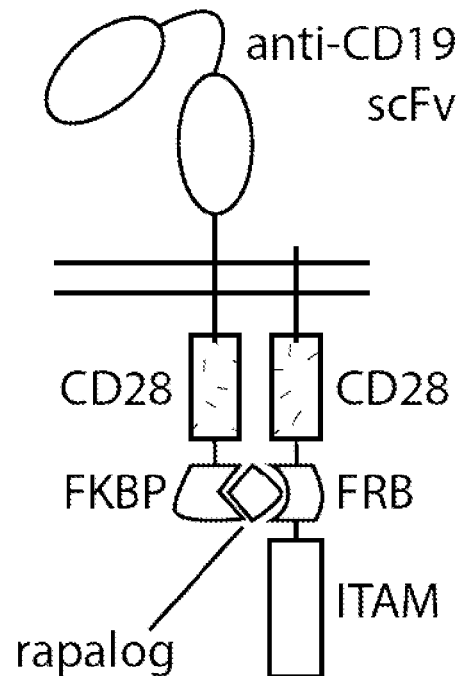
FIGS. 21A-D depict exemplary On-switch CARs and conventional CARs with various co-stimulatory domains.
Figure 21B:
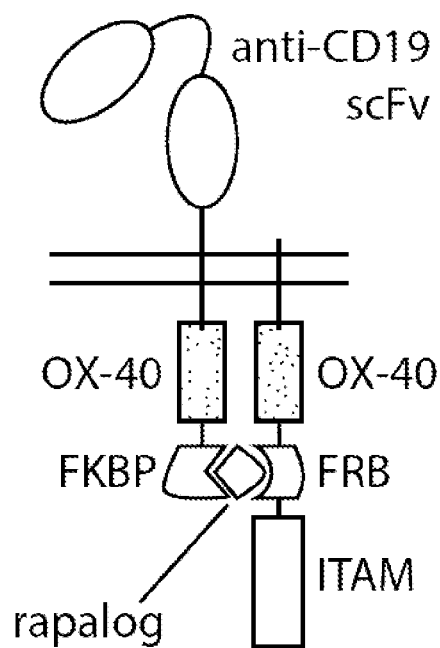

A number of chimeric antigen receptor constructs were made essentially as described for Example 1, except various other co-stimulatory domains were exchanged for the 4-1BB co-stimulatory domains. FIGS. 21A and 21B summarize the molecular structure of the CARs described here.

Generation of CAR Constructs

Sequences encoding the anti-human CD19 scFv were cloned from a plasmid. The human CD3 zeta ITAM signaling chain and the human co-stimulatory domains CD28 and OX-40 encoding sequences were cloned from cDNAs supplied by Open Biosystems. FKBP- and FRB-encoding sequences were cloned from plasmids from Addgene.

Standard molecular cloning techniques (polymerase chain reaction (PCR), restriction digestion, ligation, etc.) were applied to generate lentiviral expression plasmids.

Testing of CAR Constructs

Figure 21C:
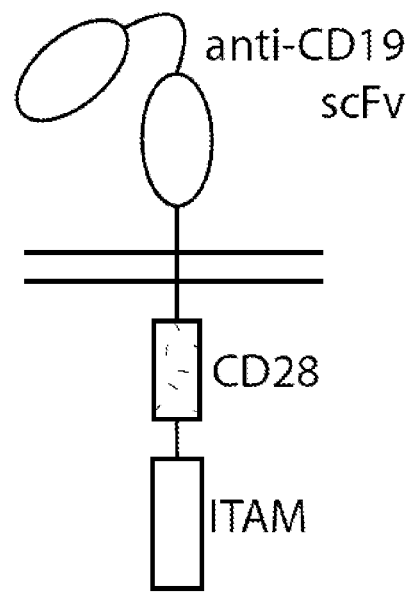
Figure 21D:
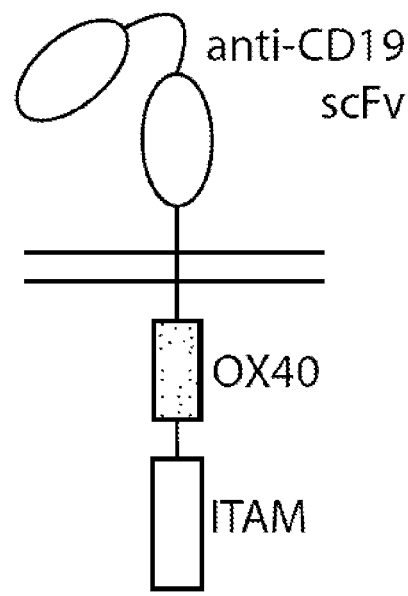

Effector and target cells are cultured and transfected according to Example 1 using the on-switch CAR CD28 and OX-40 co-stimulatory domain containing constructs described (FIG. 21A-B, constructs "365+367" and "399+400", respectively) and corresponding conventional CAR controls (FIG. 21C-D, constructs "366" and "398", respectively). IL-2 production, NFAT activity assays, and flow cytometry-based assays can also be performed with the CD28 co-stimulatory domain containing construct and OX-40 co-stimulatory domain containing construct as described for Example 1. Alternatively, subunits of on-switch CAR CD28 and OX-40 co-stimulatory domain containing constructs can be paired with subunits of constructs from Example 1 (e.g., "197+367", "365+206," "197+400", "399+206," etc.).

Example 5: In Vivo Assessment of On-Switch CAR

An On-switch CAR can be assessed for its ability to mediate in vivo killing of a target tumor cell. In vivo tumor cell killing elicited by injection of T cells expressing the ON-switch CAR is assessed. Tumor cell lines that have been confirmed in vitro to express the cognate antigen and can be killed by CD8+ T cells expressing the corresponding CAR are used. Tumor cells engineered to express either the firefly or Renilla luciferase to enable bio-luminescence imaging to quantify tumor burden in vivo can be used. Tumor cells are injected into immunocompromised mice (e.g., 6~10 week old female NOD scid gamma (NSG) mice) either subcutaneously for subcutaneous tumor models or intravenously for systemic tumor models. The method of tumor implantation and the optimal number of tumor cells to implant can be based on conditions optimal for the tumor cell line used. Tumor burden can be monitored twice a week by bio-luminescence imaging and by caliper measurement when applicable. As soon as tumor burden is detectable, $0.5~2.5 \times 10^7$ total T cells (1:1 $CD4^+:CD8^+$) expressing the ON-switch CAR are intravenously injected into mice to begin treatment. A dimerizing small molecule drug (e.g., rapalog) is administered intraperitoneally in a vehicle formulation. On-switch CAR-expressing T cells can be injected repeatedly during the experiment to enhance the anti-tumor effect. Interleukin-2 (IL-2) can be administered to enhance the anti-tumor effect.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. One or more nucleic acids comprising a nucleotide sequence(s) encoding a heterodimeric chimeric antigen receptor (CAR) comprising:
   a first polypeptide comprising a first member of a dimerization pair, a first transmembrane domain, and an intracellular signaling domain; and
   a second polypeptide comprising a scFv or VHH domain that specifically binds to mesothelin, a second member of the dimerization pair, and a second transmembrane domain;
   wherein:
   the first and second members of the dimerization pair are intracellular,
   a dimerizing agent dimerizes the heterodimeric CAR when the first and second polypeptides are expressed by a cell with the dimerizing agent bound between the dimerization pair members of the first and second polypeptides,
   the first polypeptide does not comprise an antigen-binding domain and the second polypeptide does not comprise an intracellular signaling domain capable of inducing cell activation, and
   activation of the cell by the formed heterodimeric CAR binding mesothelin or said antigen is increased as compared to activation of the cell in the absence of the dimerizing agent.

2. The one or more nucleic acids according to claim 1, wherein the intracellular signaling domain is a CD3-zeta intracellular signaling domain or a ZAP-70 intracellular signaling domain.

3. The one or more nucleic acids according to claim 1, wherein the intracellular signaling domain comprises an immunoreceptor tyrosine-based activation motif (ITAM).

4. The one or more nucleic acids according to claim 1, wherein the first polypeptide, the second polypeptide or both comprise an intracellular costimulatory polypeptide.

5. The one or more nucleic acids according to claim 1, wherein the intracellular costimulatory polypeptides are selected from the group consisting of: 4-1BB, CD28, ICOS, OX-40, BTLA, CD27, CD30, GITR, and HVEM.

6. The one or more nucleic acids according to claim 1, wherein the first polypeptide comprises a first costimulatory polypeptide comprising an amino acid sequence and the second polypeptide comprises a second costimulatory polypeptide comprising an amino acid sequence that has at least 95% amino acid identity to the amino acid sequence of the first costimulatory polypeptide in the first polypeptide.

7. The one or more nucleic acids according to claim 1, wherein the dimerizer agent is selected from the group consisting of: rapamycin, coumermycin, methotrexate, AP20187, abscisic acid, gibberellin and analogs thereof.

8. The one or more nucleic acids according to claim 1, wherein the first and second members of the dimerization pair are selected from the group consisting of:
   a) FK506 binding protein (FKBP) and FKBP-rapamycin associated protein (FRB);
   b) a Gibberellic Acid Insensitive (GAI) protein and a gibberellin receptor (GID1) protein;
   c) FKBP and calcineurin catalytic subunit A (CnA);
   d) an abscisic acid receptor (PYL) protein and an abscisic acid insensitive (ABI) protein; and
   e) FKBP and cyclophilin.

9. The one or more nucleic acids according to claim 1, wherein the first and second members of the dimerization pair are selected from the group consisting of:
   a) FK506 binding protein (FKBP) and FKBP;
   b) gyrase B (GyrB) and GyrB;
   c) dihydrofolate reductase (DHFR) and DHFR; and
   d) DmrB and DmrB.

10. An isolated cell comprising the one or more nucleic acids according to claim 1.

11. The isolated cell according to claim 10, wherein the isolated cell is an immune cell.

12. The isolated cell according to claim 11, wherein the immune cell is a lymphocyte or a NK cell.

13. The isolated cell according to claim 10, wherein the cell is a human cell.

* * * * *